(12) United States Patent
Basinger et al.

(10) Patent No.: US 9,150,572 B2
(45) Date of Patent: Oct. 6, 2015

(54) SUBSTITUTED NAPHTHYRIDINE AND QUINOLINE COMPOUNDS AS MAO INHIBITORS

(71) Applicant: DART NEUROSCIENCE (CAYMAN) LTD., Grand Cayman (KY)

(72) Inventors: Jillian Basinger, San Diego, CA (US); Graeme Freestone, San Diego, CA (US); Varsha Gupta, Encinitas, CA (US); Alan Kaplan, San Diego, CA (US); Chi-Ching Mak, San Diego, CA (US); Benjamin Pratt, Encinitas, CA (US); Vincent Santora, San Diego, CA (US); Dipanjan Sengupta, San Diego, CA (US); Lino Valdez, Carlsbad, CA (US)

(73) Assignee: Dart NeuroScience (Cayman) Ltd. (KY)

( * ) Notice: Subject to any disclaimer, the term of this patent is extended or adjusted under 35 U.S.C. 154(b) by 0 days.

(21) Appl. No.: 14/205,195

(22) Filed: Mar. 11, 2014

(65) Prior Publication Data

US 2014/0275548 A1   Sep. 18, 2014

Related U.S. Application Data

(60) Provisional application No. 61/785,872, filed on Mar. 14, 2013.

(51) Int. Cl.
| | | |
|---|---|---|
| C07D 471/02 | (2006.01) | |
| C07D 215/00 | (2006.01) | |
| C07D 471/04 | (2006.01) | |
| C07D 215/54 | (2006.01) | |

(52) U.S. Cl.
CPC ............ *C07D 471/04* (2013.01); *C07D 215/54* (2013.01)
USPC ............................ 546/123; 546/152; 546/153

(58) Field of Classification Search
CPC ...................... C07D 471/02; C07D 215/00
USPC ......................................... 546/123, 152, 153
See application file for complete search history.

(56) References Cited

U.S. PATENT DOCUMENTS

| | | | |
|---|---|---|---|
| 4,938,949 A | | 7/1990 | Borch et al. |
| 6,121,288 A | | 9/2000 | Masui et al. |
| 7,868,015 B2 | | 1/2011 | Tully et al. |
| 7,947,731 B2 | | 5/2011 | Tully et al. |
| 8,138,209 B2 | | 3/2012 | McElroy et al. |
| 8,222,243 B2 | | 7/2012 | Kaplan et al. |
| 8,338,429 B2 * | | 12/2012 | Sugasawa et al. ....... 514/253.09 |
| 2007/0203154 A1 | | 8/2007 | Zhou et al. |
| 2008/0188525 A1 | | 8/2008 | Hallam et al. |
| 2009/0053140 A1 | | 2/2009 | Scott et al. |
| 2010/0317648 A1 | | 12/2010 | Zhou et al. |
| 2011/0118289 A1 | | 5/2011 | Giordani et al. |
| 2011/0160248 A1 | | 6/2011 | Zhou et al. |

FOREIGN PATENT DOCUMENTS

| | | |
|---|---|---|
| EP | 0 504 574 A1 | 9/1992 |
| EP | 0 994 095 A1 | 4/2000 |
| JP | 2002-322163 (A) | 11/2002 |
| WO | WO 96/12710 A1 | 5/1996 |
| WO | WO 03/057216 A1 | 7/2003 |
| WO | WO 2004/026827 A1 | 4/2004 |
| WO | WO 2005/039591 A1 | 5/2005 |
| WO | WO 2006/097270 A1 | 9/2006 |
| WO | WO 2006/102958 A1 | 10/2006 |
| WO | WO 2010/051196 A1 | 5/2010 |
| WO | WO 2010/086484 A1 | 8/2010 |
| WO | WO 2010/098600 A2 | 9/2010 |

OTHER PUBLICATIONS

Amit et al., "Targeting multiple Alzheimer's disease etiologies with multimodal neuroprotective and neurorestorative iron chelators," *The FASEB Journal*, May 2008, 22: 1296-1305.
Binda et al., "Structures of Human Monoamine Oxidase B Complexes with Selective Noncovalent Inhibitors: Safinamide and Coumarin Analogs," *J. Med. Chem.* 2007, 50(23): 5848-5852.
Fiorito et al., "Synthesis of Quinoline Derivatives: Discovery of a Potent and Selective Phosphodiesterase 5 Inhibitor for the Treatment of Alzheimer's disease," *Eur J Med Chem.*, Feb. 2013; 60: 285-294.
Gnerre et al., "Inhibition of Monoamine Oxidases by Functionalized Coumarin Derivatives: Biological Activities, QSARs, and 3D-QSARs," *J. Med. Chem.*, 2000, 43(25): 4747-4758.
Pérez et al., "Relevance of benzyloxy group in 2-indolyl methylamines in the selective MAO-B inhibition," *British Journal of Pharmacology*, 1999, 127: 869-876.
International Search Report and Written Opinion dated Jul. 21, 2014 for International Patent Application No. PCT/US2014/020881 filed Mar. 5, 2014.

* cited by examiner

*Primary Examiner* — Niloofar Rahmani
(74) *Attorney, Agent, or Firm* — Knobbe Martens Olson & Bear LLP

(57) ABSTRACT

The invention provides a chemical entity of Formula (I)

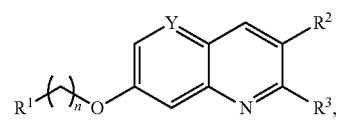

wherein $R^1$, $R^2$, $R^3$, Y, and n have any of the values described herein and compositions comprising such chemical entities; methods of making them; and their use in a wide range of methods, including metabolic and reaction kinetic studies, detection and imaging techniques, and radioactive treatments; and therapies, including inhibiting MAO, and MAO-B selectively, enhancing neuronal plasticity, treating neurological disorders, providing neuroprotection, treating a cognitive impairment associated with a CNS disorder, enhancing the efficiency of cognitive and motor training, providing neurorecovery and neurorehabilitation, enhancing the efficiency of non-human animal training protocols, and treating treating peripheral disorders (including obesity, diabetes, and cardiometabolic disorders) and their associated co-morbidities.

3 Claims, No Drawings

SUBSTITUTED NAPHTHYRIDINE AND QUINOLINE COMPOUNDS AS MAO INHIBITORS

INCORPORATION BY REFERENCE TO ANY PRIORITY APPLICATIONS

Any and all priority claims identified in the Application Data Sheet, or any correction thereto, are hereby incorporated by reference under 37 CFR 1.57. For example, this application claims the benefit under 35 U.S.C. §119(e) to U.S. Provisional Application No. 61/785,872, filed on Mar. 14, 2013, which is incorporated herein by reference in its entirety.

BACKGROUND

1. Field

The present invention relates to certain disubstituted 1,5-naphthyridine and quinoline compounds as inhibitors of monamine oxidase, and monoamine oxidase B in particular; derivatives of such compounds; compositions of such compounds; methods of making them; and their use in various methods, including detection and imaging techniques; enhancing neuronal plasticity; treating neurological disorders, including neurodegenerative and cognitive disorders; providing neuroprotection; enhancing the efficiency of cognitive and motor training; facilitating neurorecovery and neurorehabilitation; and treating peripheral disorders, including obesity, diabetes, cardiometabolic disorders, and their associated co-morbidities.

2. Description of the Related Technology

Monoamine oxidase (MAO, E.C. 1.4.3.4) is a mitochondrial-bound, flavin-containing, enzyme that catalyzes the oxidative deamination of biogenic (endogenous) and xenobiotic (exogenous) amines. Biogenic amines can be divided into three categories: monoamines, such as serotonin (5-hydroxytryptamine, 5-HT) and tryptamine; catecholamines, such as dopamine (DA), norepinephrine (NE), and epinephrine; and trace amines such as beta-phenylethylamine (PEA), tyramine, and octopamine.

Oxidative deamination by MAO requires the cofactor FAD and results in formation of the corresponding aldehyde, which then is usually rapidly oxidized into a carboxylic acid by aldehyde dehydrogenase (ALDH). The byproducts of these reactions include potentially neurotoxic species, such as hydrogen peroxide and ammonia. Hydrogen peroxide, for example, can trigger the production of reactive oxygen species (ROS) and induce mitochondrial damage and neuronal apoptosis. Proper regulation of MAOs therefore appears crucial in maintaining proper nervous system function.

There are two MAO isoforms (types A and B), corresponding to the mao-A and mao-B genes, and they show distinct expression patterns (e.g., Riederer et al., *J. Neural Transm.* 1978, 43, 217-226; Saura et al., *J. Neural Transm. Suppl.* 1990, 32, 49-53; and Saura et al., *Neuroscience* 1996, 70, 755-774). In peripheral tissues, MAO-A is primarily found in the liver and gastrointestinal tract, whereas MAO-B is primarily found in blood platelets. In the human brain, MAO-A is predominantly expressed in catecholaminergic neurons, whereas MAO-B is mostly concentrated in astrocytes and astroglia but also expressed in serotonergic neurons, histaminergic cells, and astrocytes. MAO-A and MAO-B also display overlapping but distinct substrate preferences: Both forms show a similar preference for dopamine (DA), tyramine, and tryptamine; however, MAO-A preferentially metabolizes serotonin (5-HT) and noradrenaline (NE), whereas MAO-B preferentially metabolizes histamine and phenethylamine.

The ability of MAO enzymes to rapidly degrade brain monoamines such as 5-HT, NE, and DA is essential for proper synaptic neurotransmission. Monoaminergic signaling is a key mechanism for modulating mood and emotion, as well as controlling motor, perceptual and cognitive functions. More generally, MAO-B levels in the brain naturally increase with age, with significant increases observed after 50 to 60 years of age. Increases in MAO-B contribute to cellular degeneration by producing hydrogen peroxides that are converted by iron to highly toxic oxygen free radicals and leads to cell death. Likewise, perturbations in MAO activity are associated with numerous pathological processes. For example, increased MAO-B activity in the brain has been observed in Alzheimer's and Parkinson's patients, implicating oxidative damage in neurodegenerative and cognitive dysfunction (e.g., Fowler et al., *J. Neural. Transm,* 1980, 49, 1-20; Dostert et al., *Biochem. Pharmacol.* 1989, 38, 555-561; and Emilsson et al., *Neurosci. Lett.* 2002, 326, 56-60).

These observations highlight the interest in MAO-inhibition as a therapeutic target for numerous disorders (e.g., Bentue-Ferrer et al., *CNS Drugs,* 1996, 217-236). By increasing the concentration of monoamines present within the brain synapses, MAO inhibitors can enhance monoamine-mediated neurotransmission, effectively treating neurological and psychiatric disorders such as Parkinson's disease and depression. In addition, because MAO inhibitors have demonstrated antioxidant and anti-apoptotic activity in experimental models, they may offer neuroprotective benefits by curbing the production of toxic oxidative species during MAO catalysis (e.g., Youdim et al., *Nat. Rev. Neurosci.* 2006, 7, 295-309; Al-Nuaimi et al., *Am. J. Ther.* 2012, 19, 436-448.

A wide variety of MAO inhibitors been reported, including phenylcoumarine derivatives (ES2343347, Jul. 28, 2010), substituted azole derivatives (International Publication No. WO 2010098600, Sep. 2, 2010), axabenzoxazole derivatives (WO 2010051196, May 6, 2010), pyrazole derivatives (US20070203154, Aug. 30, 2007), benzopyran derivatives (WO 2006102958, Oct. 5, 2006), pyrrolidinylphenyl benzyl ether derivatives (WO 2006097270, Sep. 21, 2006), benzyloxybenzazepine derivatives (WO 200503951, May 6, 2005), arylpyrrolidinone derivatives (WO 200402687, Apr. 1, 2004), and substituted oxadiazole derivatives (EP504574, Sep. 23, 1992).

However, MAO inhibitors have generally been associated with numerous side effects that have typically limited their usefulness and tolerability. The first generation of MAO inhibitors—initially introduced in the 1950s for treating depression—was irreversible and non-selective. Use of these inhibitors was gradually abandoned mainly due to their potential for drug-drug and drug-food interactions, the most widely known being with tyramine-containing food (the 'cheese' effect). Moreover, when MAO inhibitors are used in high dosage, cardiovascular effects seem to increase considerably, and because MAO selectivity is lost with such high doses, tyramine can induce potentially dangerous hypertensive reactions. More recent drugs, including selegiline and rasagiline, show greater selectivity for MAO-B and may have better side effect profiles, but they still suffer from limitations owing to irreversible binding (Chen and Swope, *J. Clin. Pharmacol.* 2005, 45, 878-894).

It is therefore desirable to develop improved MAO inhibitors such as those showing higher potency, greater specificity, and better side effect profiles. The present invention meets these and other needs in the art by disclosing substituted naphthyridine and quinoline compounds as inhibitors of MAO, and more particularly, MAO-B.

SUMMARY

The invention provides a chemical entity of Formula (I):

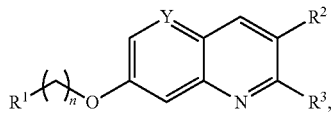

Formula (I)

wherein
$R^1$, $R^2$, $R^3$, Y, and n have any of the values described herein.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I).

Chemical entities of Formula (I) are useful in wide range of methods. Isotopically-labeled compounds and prodrugs can be used in metabolic and reaction kinetic studies, detection and imaging techniques, and radioactive treatments. The chemical embodiments of the present invention can be used to inhibit MAO, and MAO-B, in particular; to treat a disorder mediated by MAO, and MAO-B, in particular; to enhance neuronal plasticity; to treat neurological disorders, including neurodegenerative disorders, cognitive disorders, and cognitive deficits associated with CNS disorders; to confer neuroprotection; and to treat peripheral disorders, including obesity, diabetes, cardiometabolic disorders, and their associated co-morbidities. The chemical embodiments of the present invention are also useful as augmenting agents to enhance the efficiency of cognitive and motor training, to facilitate neurorecovery and neurorehabilitation, and to increase the efficiency of non-human animal training protocols. The invention is further directed to the general and specific embodiments defined, respectively, by the independent and dependent claims appended hereto, which are incorporated by reference herein.

DETAILED DESCRIPTION

The invention may be more fully appreciated by reference to the following description, including the examples. Unless otherwise defined, all technical and scientific terms used herein have the same meaning as commonly understood by one of ordinary skill in the art. Although methods and materials similar or equivalent to those described herein can be used in the practice or testing of the present invention, suitable methods and materials are described herein. In addition, the materials, methods, and examples are illustrative only and not intended to be limiting.

For the sake of brevity, all publications, including patent applications, patents, and other citations mentioned herein, are incorporated by reference in their entirety. Citation of any such publication, however, shall not be construed as an admission that it is prior art to the present invention.

ABBREVIATIONS

The specification includes numerous abbreviations, whose meanings are listed in the following Table:

| Abbreviation | Meaning |
|---|---|
| ACN | Acetonitrile |
| BINAP | 2,2'-Bis(diphenylphosphino)-1,1'-binaphthyl |
| BOC | tert-butoxycarbonyl |
| BOC anhydride | Di-tert-butyl dicarbonate |
| DBU | 1,8-Diazabicyclo[5.4.0]undec-7-ene |
| DCM | Dichloromethane |
| diglyme | (2-Methoxyethyl) ether |
| DIPEA | N,N-ethyl-diisopropylamine or N,N-Diisopropyl- |
| DMA | N,N-Dimethylacetamide |
| DMAP | 4-Dimethylamino pyridine |
| DME | Dimethoxyethane |
| DMF | N,N-Dimethylformamide |
| DMSO | Dimethylsulfoxide |
| Dowtherm ™ | Biphenyl ($C_{12}H_{10}$) and Diphenyl oxide ($C_{12}H_{10}O$) eutectic mixture |
| dppf | 1,1'-Bis(diphenylphosphino)ferrocene |
| EDCI | N-(3-Dimethylaminopropyl)-N'- |
| EtOAc, or EA | Ethyl Acetate |
| EtOH | Ethanol |
| HATU | 2-(1H-9-Azobenzotriazole-1-yl)-1,1,3,3-tetramethylaminium hexafluorophosphate |
| HOAc or AcOH | Acetic Acid |
| HOAT | 1-Hydroxy-7-azabenzotriazole |
| HPLC | High-performance liquid chromatography |
| KHMDS | Potassium bis(trimethylsilyl)amide |
| LAH | Lithium aluminum hydride |
| LiHMDS, LHMDS | Lithium bis(trimethylsilyl)amide |
| LCMS, LC/MS | Liquid chromatography-mass spectrometry |
| MeOH | Methanol |
| MsCI | Methanesulfonyl chloride |
| MTBE | Methyl tert-butyl ether |
| NMP | 1-Methyl-2-pyrrolidinone |
| Pd/C | Palladium on activated carbon |
| $Pd_2(dba)_3$ | Tris(dibenzylideneacetone)dipalladium (0) |
| $PdCl_2(dppf)$-dcm adduct | [1'1'-Bis(diphenylphosphino)ferrocene]palladium(ll) |
| TEA, $Et_3N$ | Triethylamine |
| TFA | Trifluoroacetic acid |
| THF | Tetrahydrofuran |
| TLC | Thin layer chromatography |
| XtalFluor ® | (Diethylamino)difluorosulfonium tetratetrafluoroborate |

TERMS AND DEFINITIONS

The use of subheadings such as "General," "Chemistry," "Compositions," "Formulations," etc., in this section, as well as in other sections of this application, are solely for convenience of reference and not intended to be limiting.

General

As used herein, the term "about" or "approximately" means within an acceptable range for a particular value as determined by one skilled in the art, and may depend in part on how the value is measured or determined, e.g., the limitations of the measurement system or technique. For example, "about" can mean a range of up to 20%, up to 10%, up to 5%, or up to 1% or less on either side of a given value. Alternatively, with respect to biological systems or processes, the term "about" can mean within an order of magnitude, within 5 fold, or within 2 fold on either side of a value. Numerical quantities given herein are approximate unless stated otherwise, meaning that the term "about" or "approximately" can be inferred when not expressly stated To provide a more concise description, some of the quantitative expressions given herein are not qualified with the term "about". It is understood that, whether the term "about" is used explicitly or not, every quantity given herein is meant to refer to the actual given value, and it is also meant to refer to the approximation of such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity for which that could be obtained under the particular stoichiometric conditions. Concentrations that are given as percentages refer to mass ratios, unless indicated differently.

As used herein, the terms "a," "an," and "the" are to be understood as meaning both singular and plural, unless explicitly stated otherwise. Thus, "a," "an," and "the" (and grammatical variations thereof where appropriate) refer to one or more.

A group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise. Furthermore, although items, elements or components of the invention may be described or claimed in the singular, the plural is contemplated to be within the scope thereof, unless limitation to the singular is explicitly stated.

The terms "comprising" and "including" are used herein in their open, non-limiting sense. Other terms and phrases used in this document, and variations thereof, unless otherwise expressly stated, should be construed as open ended, as opposed to limiting. As examples of the foregoing: the term "example" is used to provide exemplary instances of the item in discussion, not an exhaustive or limiting list thereof; adjectives such as "conventional," "traditional," "normal," "criterion," "known," and terms of similar meaning should not be construed as limiting the item described to a given time period or to an item available as of a given time, but instead should be read to encompass conventional, traditional, normal, or criterion technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. As will become apparent to one of ordinary skill in the art after reading this document, the illustrated embodiments and their various alternatives may be implemented without confinement to the illustrated examples.

Chemistry

The term "alkyl" refers to a fully saturated aliphatic hydrocarbon group. The alkyl moiety may be a straight- or branched-chain alkyl group having from 1 to 12 carbon atoms in the chain. Examples of alkyl groups include, but are not limited to, methyl (Me, which also may be structurally depicted by the symbol, "━━"), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "haloalkyl" refers to a straight- or branched-chain alkyl group having from 1 to 12 carbon atoms in the chain optionally substituting hydrogens with halogens. Examples of haloalkyl groups include, but are not limited to, —$CF_3$, —$CHF_2$, —$CH_2F$, —$CH_2CF_3$, —$CH_2CHF_2$, —$CH_2CH_2F$, —$CH_2CH_2Cl$, —$CH_2CF_2CF_3$. and other groups that in light of the ordinary skill in the art and the teachings provided herein, would be considered equivalent to any one of the foregoing examples.

The term "alkoxy" includes a straight chain or branched alkyl group with an oxygen atom linking the alkyl group to the rest of the molecule. Alkoxy includes methoxy, ethoxy, propoxy, isopropoxy, butoxy, t-butoxy, pentoxy and so on. "Aminoalkyl", "thioalkyl", and "sulfonylalkyl" are analogous to alkoxy, replacing the terminal oxygen atom of alkoxy with, respectively, NH (or NR), S, and $SO_2$.

The term "cyano" refers to the group —CN.

The term "aryl" refers to a monocyclic, or fused or spiro polycyclic, aromatic carbocycle (ring structure having ring atoms that are all carbon), having from 3 to 12 ring atoms per ring. (Carbon atoms in aryl groups are sp2 hybridized.) Illustrative examples of aryl groups include the following moieties:

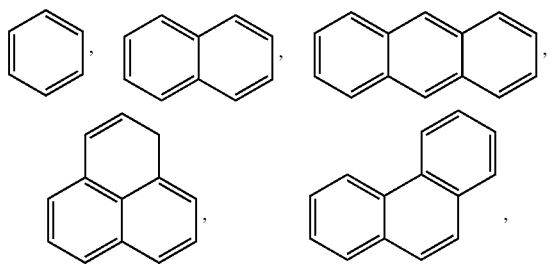

and the like.

The term "cycloalkyl" refers to a saturated or partially saturated carbocycle, such as monocyclic, fused polycyclic, bridged monocyclic, bridged polycyclic, spirocyclic, or spiro polycyclic carbocycle having from 3 to 12 ring atoms per carbocycle. Where the term cycloalkyl is qualified by a specific characterization, such as monocyclic, fused polycyclic, bridged polycyclic, spirocyclic, and spiro polycyclic, then such term cycloalkyl refers only to the carbocycle so characterized. Illustrative examples of cycloalkyl groups include the following entities, in the form of properly bonded moieties:

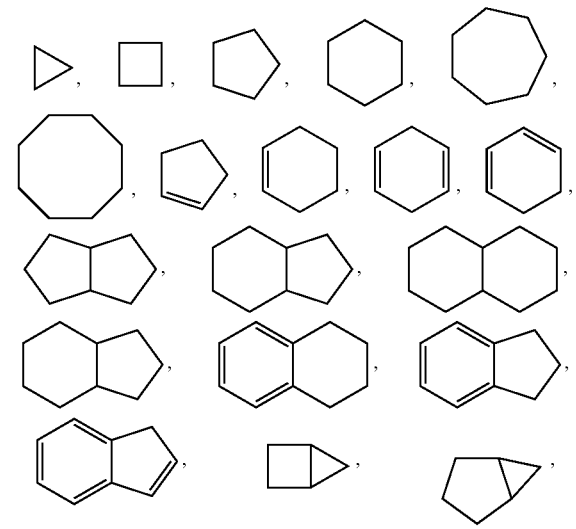

-continued

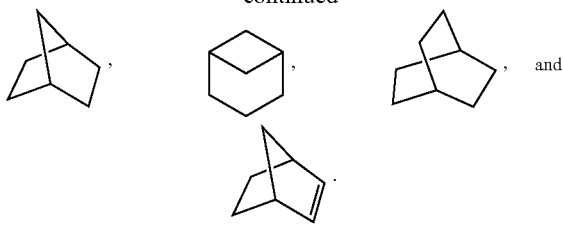

Those skilled in the art will recognize that the species of cycloalkyl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "heteroatom" used herein refers to, for example, O (oxygen), S (sulfur), or N (nitrogen).

The terms "para", "meta", and "ortho" have the meanings as understood in the art. Thus, for example, a fully substituted phenyl group has substituents at both "ortho"(o) positions adjacent to the point of attachment of the phenyl ring, both "meta" (m) positions, and the one "para" (p) position across from the point of attachment as illustrated below.

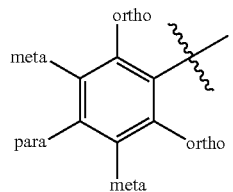

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Formulas

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers.

As used herein, "tautomer" refers to the migration of protons between adjacent single and double bonds. The tautomerization process is reversible. Compounds described herein can undergo any possible tautomerization that is within the physical characteristics of the compound. The following is an example tautomerization that can occur in compounds described herein:

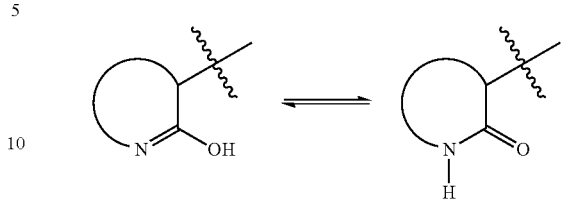

The symbols ▬▬ and ◀▬▬ are used as meaning the same spacial arrangement in chemical structures shown herein. Analogously, the symbols ı ı ı ı ı ı and • • ı ı ı ı are used as meaning the same spatial arrangement in chemical structures shown herein.

Compounds

As used herein, a "compound" refers to any one of: (a) the actually recited form of such compound; and (b) any of the forms of such compound in the medium in which the compound is being considered when named. For example, reference herein to a compound such as R—COOH, encompasses reference to any one of, for example, R—COOH(s), R—COOH(sol), and R—COO-(sol). In this example, R—COOH(s) refers to the solid compound, as it could be for example in a tablet or some other solid pharmaceutical composition or preparation; R—COOH(sol) refers to the undissociated form of the compound in a solvent; and R—COO-(sol) refers to the dissociated form of the compound in a solvent, such as the dissociated form of the compound in an aqueous environment, whether such dissociated form derives from R—COOH, from a salt thereof, or from any other entity that yields R—COO— upon dissociation in the medium being considered.

As used herein, the term "chemical entity" collectively refers to a compound, along with the derivatives of the compound, including salts, chelates, solvates, conformers, non-covalent complexes, metabolites, and prodrugs.

In one aspect the chemical entity is selected from the group consisting of compounds of Formula (I), pharmaceutically acceptable salts of compounds of Formula (I), pharmaceutically acceptable prodrugs of compounds of Formula (I), and pharmaceutically acceptable metabolites of compounds of Formula (I).

In another example, an expression such as "exposing an entity to a compound of formula R—COOH" refers to the exposure of such entity to the form, or forms, of the compound R—COOH that exists, or exist, in the medium in which such exposure takes place. In still another example, an expression such as "reacting an entity with a compound of formula R—COOH" refers to the reacting of (a) such entity in the chemically relevant form, or forms, of such entity that exists, or exist, in the medium in which such reacting takes place, with (b) the chemically relevant form, or forms, of the compound R—COOH that exists, or exist, in the medium in which such reacting takes place. In this regard, if such entity is for example in an aqueous environment, it is understood that the compound R—COOH is in such same medium, and therefore the entity is being exposed to species such as R—COOH(aq) and/or R—COO-(aq), where the subscript "(aq)" stands for "aqueous" according to its conventional meaning in chemistry and biochemistry. A carboxylic acid functional group has been chosen in these nomenclature examples; this choice is not intended, however, as a limitation but it is merely an illustration. It is understood that analogous examples can be provided in terms of other functional groups, including but not limited to hydroxyl, basic nitrogen members, such as those in amines, and any other group that interacts or transforms according to known manners in the medium that contains the compound. Such interactions and transformations include, but are not limited to, dissociation, association, tautomerism, solvolysis, including hydrolysis, solvation, including hydration, protonation and deprotonation. No further examples in this regard are provided herein because these interactions and transformations in a given medium are known by any one of ordinary skill in the art.

In another example, a "zwitterionic" compound is encompassed herein by referring to a compound that is known to form a zwitterion, even if it is not explicitly named in its zwitterionic form. Terms such as zwitterion, zwitterions, and their synonyms zwitterionic compound(s) are standard IUPAC-endorsed names that are well known and part of standard sets of defined scientific names. In this regard, the name zwitterion is assigned the name identification CHEBI:27369 by the Chemical Entities of Biological Interest (ChEBI) dictionary of molecular entities. As is generally well known, a zwitterion or zwitterionic compound is a neutral compound that has formal unit charges of opposite sign. Sometimes these compounds are referred to by the term "inner salts". Other sources refer to these compounds as "dipolar ions", although the latter term is regarded by still other sources as a misnomer. As a specific example, aminoethanoic acid (the amino acid glycine) has the formula $H_2NCH_2COOH$, and it exists in some media (in this case in neutral media) in the form of the zwitterion $+H_3NCH_2COO-$. Zwitterions, zwitterionic compounds, inner salts, and dipolar ions in the known and well established meanings of these terms are within the scope of this invention, as would in any case be so appreciated by those of ordinary skill in the art. Because there is no need to name each and every embodiment that would be recognized by those of ordinary skill in the art, no structures of the zwitterionic compounds that are associated with the compounds of this invention are given explicitly herein. They are, however, part of the embodiments of this invention. No further examples in this regard are provided herein because the interactions and transformations in a given medium that lead to the various forms of a given compound are known by any one of ordinary skill in the art.

Isotopes may be present in the compounds described. Each chemical element present in a compound either specifically or generically described herein may include any isotope of said element. Any formula given herein is also intended to represent isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorus, sulfur, fluorine, chlorine, and iodine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, $^{36}Cl$, and $^{125}I$.

When referring to any formula given herein, the selection of a particular moiety from a list of possible species for a specified variable is not intended to define the same choice of the species for the variable appearing elsewhere. In other words, where a variable appears more than once, the choice of the species from a specified list is independent of the choice of species for the same variable elsewhere in the formula, unless otherwise stated.

By way of a first example on substituent terminology, if substituent $S^1_{example}$ is one of $S_1$ and $S_2$, and substituent $S^2_{example}$ is one of $S_3$ and $S_4$, then these assignments refer to embodiments of this invention given according to the choices $S^1_{example}$ is $S_1$ and $S^2_{example}$ is $S_3$; $S^1_{example}$ is $S_1$ and $S^2_{example}$ is $S_4$; $S^1_{example}$ is $S_2$ and $S^2_{example}$ is $S_3$; $S^1_{example}$ is $S_2$ and $S^2_{example}$ is $S_4$; and equivalents of each one of such choices. The shorter terminology "$S^1_{example}$ is one of $S_1$ and $S_2$ and "$S^2_{example}$ is one of $S_3$ and $S_4$ is accordingly used herein for the sake of brevity but not by way of limitation. The foregoing first example on substituent terminology, which is stated in generic terms, is meant to illustrate the various substituent assignments described herein. The foregoing convention given herein for substituents extends, when applicable, to members such as $R^1$, $R^2$, $R^a$, $R^b$, $R^c$, $R^d$, $R^e$ and Y and any other generic substituent symbol used herein.

Furthermore, when more than one assignment is given for any member or substituent, embodiments of this invention comprise the various groupings that can be made from the listed assignments, taken independently, and equivalents thereof. By way of a second example on substituent terminology, if it is herein described that substituent $S_{example}$ is one of $S_1$, $S_2$ and $S_3$, the listing refers to embodiments of this invention for which $S_{example}$ is $S_1$; $S_{example}$ is $S_2$; $S_{example}$ is $S^3$; $S_{example}$ is one of $S_1$ and $S_2$; $S^3_{example}$ is one of $S_1$ and $S_3$; $S_{example}$ is one of $S_2$ and $S_3$; $S_{example}$ is one of $S_1$, $S_2$ and $S_3$; and $S_{example}$ is any equivalent of each one of these choices. The shorter terminology "$S_{example}$ is one of $S_1$, $S_2$ and $S_3$" is accordingly used herein for the sake of brevity, but not by way of limitation. The foregoing second example on substituent terminology, which is stated in generic terms, is meant to illustrate the various substituent assignments described herein. The foregoing convention given herein for substituents extends, when applicable, to members such as $R^1$, $R^2$, $R^a$, $R^b$, $R^c$, $R^d$, $R^e$ and Y and any other generic substituent symbol used herein.

The nomenclature "$C_{1-j}$" with j>i, when applied herein to a class of substituents, is meant to refer to embodiments of this invention for which each and every one of the number of carbon members, from i to j including i and j, is independently realized. By way of example, the term $C_{1-3}$ refers independently to embodiments that have one carbon member ($C_1$), embodiments that have two carbon members ($C_2$), and embodiments that have three carbon members ($C_3$).

The term $C_{n-m}$alkyl refers to an aliphatic chain, whether straight or branched, with the total number N of carbon members in the chain that satisfies n≤N≤m, with m>n.

Any disubstituent referred to herein is meant to encompass the various attachment possibilities when more than one of such possibilities are allowed. For example, reference to disubstituent -A-B—, where A≠B, refers herein to such disubstituent with A attached to a first substituted member and B attached to a second substituted member, and it also refers to such disubstituent with A attached to the second member and B attached to the first substituted member.

According to the foregoing interpretive considerations on assignments and nomenclature, it is understood that explicit reference herein to a set implies, where chemically meaningful and unless indicated otherwise, independent reference to embodiments of such set, and reference to each and every one of the possible embodiments of subsets of the set referred to explicitly.

The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)).

A "pharmaceutically acceptable prodrug" is a prodrug that is preferably non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

A "metabolite" means a pharmacologically active product of metabolism in the body of a compound of Formula (I) or salt thereof. Preferably, the metabolite is in an isolated form outside the body.

Compositions

The term "composition," as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation, or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of Formula (I) and a pharmaceutically acceptable excipient.

The term "pharmaceutically acceptable," as used in connection with compositions of the invention, refers to molecular entities and other ingredients of such compositions that are physiologically tolerable and do not typically produce untoward reactions when administered to an animal (e.g., human). The term "pharmaceutically acceptable" may also mean approved by a regulatory agency of the Federal or a state government or listed in the U.S. Pharmacopeia or other generally recognized pharmacopeia for use in animals (e.g. mammals), and more particularly in humans.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluents to facilitate administration of an agent and that is compatible therewith. Examples of excipients include calcium carbonate, calcium phosphate, various sugars and types of starch, cellulose derivatives, gelatin, vegetable oils, and polyethylene glycols. Suitable pharmaceutical carriers include those described in Remington: The Science and Practice of Pharmacy, 21$^{st}$ Ed., Lippincott Williams & Wilkins (2005).

A "pharmaceutically acceptable salt" is intended to mean a salt of a free acid or base of a compound represented by Formula (I) that is non-toxic, biologically tolerable, or otherwise biologically suitable for administration to the subject. See, generally, G. S. Paulekuhn et al., Trends in Active Pharmaceutical Ingredient Salt Selection based on Analysis of the Orange Book Database, *J. Med. Chem.* 2007, 50, 6665-6672; Berge et al., Pharmaceutical Salts, *J. Pharm. Sci.* 1977, 66, 1-19; Stahl and Wermuth (eds), Pharmaceutical Salts; Properties, Selection, and Use: 2nd Revised Edition, Wiley-VCS, Zurich, Switzerland (2011). Examples of pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt bases, and inorganic and organic acids, to form a pharmaceutically acceptable salt.

The term "carrier" refers to an adjuvant, vehicle, or excipients, with which the compound is administered. In preferred embodiments of this invention, the carrier is a solid carrier. Suitable pharmaceutical carriers include those described in Remington: The Science and Practice of Pharmacy, 21$^{st}$ Ed., Lippincott Williams & Wilkins (2005).

The term "dosage form," as used herein, is the form in which the dose is to be administered to the subject or patient. The drug is generally administered as part of a formulation that includes nonmedical agents. The dosage form has unique physical and pharmaceutical characteristics. Dosage forms, for example, may be solid, liquid or gaseous. "Dosage forms" may include, for example, a capsule, tablet, caplet, gel caplet (gelcap), syrup, a liquid composition, a powder, a concentrated powder, a concentrated powder admixed with a liquid, a chewable form, a swallowable form, a dissolvable form, an effervescent, a granulated form, and an oral liquid solution. In a specific embodiment, the dosage form is a solid dosage form, and more specifically, comprises a tablet or capsule.

As used herein, the term "inert" refer to any inactive ingredient of a described composition. The definition of "inactive ingredient" as used herein follows that of the U.S. Food and Drug Administration, as defined in 21 C.F.R. 201.3(b)(8), which is any component of a drug product other than the active ingredient.

Methods and Uses

As used herein, the term "disorder" is used interchangeably with "disease" or "condition". For example, a CNS disorder also means a CNS disease or a CNS condition.

As used herein, the term "cognitive impairment" is used interchangeably with "cognitive dysfunction" or "cognitive deficit," all of which are deemed to cover the same therapeutic indications.

The terms "treating," "treatment," and "treat" cover therapeutic methods directed to a disease-state in a subject and include: (i) preventing the disease-state from occurring, in particular, when the subject is predisposed to the disease-state but has not yet been diagnosed as having it; (ii) inhibiting the disease-state, e.g., arresting its development (progression) or delaying its onset; and (iii) relieving the disease-state, e.g., causing regression of the disease state until a desired endpoint is reached. Treating also includes ameliorating a symptom of a disease (e.g., reducing the pain, discomfort, or deficit), wherein such amelioration may be directly affecting the disease (e.g., affecting the disease's cause, transmission, or expression) or not directly affecting the disease.

As used in the present disclosure, the term "effective amount" is interchangeable with "therapeutically effective amount" and means an amount or dose of a compound or composition effective in treating the particular disease, condition, or disorder disclosed herein, and thus "treating" includes producing a desired preventative, inhibitory, relieving, or ameliorative effect. In methods of treatment according to the invention, "an effective amount" of at least one compound according to the invention is administered to a subject (e.g., a mammal). An "effective amount" also means an amount or dose of a compound or composition effective to modulate activity of MAO-B or an associated signaling pathway, such as the CREB pathway and thus produce the desired modulatory effect. The "effective amount" will vary, depending on the compound, the disease, the type of treatment desired, and its severity, and age, weight, etc.

The term "animal" is interchangeable with "subject" and may be a vertebrate, in particular, a mammal, and more particularly, a human, and includes a laboratory animal in the context of a clinical trial or screening or activity experiment. Thus, as can be readily understood by one of ordinary skill in the art, the compositions and methods of the present invention are particularly suited to administration to any vertebrate, particularly a mammal, and more particularly, a human.

As used herein, a "control animal" or a "normal animal" is an animal that is of the same species as, and otherwise comparable to (e.g., similar age, sex), the animal that is trained under conditions sufficient to induce transcription-dependent memory formation in that animal.

By "enhance," "enhancing" or "enhancement" is meant the ability to potentiate, increase, improve or make greater or better, relative to normal, a biochemical or physiological action or effect. For example, enhancing long term memory formation refers to the ability to potentiate or increase long term memory formation in an animal relative to the normal long term memory formation of the animal or controls. As a result, long term memory acquisition is faster or better retained. Enhancing performance of a cognitive task refers to the ability to potentiate or improve performance of a specified cognitive task by an animal relative to the normal performance of the cognitive task by the animal or controls.

As used herein, the term "training protocol," or "training," refers to either "cognitive training" or "motor training." The phrase "in conjunction" means that a compound or composition of the present invention enhances CREB pathway function during cognitive or motor training.

Reference will now be made to the embodiments of the present invention, examples of which are illustrated by and described in conjunction with the accompanying drawings and examples. While certain embodiments are described herein, it is understood that the described embodiments are not intended to limit the scope of the invention. On the contrary, the present disclosure is intended to cover alternatives, modifications, and equivalents that can be included within the invention as defined by the appended claims.

Compounds

The present invention provides disubstituted 1,5-naphthyridine and quinoline compounds, which are useful as inhibitors or monoamine oxidase, and monoamine oxidase B specifically. They are distinct from thiazolidine substituted quinoline compounds, which have been reported for treating diabetes (International Publication No. WO2003057216, Jul. 17, 2003), lowering visceral fat (International Publication No. WO9820871, May 22, 1998), and reducing blood sugar levels (International Publication No. WO9612710, May 2, 1996). They are also distinct from substituted quinoline compounds reported for treating diabetes (JP2002322163, Nov. 8, 2002; International Publication No. WO9828254, Jul. 2, 1998).

In its many embodiments, the invention is directed to a chemical entity of Formula

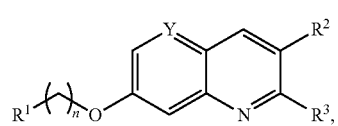

(I)

wherein
$R^1$, $R^2$, $R^3$, Y, and n have any of the values described herein.

In its many embodiments, the invention is directed to a chemical entity of Formula (I):
n is 0, 1, 2, or 3;
Y is CH or N;
$R^1$ is a pyridine substituted with $C_{1-6}$haloalkyl or an aryl substituted with one, two, or three $R^a$ members;

each $R^a$ is independently selected from the group consisting of halo, —$C_1$-$C_6$alkyl, —$C_{1-6}$haloalkyl, —$NO_2$, and —$OC_{1-6}$alkyl;
$R^2$ is selected from the group consisting of —$C(R^b)_2R^c$ or —CO—$R^d$;
each $R^b$ is selected from the group consisting of —H, —F, and —$C_{1-6}$alkyl, or optionally two $R^b$ members are taken together with the carbon to which they are attached to form a $C_{3-8}$cycloalkyl ring;
$R^c$ is selected from the group consisting of -halo, —$NH_2$, —OH, —$OC_{1-6}$alkyl, —$CH_2OH$, —CN, —CO—$NHR^e$, and —$C(CH_3)_2OH$; provided that when at least one $R^b$ is —F then $R^c$ is not —F;
$R^d$ is selected from the group consisting of -alkyl, —$OC_{1-6}$alkyl, —$NHR^e$, and —$NHCH_2CH_2N(R^e)_2$;
each $R^e$ is independently —H and —$C_{1-6}$alkyl; and
$R^3$ is selected from the group consisting of —H, —$C_{1-6}$alkyl, —OH, —$OC_{1-6}$alkyl, and $C_{1-6}$haloalkyl.

In a specific aspect, a compound, or a pharmaceutically acceptable salt thereof, of Formula (I) corresponding to the first embodiment may include one or more the following: n is 1, 2 or 3; Y is CH or N; $R^1$ is a pyridine substituted with $C_{1-4}$haloalkyl or an aryl substituted with 1, 2, or 3 $R^a$ members; each $R^a$ is independently selected from the group consisting of halo, —$C_{1-4}$alkyl, —$C_{1-4}$haloalkyl, —$NO_2$, and —$OC_{1-4}$alkyl; $R^2$ is —$C(R^b)_2R^c$ or —CO—$R^d$; each $R^b$ is independently selected from the group consisting of —H, —F, and —$C_{1-4}$alkyl, or optionally two $R^b$ members are taken together with the carbon to which they are attached to form a $C_{3-8}$cycloalkyl ring; $R^c$ is selected from the group consisting of -halo, —$NH_2$, —OH, —$OC_{1-4}$alkyl, —$CH_2OH$, —CN, —$CO_2$—$C_{1-4}$alkyl, —CO—$NHR^e$, and —$C(CH_3)_2OH$; provided that when at least one $R^b$ is —F then $R^c$ is not —F; $R^d$ is selected from the group consisting of -alkyl, —$OC_{1-4}$alkyl, —$NHR^e$, and —$NHCH_2CH_2N(R^e)_2$; each $R^e$ is independently —H or —$C_{1-4}$alkyl; and $R^3$ is selected from the group consisting of —H, —$C_{1-4}$alkyl, —OH, —$OC_{1-4}$alkyl, and $C_1$-$C_4$haloalkyl.

In a second embodiment of a compound, or a pharmaceutically acceptable salt thereof, of Formula (I),
n is 0, 1, or 2;
Y is CH or N;
$R^1$ is a pyridine substituted with —$CF_3$, or a phenyl substituted in the meta or para positions with one, two, or three $R^a$ members;
each $R^a$ is independently selected from the group consisting of halo, —$C_{1-6}$alkyl, —$C_{1-6}$haloalkyl, —$NO_2$, and —$OC_{1-4}$alkyl;
$R^2$ is selected from the group consisting of —$C(R^b)_2R^c$ or —CO—$R^d$;
each $R^b$ is independently selected from the group consisting of —H, —F, and —$C_{1-6}$alkyl, or optionally two $R^b$ members are taken together with the carbon to which they are attached to form a $C_{3-8}$cycloalkyl ring;
$R^c$ is selected from the group consisting of —F, —$NH_2$, —OH, —$OC_{1-3}$alkyl, —$CH_2OH$, —CN, —$CO_2$—$C_{1-6}$alkyl, —CO—$NHR^e$, and —$C(CH_3)_2OH$; provided that when at least one $R^b$ is —F then $R^c$ is not —F;
$R^d$ is selected from the group consisting of —$CH_3$, —$OC_{1-4}$ alkyl, —$NHR^e$, and —$NHCH_2CH_2N(R^e)_2$;
each $R^e$ is independently —H or —$CH_3$; and
$R^3$ is selected from the group consisting of —H, —$CH_3$, —OH, and —$CF_3$.

In a specific aspect, a compound, or a pharmaceutically acceptable salt thereof, of Formula I corresponding to the second embodiment may include one or more the following: n=1 or 2; Y is CH or N; $R^1$ is a pyridine substituted with —CF₃, or a phenyl substituted in the meta or para positions with one, two, or three $R^a$ members; $R^a$ is independently selected from the group consisting of halo, —C₁₋₄alkyl, CF₃, —NO₂, and —OC₁₋₄alkyl; $R^2$ is selected from the group consisting of —C($R^b$)₂$R^c$ or —CO—$R^d$; each $R^b$ is independently selected from the group consisting of —H, —F, and —C₁₋₃alkyl, or optionally two $R^b$ members are taken together with the carbon to which they are attached to form a C₃₋₆cycloalkyl ring; $R^c$ is selected from the group consisting of: —F, —NH₂, —OH, —OC₁₋₃alkyl, —CH₂OH, —CN, —CO₂—C₁₋₄alkyl, —CO—NHR$^e$, and —C(CH₃)₂OH; provided that when at least one $R^b$ is —F then $R^c$ is not —F; $R^d$ is selected from the group consisting of —CH₃, —OC₁₋₄alkyl, —NHR$^e$, and —NHCH₂CH₂N($R^e$)₂; each $R^e$ is independently —H or —CH₃; and $R^3$ is a member selected from the group consisting of —H, —CH₃, —OH, and —CF₃.

In a third embodiment of a compound, or a pharmaceutically acceptable salt thereof, of Formula (I), n is 1 or 2;
Y is CH or N;
$R^1$ is a pyridine substituted with —CF₃, or a phenyl substituted in the meta or para positions with one, two, or three $R^a$ members;
  each $R^a$ is independently selected from the group consisting of halo, —C₁₋₆alkyl, —C₁₋₆haloalkyl, OC₁₋₆alkyl CF₃, —NO₂, and _;
$R^2$ is selected from the group consisting of —C($R^b$)₂$R^c$ or —CO—$R^d$;
  each $R^b$ is independently selected from the group consisting of —H, —F, —C₁₋₆alkyl, or optionally two $R^b$ members are taken together with the carbon to which they are attached to form a C₃₋₈cycloalkyl ring;
  $R^c$ is selected from the group consisting of: —F, —NH₂, —OH, —OC₁₋₃alkyl, —CH₂OH, —CN, —CO₂—C₁₋₄alkyl, —CO—NHR$^e$, and —C(CH₃)₂OH; provided that provided that when at least one $R^b$ is —F then $R^c$ is not —F;
  $R^d$ is selected from the group consisting of: —CH₃, —OC₁₋₆ alkyl, —NHR$^e$, and —NHCH₂CH₂N($R^e$)₂;
  each $R^e$ is independently selected from the group consisting of —H and —CH₃; and
  $R^3$ is selected from the group consisting of —H, —CH₃, —OH, and —CF₃.

In a specific aspect, a compound, or a pharmaceutically acceptable salt thereof, of Formula I corresponding to the third embodiment may include one or more the following: n is 1 or 2; $R^2$ is selected from the group consisting of —C($R^b$)₂$R^c$ or —CO—$R^d$; $R^b$ is selected from the group consisting of —H, —F, —C₁₋₄alkyl, or optionally two $R^b$ members are taken together with the carbon to which they are attached to form a C₃₋₆cycloalkyl ring; $R^c$ is selected from the group consisting of: -halo, —NH₂, —OH, —CH₂OH, —CN, —CO—NHR$^e$, and —C(CH₃)₂OH; provided that when at least one $R^b$ is —F then $R^c$ is not —F; $R^d$ is selected from the group consisting of: -alkyl, —OC₁₋₄alkyl, —NHR$^e$, and —NHCH₂CH₂N($R^e$)₂; each $R^e$ is independently selected from the group consisting of —H and —C₁₋₄alkyl; and $R^3$ is selected from the group consisting of —H, —OH, —OC₁₋₄alkyl, and C₁-C₄haloalkyl.

In certain embodiments, n is 1.
In certain embodiments, n is 2.
In certain embodiments, Y is CH.
In certain embodiments, Y is N.
In some embodiments, $R^1$ is 2-(trifluoromethyl)pyridin-4-yl or 6-(trifluoromethyl)pyridin-2-yl.
In some embodiments, $R^1$ is phenyl substituted with $R^a$, and $R^a$ is halo, C₁₋₄alkyl, -C₁₋₄haloalkyl, —OC₁₋₄alkyl, or —NO₂.

In some embodiments, $R^1$ is 3-chlorophenyl, 3-fluorophenyl, 3-nitrophenyl, 3-methylphenyl, 3-methoxyphenyl, 3-(trifluoromethyl)phenyl, 3-chloro-4-fluorophenyl, 3,4-difluorophenyl, 3-chloro-5-fluorophenyl, 3,5-difluorophenyl, 3-fluoro-5-(trifluoromethyl)phenyl, 3,4,5-trifluorophenyl, 4-chlorophenyl, 4-fluorophenyl, 4-(trifluoromethyl)phenyl, 4-fluoro-3-(trifluoromethyl)phenyl, 4-nitrophenyl, 4-methoxyphenyl, 2-(trifluoromethyl)pyridin-4-yl, or 6-(trifluoromethyl)pyridin-2-yl.

In some embodiments, $R^2$ is —(C$R^b$)₂$R^c$, and n is 1.
In some embodiments, $R^b$ is —H, halo or —CH₃.
In some embodiments, two $R^b$ groups are taken together with the carbon to which they are attached to form a cyclopropyl, cyclobutyl, cyclopentyl, or cyclohexyl ring.
In some embodiments, $R^c$ is halo, —NH₂, —OH, —OCH₃, —CH₂OH, —CN, —CO₂—C₁₋₄alkyl, —CO—NHR$^e$, and —C(CH₃)₂OH.
In some embodiments, $R^2$ is —CH₂NH₂, —CH₂OH, —CH₂CH₂OH, —CH₂OCH₃, —CH₂CN, —CH₂(C=O)OCH₃, —CH₂(C=O)OCH₂CH₃, —CH₂(C=O)NH₂, —CH₂(CH₃)₂OH, —CH(OH)CH₃, —C(CH₃)₂OH, —C(CH₃)₂CH₂OH, —C(CH₃)₂(C=O)NH₂, —OCH₂CH₃, or —CF(CH₃)₂.
In some embodiments, $R^2$ is —CO—$R^d$, and n is 1.
In some embodiments, $R^d$ is —CH₃, —OC₁₋₄alkyl, —NH₂, —NH(CH₃), —NHCH₂CH₂NH(CH₃) or —NHCH₂CH₂N(CH₃)₂
In some embodiments, $R^2$ is —(C=O)CH₃, —C(=O)OCH₃, —C(=O)OCH₂CH₃, —(C=O)NH₂, —(C=O)NHCH₃, —(C=O)N(CH₃)₂, —(C=O)NHCH₂CH₂NH₂, —(C=O)NHCH₂CH₂NHCH₃, or —(C=O)NHCH₂CH₂N(CH₃)₂.
In certain embodiments, $R^3$ is H or —CH₃.
In certain embodiments, $R^3$ is —CF₃ or —OH.
In certain embodiments, $R^1$ is

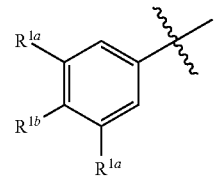

or

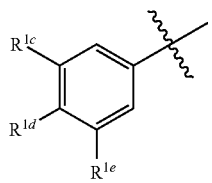

each $R^{1a}$ is independently selected from the group consisting of —H, halo, —C₁₋₄alkyl, CF₃, —NO₂, and —OC₁₋₄alkyl; $R^{1b}$ is selected from the group consisting of halo, —C₁₋₄alkyl, CF₃, —NO₂, and —OC₁₋₄alkyl; $R^{1c}$ is selected from the group consisting of halo, —C₁₋₄alkyl, CF₃, —NO₂, and —OC₁₋₄alkyl; $R^{1d}$ is selected from the group consisting of —H, halo, —C₁₋₄alkyl, CF₃, —NO₂, and —OC₁₋₄alkyl; and $R^{1e}$ is selected from the group consisting of —H, halo, —C₁₋₄alkyl, CF₃, —NO₂, and —OC₁₋₄alkyl.

Further embodiments are provided by pharmaceutically acceptable salts of compounds of Formula (I), pharmaceutically acceptable prodrugs of compounds of Formula (I), and pharmaceutically active metabolites of compounds of Formula (I).

In certain embodiments, a compound, or a pharmaceutically acceptable salt thereof, of Formula (I), is selected from the group consisting of:

| Example # | Compound Name |
|---|---|
| 1 | Ethyl 7-[(4-chlorophenyl)methoxy]quinoline-3-carboxylate; |
| 2 | Ethyl 7-[(4-fluorophenyl)methoxy]quinoline-3-carboxylate; |
| 3 | Ethyl 7-[(3-chlorophenyl)methoxy]quinoline-3-carboxylate; |
| 4 | Ethyl 7-[(3-fluorophenyl)methoxy]quinoline-3-carboxylate; |
| 5 | Ethyl 7-((3-(trifluoromethyl)benzyl)oxy)quinoline-3-carboxylate; |
| 6 | Ethyl 7-((4-(trifluoromethyl)benzyl)oxy)quinoline-3-carboxylate; |
| 7 | Ethyl 7-((3-methylbenzyl)oxy)quinoline-3-carboxylate; |
| 8 | Ethyl 7-((4-methylbenzyl)oxy)quinoline-3-carboxylate; |
| 9 | Ethyl 7-((3-methoxybenzyl)oxy)quinoline-3-carboxylate; |
| 10 | Ethyl 7-((4-methoxybenzyl)oxy)quinoline-3-carboxylate; |
| 11 | Ethyl 7-((4-nitrobenzyl)oxy)quinoline-3-carboxylate; |
| 12 | Ethyl 7-((4-fluoro-3-(trifluoromethyl)benzyl)oxy)quinoline-3-carboxylate; |
| 13 | Ethyl 7-((3-fluoro-5-(trifluoromethyl)benzyl)oxy)quinoline-3-carboxylate; |
| 14 | Ethyl 7-((3,4-difluorobenzyl)oxy)quinoline-3-carboxylate; |
| 15 | Ethyl 7-((3,5-difluorobenzyl)oxy)quinoline-3-carboxylate; |
| 16 | Ethyl 7-((3,4,5-trifluorobenzyl)oxy)quinoline-3-carboxylate; |
| 17 | Ethyl 7-((3-chloro-4-fluorobenzyl)oxy)quinoline-3-carboxylate; |
| 18 | Ethyl 7-((3-nitrobenzyl)oxy)quinoline-3-carboxylate; |
| 19 | Ethyl 7-((3-chloro-5-fluorobenzyl)oxy)quinoline-3-carboxylate; |
| 20 | Ethyl 7-((3-chlorobenzyl)oxy)-2-methylquinoline-3-carboxylate; |
| 21 | Ethyl 7-((3-fluorobenzyl)oxy)-2-methylquinoline-3-carboxylate; |
| 22 | Ethyl 7-((4-fluorobenzyl)oxy)-2-methylquinoline-3-carboxylate; |
| 23 | Ethyl 7-((3-chloro-4-fluorobenzyl)oxy)-2-methylquinoline-3-carboxylate; |
| 24 | Ethyl 7-(3-fluorophenethoxy)quinoline-3-carboxylate; |
| 25 | Ethyl 7-(3-chlorophenethoxy)quinoline-3-carboxylate; |
| 26 | Methyl 7-((3-chlorobenzyl)oxy)quinoline-3-carboxylate; |
| 27 | 2-(7-((4-Fluorobenzyl)oxy)quinolin-3-yl)propan-2-ol; |
| 28 | 2-(7-((3-Chlorobenzyl)oxy)quinolin-3-yl)propan-2-ol; |
| 29 | 2-(7-((3,5-Difluorobenzyl)oxy)quinolin-3-yl)propan-2-ol; |
| 30 | 2-(7-((3,4,5-Trifluorobenzyl)oxy)quinolin-3-yl)propan-2-ol; |
| 31 | 2-(7-((4-Fluorobenzyl)oxy)-2-methylquinolin-3-yl)propan-2-ol; |
| 32 | 2-(7-((3-Chlorobenzyl)oxy)-2-methylquinolin-3-yl)propan-2-ol; |
| 33 | 2-(7-((3-Chloro-4-fluorobenzyl)oxy)-2-methylquinolin-3-yl)propan-2-ol; |
| 34 | 2-(7-((3-Fluorobenzyl)oxy)-2-methylquinolin-3-yl)propan-2-ol; |
| 35 | (7-((3-Chlorobenzyl)oxy)quinolin-3-yl)methanol; |
| 36 | (7-((3,5-Difluorobenzyl)oxy)quinolin-3-yl)methanol; |
| 37 | (7-((3,4,5-Trifluorobenzyl)oxy)quinolin-3-yl)methanol; |
| 38 | 2-(7-(3-Fluorophenethoxy)quinolin-3-yl)propan-2-ol; |
| 39 | 2-(7-(3-Chlorophenethoxy)quinolin-3-yl)propan-2-ol; |
| 40 | 7-((3-Chlorobenzyl)oxy)-3-(methoxymethyl)quinoline; |
| 41 | 7-((4-Fluorobenzyl)oxy)-3-(2-fluoropropan-2-yl)quinoline; |
| 42 | 1-(7-((4-Fluorobenzyl)oxy)quinolin-3-yl)ethanone; |
| 43 | 1-(7-((4-Fluorobenzyl)oxy)quinolin-3-yl)ethanol; |
| 44 | (R)-1-(7-((4-Fluorobenzyl)oxy)quinolin-3-yl)ethanol; |
| 45 | (S)-1-(7-((4-Fluorobenzyl)oxy)quinolin-3-yl)ethanol; |
| 46 | 7-((3-Chlorobenzyl)oxy)-N-methylquinoline-3-carboxamide; |
| 47 | N-(2-Aminoethyl)-7-((3-chlorobenzyl)oxy)quinoline-3-carboxamide; |
| 48 | 7-((3-Chlorobenzyl)oxy)-N-(2-(methylamino)ethyl)quinoline-3-carboxamide; |
| 49 | 7-((3-Chlorobenzyl)oxy)-N-(2-(dimethylamino)ethyl)quinoline-3-carboxamide; |
| 50 | (7-((3-Chlorobenzyl)oxy)quinolin-3-yl)methanamine; |
| 51 | 2-(7-((3-Chlorobenzyl)oxy)quinolin-3-yl)acetamide; |
| 52 | Ethyl 2-(7-((3-fluorobenzyl)oxy)quinolin-3-yl)acetate; |
| 53 | Ethyl 2-(7-((4-fluorobenzyl)oxy)quinolin-3-yl)acetate; |
| 54 | Methyl 2-(7-((3-chlorobenzyl)oxy)quinolin-3-yl)acetate; |
| 55 | 2-(7-((3-Chlorobenzyl)oxy)quinolin-3-yl)acetamide; |
| 56 | 2-(7-((3-Chlorobenzyl)oxy)quinolin-3-yl)ethanol; |
| 57 | 2-(7-((3-Fluorobenzyl)oxy)quinolin-3-yl)acetamide; |
| 58 | 2-(7-((4-Fluorobenzyl)oxy)quinolin-3-yl)acetamide; |
| 59 | Ethyl 2-(7-((3-chlorobenzyl)oxy)quinolin-3-yl)-2-methylpropanoate; |
| 60 | 2-(7-((3-Chlorobenzyl)oxy)quinolin-3-yl)-2-methylpropan-1-ol; |
| 61 | 2-(7-((3-Chlorobenzyl)oxy)quinolin-3-yl)-2-methylpropanamide; |
| 62 | 2-(7-((2-(Trifluoromethyl)pyridin-4-yl)methoxy)quinolin-3-yl)acetamide; |
| 63 | 1-(7-((3-Chlorobenzyl)oxy)quinolin-3-yl)-2-methylpropan-2-ol; |
| 64 | 7-((3-Chlorobenzyl)oxy)quinoline-3-carboxamide; |
| 65 | 2-{7-[(4-Fluorophenyl)methoxy]-1,5-naphthyridin-3-yl}propan-2-ol; |
| 66 | 7-[(4-Fluorophenyl)methoxy]-3-(2-hydroxypropan-2-yl)quinolin-1-ium-1-olate; |
| 67 | 7-[(3-Fluorophenyl)methoxy]-1,5-naphthyridine-3-carboxamide; |
| 68 | 7-((4-Fluorobenzyl)oxy)-1,5-naphthyridine-3-carboxamide; |
| 69 | 7-((3-Chlorobenzyl)oxy)-1,5-naphthyridine-3-carboxamide; |

-continued

| Example # | Compound Name |
|---|---|
| 70 | 7-((3,4-Difluorobenzyl)oxy)-1,5-naphthyridine-3-carboxamide; |
| 71 | 7-[(3-Chloro-4-fluorophenyl)methoxy]-1,5-naphthyridine-3-carboxamide; |
| 72 | 7-[(3-Chlorophenyl)methoxy]-N-methyl-1,5-naphthyridine-3-carboxamide; |
| 73 | (7-((3,4-Difluorobenzyl)oxy)-1,5-naphthyridin-3-yl)methanol; |
| 74 | 2-{7-[(3,4-Difluorophenyl)methoxy]-1,5-naphthyridin-3-yl}acetonitrile; |
| 75 | 3-[(4-Fluorophenyl)methoxy]-7-(2-fluoropropan-2-yl)-1,5-naphthyridine; |
| 76 | 2-{7-[(3-Fluorophenyl)methoxy]-1,5-naphthyridin-3-yl}propan-2-ol; |
| 77 | 2-{7-[(3,4-Difluorophenyl)methoxy]-1,5-naphthyridin-3-yl}propan-2-ol; |
| 78 | 2-{7-[(3-Chloro-4-fluorophenyl)methoxy]-1,5-naphthyridin-3-yl}propan-2-ol; |
| 79 | 2-{7-[(3-Chlorophenyl)methoxy]-1,5-naphthyridin-3-yl}propan-2-ol; |
| 80 | 2-(7-((3,4-Difluorobenzyl)oxy)-1,5-naphthyridin-3-yl)acetamide; |
| 81 | 2-(7-((6-(Trifluoromethyl)pyridin-2-yl)methoxy)-1,5-naphthyridin-3yl)acetamide; |
| 82 | 2-(7-((3-Chlorobenzyl)oxy)-2-oxo-1,2,3,4-tetrahydroquinolin-3-yl)acetamide; and |
| 83 | 2-(7-((3-Chlorobenzyl)oxy)-2-oxo-1,2-dihydroquinolin-3-yl)acetamide. |

Isotopically-Labeled Compounds

The invention also includes isotopically-labeled compounds, which are identical to those recited in Formula I, but for the fact that one or more atoms are replaced by an atom having an atomic mass or mass number different from the atomic mass or mass number usually found in nature. Examples of isotopes that can be incorporated into compounds of the invention include isotopes of carbon, chlorine, fluorine, hydrogen, iodine, nitrogen, oxygen, phosphorous, sulfur, and technetium, including $^{11}C$, $^{13}C$, $^{14}C$, $^{36}Cl$, $^{18}F$, $^{2}H$, $^{3}H$, $^{123}I$, $^{125}I$, $^{13}N$, $^{15}N$, $^{15}O$, $^{17}O$, $^{18}O$, $^{31}P$, $^{32}P$, $^{35}S$, and $^{99m}Tc$.

Compounds of the present invention (and derivatives of such compounds, such as pharmaceutically acceptable salts and prodrugs) that contain the aforementioned isotopes or other isotopes of other atoms are within the scope of the invention. Isotopically-labeled compounds of the present invention are useful in drug and substrate tissue distribution and target occupancy assays. For example, isotopically labeled compounds are particularly useful in SPECT (single photon emission computed tomography) and in PET (positron emission tomography), as discussed further herein.

Derivatives

The present invention also provides derivatives of a chemical entity of Formula (I), which include, but are not limited to, a salt, solvate, conformer, or crystalline form/polymorph.

Salts

Accordingly, in one embodiment the invention includes pharmaceutically acceptable salts of the compounds represented by Formula (I), and methods using such salts.

Examples of pharmaceutically acceptable salts include sulfates, pyrosulfates, bisulfates, sulfites, bisulfites, phosphates, monohydrogen-phosphates, dihydrogenphosphates, metaphosphates, pyrophosphates, chlorides, bromides, iodides, acetates, borate, nitrate, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propane sulfonates, naphthalene-1-sulfonates, naphthalene-2-sulfonates, besylate, mesylate and mandelates.

When the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid, glutaric acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

When the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as N-methyl-O-glucamine, lysine, choline, glycine and arginine, ammonia, carbonates, bicarbonates, primary, secondary, and tertiary amines, and cyclic amines, such as tromethamine, benzylamines, pyrrolidines, piperidine, morpholine, and piperazine, and inorganic salts derived from sodium, calcium, potassium, magnesium, manganese, iron, copper, zinc, aluminum, and lithium.

Solvates

In other embodiments, the invention provides a solvate of a compound of Formula (I), and the use of such solvates in methods of present invention. Certain compounds of Formula (I) or pharmaceutically acceptable salts of compounds of Formula (I) may be obtained as solvates. In some embodiments, the solvent is water and the solvates are hydrates.

More particularly, solvates include those formed from the interaction or complexes of compounds of the invention with one or more solvents, either in solution or as a solid or crystalline form. Such solvent molecules are those commonly used in the pharmaceutical art, which are known to be innocuous to the recipient, e.g., water, ethanol, ethylene glycol, and the like. Other solvents may be used as intermediate solvates in the preparation of more desirable solvates, such as MeOH, methyl t-butyl ether, ethyl acetate, methyl acetate, (S)-propylene glycol, (R)-propylene glycol, 1,4-butyne-diol, and the like. Hydrates include compounds formed by an incorporation of one or more water molecules.

Conformers and Crystalline Forms/Polymorphs

In other embodiments, the invention provides conformer and crystalline form of a compound of Formula (I), and the use of these derivatives in methods of present invention. A conformer is a structure that is a conformational isomer. Conformational isomerism is the phenomenon of molecules with the same structural formula but different conformations (conformers) of atoms about a rotating bond.

A polymorph is a composition having the same chemical formula, but a different solid state or crystal structure. In certain embodiments of the invention, compounds of Formula (I) were obtained in crystalline form. In addition, certain crystalline forms of compounds of Formula (I) or pharmaceutically acceptable salts of compounds of Formula (I) may be obtained as co-crystals. In still other embodiments, compounds of Formula (I) may be obtained in one of several polymorphic forms, as a mixture of crystalline forms, as a polymorphic form, or as an amorphous form.

Prodrugs

The invention also relates to prodrugs of the compounds of Formula (I), and the use of such pharmaceutically acceptable prodrugs in methods of the present invention, particularly therapeutic methods. Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-6}$alkyl, $C_{1-6}$cycloalkyl, phenyl, and phenyl($C_{1-6}$ alkyl)esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in Fleisher et al., *Adv. Drug Delivery Rev.* 1996, 19, 115-130.

Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in Robinson et al., *J. Med. Chem.* 1996, 39, 10-18. Free amines can also be derivatized as amides, sulfonamides or phosphonamides. All of these prodrug moieties may incorporate groups including ether, amine, and carboxylic acid functionalities.

Prodrugs may be determined using routine techniques known or available in the art (e.g., Bundgard (ed.), 1985, Design of prodrugs, Elsevier; Krogsgaard-Larsen et al., (eds.), 1991, Design and Application of Prodrugs, Harwood Academic Publishers).

Metabolites

The present invention also relates to a metabolite of a compound of Formula (I), as defined herein, and salts thereof. The present invention further relates to the use of such metabolites, and salts thereof, in methods of present invention, including therapeutic methods.

Metabolites of a compound may be determined using routine techniques known or available in the art. For example, isolated metabolites can be enzymatically and synthetically produced (e.g., Bertolini et al., *J. Med. Chem.* 1997, 40, 2011-2016; Shan et al., *J. Pharm. Sci.* 1997, 86, 765-767; Bagshawe, *Drug Dev. Res.* 1995, 34, 220-230; and Bodor, Adv Drug Res. 1984, 13, 224-231).

Compositions

In some embodiments Compounds of Formula (I) and pharmaceutically acceptable salts thereof are used, alone or in combination with one or more additional active ingredients, to formulate pharmaceutical compositions. A pharmaceutical composition of the invention comprises: (a) an effective amount of at least one active agent in accordance with the invention; and (b) a pharmaceutically acceptable excipient.

Formulations and Administration

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Osol, ed.), 1980, 1553-1593.

Any suitable route of administration may be employed for providing an animal, especially a human, with an effective dosage of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like.

Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent, or excipient used will depend upon the means and purpose for which the compound of the present invention is being applied. Solvents are generally selected based on solvents recognized by persons skilled in the art as safe (GRAS) to be administered to an animal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., a compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable and appropriate dosage of the drug.

The pharmaceutical composition (or formulation) for application may be packaged in a variety of ways, depending upon the method used to administer the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are typically prepared by incorporating the active compound in the required amount in the appropriate solvent with a variety of the other ingredients enumerated above, as required, followed by filter sterilization. In the case of sterile powders for the preparation of sterile injectable solutions, common methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina, and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Dosages

Useful dosages of the compounds of Formula (I) can be determined by comparing their in vitro activity and in vivo activity in animal models. Methods for the extrapolation of effective dosages in mice, and other animals, to humans are known to the art. Useful dosages of the compounds of formula I can be determined by comparing their in vitro activity, and in vivo activity in animal models. Methods for the extrapolation of effective dosages in mice, and other animals, to humans are known to the art (e.g., U.S. Pat. No. 4,938,949). Useful dosages of MAO-B inhibitors are known to the art (e.g., U.S. 2007-0203154, U.S. 2011-0160248, U.S. 2010-0317648, and U.S. Pat. No. 8,222,243).

Optimal dosages to be administered in the therapeutic methods of the present invention may be determined by those skilled in the art and will depend on multiple factors, including the particular composition in use, the strength of the preparation, the mode and time of administration, and the advancement of the disease or condition. Additional factors may include characteristics on the subject being treated, such as age, weight, gender, and diet.

In general, however, a suitable dose will be in the range from about 0.01 to about 100 mg/kg, more specifically, from about 0.1 to about 100 mg/kg, such as 10 to about 75 mg/kg of body weight per day, 3 to about 50 mg per kilogram body weight of the recipient per day, 0.5 to 90 mg/kg/day, or 1 to 60 mg/kg/day (or any other value or range of values therein). The compound is conveniently administered in a unit dosage form; for example, containing about 1 to 1000 mg, particularly about 10 to 750 mg, and more particularly, about 50 to 500 mg of active ingredient per unit dosage form.

Preferably, the active ingredient should be administered to achieve peak plasma concentrations of the active compound of from about 0.5 to about 75 μM, preferably, about 1 to 50 μM, and more preferably, about 2 to about 30 μM. This may be achieved, for example, by the intravenous injection of a 0.05 to 5% solution of the active ingredient, optionally in saline, or orally administered as a bolus containing about 1 to 100 mg of the active ingredient. Desirable blood levels may be maintained by continuous infusion to provide about 0.01 to 5.0 mg/kg/hr or by intermittent infusions containing about 0.4 to 15 mg/kg of the active ingredient(s).

The desired dose may conveniently be presented in a single dose or as divided doses administered at appropriate intervals, for example, as two, three, four or more sub-doses per day. The sub-dose itself may be further divided, e.g., into a number of temporally-distinct administrations used according to the compositions and methods of the present invention.

Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. Such compositions and preparations should contain at least 0.1% of active compound. The percentage of the compositions and preparations may, of course, be varied and may conveniently be between 2 to about 60% of the weight of a given unit dosage form. The amount of active compound in such therapeutically useful composition is such that an effective dosage level will be obtained. An exemplary dose is in the range from about 0.001 to about 200 mg of active agent per kg of subject's body weight per day, preferably about 0.05 to 100 mg/kg/day, or about 1 to 35 mg/kg/day, or about 0.1 to 10 mg/kg/daily in single or divided dosage units (e.g., BID, TID, QID). For a 70-kg human, an illustrative range for a suitable dosage amount is from 1 to 200 mg/day, or about 5 to 50 mg/day.

Methods and Uses

Uses of Isotopically-Labeled Compounds

In one aspect, the present invention provides a method of using isotopically labeled compounds and prodrugs of the present invention in: (i) metabolic studies (preferably with $^{14}C$), reaction kinetic studies (with, for example $^{2}H$ or $^{3}H$); (ii) detection or imaging techniques [such as positron emission tomography (PET) or single-photon emission computed tomography (SPECT)] including drug or substrate tissue distribution assays; or (iii) in radioactive treatment of patients.

Isotopically labeled compounds and prodrugs of the invention thereof can generally be prepared by carrying out the procedures disclosed in the schemes or in the examples and preparations described below by substituting a readily available isotopically labeled reagent for a non-isotopically labeled reagent. An $^{18}F$ or $^{11}C$ labeled compound may be particularly preferred for PET, and an $I^{123}$ labeled compound may be particularly preferred for SPECT studies. Further substitution with heavier isotopes such as deuterium (i.e., $^{2}H$) may afford certain therapeutic advantages resulting from greater metabolic stability, for example increased in vivo half-life or reduced dosage requirements.

Therapeutic Methods

Generally

In certain embodiments the present invention provides therapeutic methods of using a compound of Formula (I) and its pharmaceutically acceptable salts, pharmaceutically acceptable prodrugs, and pharmaceutically active metabolites, whether alone or in combination (collectively, "active agents") of the present invention are useful as inhibiting MAO in the methods of the invention. Such methods for inhibiting MAO, comprising administering to an animal an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I). Embodiments of this invention inhibit MAO. The invention further includes the use of such compounds and compositions thereof in the methods described herein. In one aspect of such methods disclosed herein, the animal is healthy. In another aspect of such methods, the animal has a disorder. In another aspect of all such methods the animal is an aged animal. In preferred embodiments the animal in such methods is a human.

In one aspect, such chemical entities are useful as inhibitors of monoamine oxidase, and monoamine oxidase type B selectively. Accordingly, the present invention provides a method for inhibiting MAO, comprising administering to an animal an effective amount of a chemical entity of Formula (I) or composition thereof.

Chemical entities of the present invention may be administered as a monotherapy or as part of a combination therapy. In one aspect, one or more of the compounds (or salts, produgs, or metabolites thereof) of the present invention may be co-administered or used in combination with one or more additional therapies known in the art. For example, compounds of the present invention may be used as adjunct therapy with dopamine preparations, dopamine agonists, or COMT agents (drugs that inhibit the action of catechol-methyl transferase) for the treatment of Parkinson's disease. As another example, targeting both monoamine oxidase-B inhibition and iron chelation can confer superior neuroprotection against Parkinson's disease and other neurodegenerative disorders (e.g., Youdim et al., *J. Neural. Transm.* 2004, 111, 1455-1471).

The present invention also includes methods of treating a disease, disorder, or condition mediated by MAO. Accordingly, in one embodiment, the invention provides a method of treating a disorder mediated by MAO, and MAO-B in particular, comprising administering to an animal in need of such treatment an effective amount of a chemical entity of Formula (I) or composition of the present invention.

In certain embodiments, the present invention includes the use of a chemical entity of Formula (I) in the manufacture of a medicament for treating a disease, condition, or disorder by inhibiting MAO-B. The present invention further provides a method of administering a therapeutically effective amount of a medicament of the present invention to a patient in need of such treatment to treat the disorder.

In one aspect, the compounds of the present invention are useful in enhancing neuronal plasticity—an essential property of the brain that can be augmented in healthy animals and can be impaired in numerous CNS disorders. For example, by inhibiting MAO-B activity, a compound of the present invention may enhance levels of $Ca^{2+}$ and cAMP/cGMP, triggering a signaling cascade that ultimately activates transcription factors, including the cAMP responsive element binding protein (CREB). CREB activation can then increase expression of neuronal plasticity-related genes, neurotrophic factors, and neuroprotective molecules—which in turn can promote the functional and morphological changes necessary for neuronal plasticity to occur (e.g., Tully et al., *Nat. Rev. Drug. Discov.* 2003, 2, 267-277; and Alberini, *Physiol. Rev.* 2009, 89, 121-145). Indeed, compounds of the present invention have been shown to activate CREB in cell-based assays. Accordingly, the present invention provides a method of enhancing neuronal plasticity, comprising administering to an animal in need thereof an effective amount of a chemical entity or composition of the present invention.

In another embodiment, the present invention provides a method of treating a disease mediated by MAO, comprising administering to an animal in need of such treatment an effective amount of a compound or composition of the present invention. MAO-B related indications that can be treated by compounds and compositions of the present invention include, but are not limited to neurological disorders, endocrine or metabolic disorders; and other disorders involving MAO-B signaling.

Chemical entities and compositions of the present invention are also useful as neuroprotective agents, as described in greater detail herein. Accordingly, the present invention provides a method of neuroprotection, comprising administering to an animal in need thereof an effective amount of at least one chemical entity or composition of the present invention.

Chemical entities and compositions of the present invention are also useful as agents in neurorehabilitation and neurorecovery, as described in greater detail herein. Accordingly, the present invention provides a method of neurorehabilitation or neurorecovery, comprising administering to an animal in need thereof an effective amount of at least one chemical entity or composition of the present invention.

In addition, such compounds can be administered in conjunction with training protocols to treat cognitive or motor deficits associated with CNS disorders, as described in more detail herein. In addition, such compounds can be used to enhance the efficiency of training protocols in non-human animals, in particular healthy non-human animals, as described herein.

Neurological Disorders

In some embodiments, the present invention provides a method of treating a neurological disorder, comprising administering to an animal in need of such treatment an effective amount of a compound or composition described herein.

A neurological disorder (or condition or disease) is any disorder of the body's nervous system. Neurological disorders can be categorized according to the primary location affected, the primary type of dysfunction involved, or the primary type of cause. The broadest division is between central nervous system (CNS) disorders and peripheral nervous system (PNS) disorders.

Neurological disorders include structural, biochemical, or electrical abnormalities in the brain, spinal cord or other nerves, abnormalities that can result in a range of symptoms. Examples of such symptoms include paralysis, muscle weakness, poor coordination, loss of sensation, seizures, confusion, pain, altered levels of consciousness, and cognitive deficits, including memory impairments. There are many recognized neurological disorders, some relatively common, but many rare. They may be assessed by neurological examination, and studied and treated within the specialties of neurology and clinical neuropsychology.

Neurological disorders and their sequelae (direct consequences) affect as many as one billion people worldwide, as estimated by the World Health Organization in 2006. Interventions for neurological disorders may include, in addition to medications, preventative measures, lifestyle changes, physiotherapy or other therapies, neurorehabilitation, pain management, and surgery.

Neurological disorders include, but are not limited to the following (which are not necessarily mutually exclusive): psychiatric disorders, such as mood disorders, psychotic disorders, and anxiety disorders; personality disorders; substance-related disorders; dissociative disorders; eating disorders; sleep disorders; developmental disorders; neurodegenerative disorders, including movement disorders; trauma-related disorders; pain disorders; and cognitive disorders, a category that includes memory disorders such as AAMI and MCI, as well as cognitive deficits (particularly memory deficits) associated with CNS disorders.

Psychiatric Disorders

In one embodiment, the invention provides a method of treating a psychiatric disorder, comprising administering to an animal in need of such treatment an effective amount of a compound or pharmaceutical composition described herein. Psychiatric disorders include mood (or affective) disorders, psychotic disorders, and anxiety (or neurotic) disorders (e.g., Liebowitz et al., "Reversible and irreversible monoamine oxidase inhibitors in other psychiatric disorders", *Acta. Psychiatr. Scand. Suppl.* 1990, 360, 29-34.

Mood Disorders

In some embodiments, the psychiatric disorder is a mood (or affective) disorder. Accordingly, the present invention provides a method of treating a mood disorder, comprising administering to an animal in need of such treatment an effective amount of a compound or pharmaceutical composition described herein. In a specific aspect, the mood disorder is a depressive disorder, including a dysthymic disorder, major depressive disorder (recurrent and single episode), mania, bipolar disorders (I and II), and cyclothymic disorder. Long-standing research underscores a role for MAO in mood disorders, including depressive disorders, bipolar disorders, and substance induced mood disorders is known in the literature (e.g., Gutierrez B, et al., "Association analysis between a functional polymorphism in the monoamine oxidase A gene promoter and severe mood disorders", *Psychiatr. Genet.* 2004, 14, 203-208; Duncan et al., "Monoamine oxidases in major depressive disorder and alcoholism", *Drug Discover. Ther.* 2012, 6, 112-122.

A specific embodiment of the invention is a method of treating a substance induced mood disorder, comprising administering to an animal in need of such treatment a therapeutically effective amount of a compound or pharmaceutical composition described herein. The utility of MAO inhibitors in the treatment of substance induced mood disorders is known in the literature (e.g., Takahashi et al., "Monoamine oxidase activity in blood platelets in alcoholism." *Folia. Psychiatr. Neurol. Jpn.* 1976, 30, 455-462).

Psychotic Disorders

In some embodiments, the psychiatric disorder is a psychotic disorder. Accordingly, the present invention provides a method of treating a psychotic disorder, comprising an animal in need of such treatment an effective amount of a compound or pharmaceutical composition described herein. In a specific aspect, the psychotic disorder is one or more of the following: schizophrenia; schizophreniform disorder; schizoaffective disorder; delusional disorder; brief psychotic disorder; shared psychotic disorder; substance-induced psychotic disorders, such as a psychosis induced by alcohol, amphetamine, cannabis, cocaine, hallucinogens, inhalants, opioids, or phencyclidine; and personality disorders at times of stress (including paranoid personality disorder, schizoid personality disorder, and borderline personality disorder).

A specific embodiment of the invention is a method of treating a delusional disorder, comprising administering to an animal in need of such treatment a therapeutically effective amount of a compound or pharmaceutical composition described herein. The utility of MAO inhibitors in the treatment of delusional disorders is known in the literature (e.g., DeVane and Mintzer, "Risperidone in the management of psychiatric and neurodegenerative disease in the elderly: an update", *Psychopharmacol. Bull.* 2003, 37, 116-132.

A particular embodiment of the invention is a method of treating schizophrenia, comprising administering to an animal in need of such treatment a therapeutically effective amount of a compound or pharmaceutical composition described herein. The utility of MAO inhibitors in the treatment of schizophrenia, including schizophreniform disorder and schizoaffective disorder, is known in the literature (e.g., Toren et al., "Benefit-risk assessment of atypical antipsychotics in the treatment of schizophrenia and comorbid disorders in children and adolescents", *Drug Saf.* 2004, 27, 1135-1156).

Anxiety Disorders

In some embodiments, the psychiatric disorder is an anxiety (or neurotic) disorder. Accordingly, the present invention provides a method of treating an anxiety disorder, comprising administering to an animal in need of such treatment an effective amount of a compound or pharmaceutical composition described herein. More particularly, the anxiety disorder is one or more of the following: panic disorder, specific phobia, social phobia, obsessive-compulsive disorder, generalized anxiety disorder, post-traumatic stress disorder; and acute stress disorder. The use of MAO inhibitors in the treatment of anxiety is known in the literature (e.g., Galynker et al., "Low-dose risperidone and queriapine as monotherapy for comorbid anxiety and depression", *J. Clin. Psychiatry* 2005, 66, 544).

Personality Disorders

In some embodiments, the neurological disorder is a personality disorder. Accordingly, the present invention provides a method of treating a personality disorder, comprising administering to an animal in need of such treatment an effective amount of a compound or pharmaceutical composition described herein. In particular embodiments, the personality disorder is one or more of the following: includes those of Cluster A (odd or eccentric), such as paranoid or schizoid personality disorder; those of Cluster B (dramatic, emotional, or erratic), such as antisocial, borderline, or narcissistic personality disorder; and those of Cluster C (anxious or fearful), such as avoidant, dependent, or obsessive-compulsive personality disorder.

Substance Related Disorders

In some embodiments, the neurological disorder is a substance-related disorder. Accordingly, a specific embodiment of the invention is a method of treating a substance-related disorder, comprising administering to an animal in need of such treatment an effective amount of a compound or pharmaceutical composition described herein.

More particularly, the substance-related disorder includes one or more of the following: an alcohol-related disorder, such as abuse, dependence, and withdrawal; an amphetamine (or amphetamine-related) disorder, such as abuse, dependence and withdrawal, a cocaine-related disorder, such as abuse, dependence and withdrawal; a hallucinogen-related disorder, such as abuse, dependence and withdrawal; an inhalant-related disorder, such as dependent and withdrawal; a nicotine-related disorder, such as dependence and withdrawal; an opioid-related disorder, such as abuse, dependence and withdrawal; a phencyclidine (or phencyclidine-like) related disorder, such as abuse and dependence; and a sedative-, hypnotic-, or anxiolytic-related disorder, such as abuse, dependence, and withdrawal (e.g., Melis et al, "The dopamine hypothesis of drug addiction: Hypodopaminergic state", *International Review of Neurobiology* 2005, 63, 101-154, 2005; and Volkow et al., "Profound decreases in dopamine release in striatum in detoxified alcoholics: Possible orbitofrontal involvement", *J. Neurosci.* 2007, 27, 12700-12706.

In a specific embodiment, the compounds and compositions of the present invention are useful as an aid to a treatment of smoking cessation. Accordingly, the present invention provides a method of treating smoking addiction, comprising administering to an animal in need thereof an effective amount of a compound or composition of the present invention.

Dissociative Disorders

In some embodiments, the neurological disorder is a dissociative disorder. Accordingly, a specific embodiment of the invention is a method of treating a dissociative disorder, comprising administering to an animal in need of such treatment an effective amount of a compound or pharmaceutical composition described herein. More particularly, the dissociative disorder includes one or more of the following: depersonalization disorder, dissociative amnesia, and dissociative identity disorder.

Eating Disorders

In some embodiments, the neurological disorder is an eating disorder. Accordingly, a specific embodiment of the invention is a method of treating an eating disorder, comprising administering to an animal in need of such treatment an effective amount of a compound or pharmaceutical composition described herein. More particularly, the eating disorder is anorexia nervosa or bulimia nervosa. The utility of MAO inhibitors in the treatment of eating disorders is known in the literature (e.g., Kaplan, *Expert Opin. Investig. Drugs.* 2003, 12, 1441-1443).

Sleep Disorders

In some embodiments, the neurological disorder is a sleep disorder. Accordingly, a specific embodiment of the invention is a method of treating a sleep disorder, comprising administering to an animal in need of such treatment an effective amount of a compound or pharmaceutical composition described herein. More particularly, the sleep disorder includes a primary sleep disorder, such as primary hypersomnia, primary insomnia, or narcolepsy; a parasomnia, such as a nightmare, or sleep terror disorder; and other sleep disorders. The utility of MAO inhibitors in the treatment of sleep disorders is known in the literature (e.g., Morgenthaler et al., "Practice parameters for the treatment of narcolepsy and other hypersomnias of central origins", Sleep 2007, 30, 1705-1711).

In other embodiments, the sleep disorder is restless leg syndrome. Restless legs syndrome (RLS) is a disorder of the part of the nervous system that affects the legs and causes an urge to move them. People with restless legs syndrome have uncomfortable sensations in their legs (and sometimes arms or other parts of the body) and an irresistible urge to move their legs to relieve the sensations. The sensations are usually worse at rest, especially when lying or sitting. The sensations can lead to sleep deprivation and stress. Because it usually interferes with sleep, it also is considered a sleep disorder. Accordingly, the present invention provides a method of treating restless leg syndrome, comprising administering to an animal in need thereof an effective amount of a compound or composition of the present invention.

Developmental Disorders

In some embodiments, the neurological disorder is a developmental disorder. Accordingly, a specific embodiment of the invention is a method of treating a developmental disorder, comprising administering to an animal in need of such treatment an effective amount of a compound or pharmaceutical composition described herein.

More particularly, the developmental disorder is one or more of the following: mental retardation, including mild, moderate, and severe forms; a learning disorder, such as that affecting reading, mathematics, or written expression; a motor skill disorder, such as developmental coordination disorder; a communication disorder; a pervasive developmental disorder, such as an autistic disorder, Rhett's disorder, childhood disintegrative disorder, or Asperger's disorder; an attention-deficit or disruptive disorder, such as attention-deficit hyperactivity disorder; and a tic disorder, such as Tourette's disorder, chronic motor disorder, or vocal tic disorder.

A specific embodiment of the invention is a method of treating an autistic disorder, comprising administering to an animal in need of such treatment an effective amount of a compound or pharmaceutical composition described herein. In another embodiment, the invention provides a method of treating an attention-deficit hyperactivity disorder, comprising administering to an animal in need of such treatment a therapeutically effective amount of a compound or pharmaceutical composition described herein. The utility of MAO inhibitors in the treatment of attention-deficit hyperactivity disorder is known in the literature (e.g., Spencer, "ADHD treatment across the life cycle", J. Clin. Psychiatry 2004, 65, 22-26).

Neurodegenerative Disorders

In particular embodiments, the invention provides a method of treating a neurodegenerative disorder, comprising administering to an animal in need of such treatment an effective amount of a compound or pharmaceutical composition described herein.

In one aspect, neurodegenerative disorders include Alzheimer's disease, Amyotrophic lateral sclerosis, corticobasal degeneration, chronic traumatic encephalopathy, and a disorder associated with repetitive head injury.

Alzheimer's Disease

In a specific embodiment, the invention provides a method of treating Alzheimer's disease, comprising administering to an animal in need of such treatment an effective amount of a compound or pharmaceutical composition described herein. A detailed set of criteria for the diagnosis of Alzheimer's is set forth in the Diagnostic and Statistical Manual of Mental Disorders (Fourth Edition, text revision (2000), also known as the DSM-IV-TR). First, multiple cognitive deficits must be present, one of which must be memory impairment. Second, one or more of the following must be present: aphasia (deterioration of language abilities); apraxia (difficulty executing motor activities—even though movement, senses, and the ability to understand what is being asked are still intact); or agnosia (impaired ability to recognize or identify objects—even though sensory abilities are intact).

Amyotrophic Lateral Sclerosis

In another specific embodiment, the invention provides a method of treating amyotrophic lateral sclerosis, comprising administering to an animal in need of such treatment an effective amount of a compound or pharmaceutical composition described herein.

Amyotrophic lateral sclerosis (ALS), often referred to as "Lou Gehrig's Disease," is a progressive neurodegenerative disease that affects nerve cells. Motor neurons reach from the brain to the spinal cord and from the spinal cord to the muscles throughout the body. As motor neurons degenerate, they can no longer send impulses to the muscle fibers that normally result in muscle movement.

Early symptoms of ALS often include increasing muscle weakness, especially involving the arms and legs, speech, swallowing or breathing. The progressive degeneration of the motor neurons in ALS eventually leads to their death. When the motor neurons die, the ability of the brain to initiate and control muscle movement is lost. With voluntary muscle action progressively affected, patients in the later stages of the disease may become totally paralyzed.

Movement Disorders

In other embodiments, the invention provides a method of treating a movement disorder, comprising administering to an animal in need of such treatment an effective amount of a compound or pharmaceutical composition described herein. In one aspect, the movement disorder includes one or more of the following: Huntington's disease, Parkinson's disease, an essential tremor, a Lewy body disease, hypokinetic disease, Multiple Sclerosis, various types of Peripheral Neuropathy, dystonia, a basal ganglia disorder, hypokinesia (including akinesia), and dyskinesia. In addition, Tourette's syndrome and other tic disorders can be included as categories of movement disorders. The utility of MAO inhibitors in the treatment of movement disorders is known in the literature. (e.g., Waters, "Other pharmacological treatments for motor complications and dyskinesias", Mov. Disord. 2005, 20 Suppl 1 1, S38-S44; and Pearce et al., "The monoamine reuptake blocker brasofensine reverses akinesia without dyskinesia in MPTP-treated and levodopa-primed common marmosets", Mov. Disord. 2002, 17, 877-886).

In related embodiment, the invention provides a method of treating chorea, comprising administering to an animal in need of such treatment an effective amount of a compound or pharmaceutical composition described herein. Chorea can occur in a variety of conditions and disorders, and is a primary feature of Huntington's disease, a progressive neurological disorder (e.g., Mann and Chiu, "Platelet monoamine oxidase activity in Huntington's chorea", J. Neurol. Neurosurg. Psychiatry 1978, 41, 809-812).

Huntington's Disease

In a specific embodiment, the present invention provides a method of treating Huntington's disease, comprising administering to an animal in need of such treatment an effective amount of a compound or pharmaceutical composition described herein.

Huntington's Disease (HD, or Huntington chorea) is a disorder passed down through families in which nerve cells in certain parts of the brain waste away, or degenerate. It is caused by a genetic defect on chromosome 4, causing a CAG repeat, to occur many more times than normal. The CAG element is normally repeated 10 to 28 times, but in persons with Huntington's disease, is repeated 36 to 120 times.

There are two forms of Huntington's disease: adult-onset Huntington's disease—which is the most common form and usually begins in the mid 30s and 40s; and early-onset Huntington's disease, which accounts for a small number of cases and begins in childhood or adolescence.

Symptoms of Huntington's disease include behavioral changes, abnormal and unusual movements, and worsening dementia. Behavioral changes may include behavioral disturbances, hallucinations, irritability, moodiness, restlessness or fidgeting, paranoia, and psychosis. Abnormal and unusual movements include facial movements, such as grimaces; head turning to shift eye position; quick, sudden, sometimes wild jerking movements of the arms, legs, face, and other body parts; slow, uncontrolled movements; and unsteady gait. Worsening dementia includes; disorientation or confusion; loss of judgment; loss of memory; personality changes; and speech changes (e.g., Dumas et al., "A review of cognition in Huntington's disease", *Front Biosci* (Schol Ed) 2013, 5, 1-18). The utility of MAO-B inhibitors in treating Huntington's disease is known in the art (e.g., Messer et al., "Up-regulation of the isoenzymes MAO-A and MAO-B in the human basal ganglia and pons in Huntington's disease revealed by quantitative enzyme radioautography), *Brain Res.* 2011, 1370, 204-214).

Parkinson's Disease

In a specific embodiment, the present invention provides a method of treating Parkinson's disease, comprising administering to an animal in need of such treatment an effective amount of a compound or pharmaceutical composition described herein.

Parkinson's disease (PD) (also known as Parkinson's, idiopathic parkinsonism, primary parkinsonism, PD, hypokinetic rigid syndrome/HRS, or paralysis agitans) is a degenerative disorder of the central nervous system estimated to afflict five million people worldwide. It is a slowly progressive neurological condition, characterized by tremors, stiffness, slowness of movement (bradykinesia) and impaired balance. Dopaminergic neurons decline steadily in PD, with motor symptoms emerging when about 50% of nigral neurons have degenerated (Bernheimer et al., "Brain dopamine and the syndromes of Parkinson and Huntington: clinical, morphological and neurochemical correlations", *J. Neurol. Sci.* 1973, 20, 415-455). At disease presentation, there is approximately a 70-80% loss of striatal dopamine concentration (Fearnley and Lees, "Aging and Parkinson's disease: substantia nigra regional selectivity", *Brain* 1991, 114, 2283-2301).

More generally, MAO-B levels increase with age, with post mortem brain samples showing increases of 41.5 and 30.4% in the putamen and globus pallidus lateralis, respectively, between 60 and 90 years of age (Saura et al., "Biphasic and region specific MAO-B response to aging in normal human brain", *Neurobiol. Aging* 1997, 18, 497-507).

Hence MAO-B inhibitors lead to an increase in natural dopamine levels in the brain as well as an increase in dopamine levels produced from levodopa (which is a dopamine precursor and is metabolized to dopamine by aromatic amino acid decarboxylase) and are one of the mainstays in the treatment of PD.

In another aspect, the invention provides a method of treating Parkinson's disease with a compound or pharmaceutical composition described herein, along with one or more agents useful in treating Parkinson's diseases, for example, L-DOPA; a dopaminergic agonist; a DOPA decarboxylase inhibitor (DCI); or a catechol-O-methyltransferase (COMT) inhibitor. Also claimed is a pharmaceutical composition comprising a compound of formula I and one or more agents known to be useful in the treatment of Parkinson's.

In another embodiment, the invention provides a method of treating myoclonus, Gilles de Ia Tourette's syndrome, dystonia, or tics, comprising administering to an animal in need of such treatment an effective amount of a compound or pharmaceutical composition described herein. The utility of MAO inhibitors in the treatment of myoclonus, Tourette's syndrome, dystonia and tics is known in the literature (e.g., Jankovic and Beach, "Long-term effects of tetrabenazine in hyperkinetic movement disorders", *Neurology* 1997, 48, 358-362).

A specific embodiment of the invention is a method of treating myoclonus, Gilles de Ia Tourette's syndrome, dystonia, or tics, comprising administering to an animal in need of such treatment an effective amount of a compound or pharmaceutical composition described herein. The utility of MAO inhibitors in the treatment of myoclonus, Tourette's syndrome, dystonia and tics is known in the literature (e.g., Jankovic and Beach, "Long-term effects of tetrabenazine in hyperkinetic movement disorders", Neurology 1997, 48, 358-362).

In a specific aspect, a movement disorder also includes multiple sclerosis, basal ganglia disorders, hypokinesia, and dyskinesia.

Lewy Body Diseases

In one embodiment, the present embodiment, the invention provides a method of treating a Lewy Body Disease, comprising administering to an animal in need of such treatment an effective amount of a compound or composition of the present invention. Lewy bodies appear as spherical masses that displace other cell components. The two morphological types are classical (brain stem) Lewy bodies and cortical Lewy bodies. A classical Lewy body is an eosinophilic cytoplasmic inclusion consisting of a dense core surrounded by a halo of 10-nm-wide radiating fibrils, the primary structural component of which is alpha-synuclein. In contrast, a cortical Lewy body is less well defined and lacks the halo. Nonetheless, it is still made up of alpha-synuclein fibrils. Cortical Lewy bodies are a distinguishing feature of Dementia with Lewy bodies (DLB), but may occasionally be seen in ballooned neurons characteristic of Pick's disease and corticobasal degeneration, as well as in patients with other tauopathies.

More particularly, the Lewy Body disorder is selected from the group consisting of multiple system atrophy, particularly the Parkinsonian variant; Parkinson disease without or with dementia (PDD); dementia with LBs (DLB) alone or in association with Alzheimer disease (AD); multiple system atrophy, particularly the Parkinsonian variant, as well as Pick's disease and corticobasal degeneration.

Multiple Sclerosis

In one embodiment, the present invention provides a method of treating a motor symptom associated with multiple sclerosis (MS), compring administering to animal in need of such treatment an effective amount of a compound or composition of the present invention. MS is an autoimmune, demyelinating disease that affects the brain and spinal cord of the CNS. It affects women more than men and is most commonly diagnosed between ages 20 and 40, but can be seen at any age.

MS is caused by damage to the myelin sheath, the protective covering that surrounds nerve cells. When this nerve covering is damaged, nerve signals slow down or stop. Because nerves in any part of the brain or spinal cord may be damaged, patients with multiple sclerosis can have symptoms in many parts of the body. Symptoms vary, because the location and severity of each attack can be different. Episodes can last for days, weeks, or months. These episodes alternate with periods of reduced or no symptoms (remissions).

Muscle symptoms associated with MS include loss of balance; muscle spasms; numbness, tingling, or abnormal sensation in any area; problems moving arms or legs; problems walking; problems with coordination and making small movements; tremor in one or more arms or legs; and weakness in one or more arms or legs.

Basal Ganglia Disorders

In particular embodiments, the present invention provides a method of treating a basal ganglia disorder. Basal ganglia disorders refer to a group of physical dysfunctions that occur when the group of nuclei in the brain known as the basal ganglia fail to properly suppress unwanted movements or to properly prizzme upper motor neuron circuits to initiate motor function (Leisman and Mello, *Rev. Neurosci.* 2013, 24, 9-25).

Increased output of the basal ganglia inhibits thalamocortical projection neurons. Proper activation or deactivation of these neurons is an integral component for proper movement. If something causes too much basal ganglia output, then the thalamocortical projection neurons become too inhibited and one cannot initiate voluntary movement. These disorders are known as hypokinetic disorders. However, a disorder leading to abnormally low output of the basal ganglia leads to relatively no inhibition of the thalamocortical projection neurons. This situation leads to an inability to suppress unwanted movements. These disorders are known as hyperkinetic disorders (Wichmann and DeLong, *Curr. Opin. Neurobiol* 1996, 6, 751-758).

Hypokinesia

In particular embodiments, the present invention provides a method of treating hypokinesia. Hypokinesia refers to decreased bodily movements, and they may be associated with basal ganglia diseases (such as Parkinson's disease), mental health disorders and prolonged inactivity due to illness, amongst other diseases.

More generally, hypokinesia describes a spectrum of disorders, including: (i) Akinesia, which refers to the inability to initiate movement due to difficulty selecting or activating motor programs in the central nervous system. Akinesia is a result of severely diminished dopaminergic cell activity in the direct pathway of movement and is common in severe cases of Parkinson's disease; (ii) Bradykinesia, which is characterized by slowness of movement and has been linked to Parkinson's disease and other disorders of the basal ganglia. Rather than being a slowness in initiation (akinesia), bradykinesia describes a slowness in the execution of movement. It is one of the 3 key symptoms of parkinsonism, which are bradykinesia, tremor and rigidity. Bradykinesia is also the cause of what is normally referred to as "stone face" (expressionless face) among those with Parkinson's; (iii) Freezing, which is characterized by an inability to move muscles in any desired direction; and (iv) Rigidity, which is characterized by an increase in muscle tone causing resistance to externally imposed joint movements; and (v) Postural instability, which is the loss of ability to maintain an upright posture.

Dyskinesia

In particular embodiments, the present invention provides a method of treating dyskinesia. Dyskinesia is a movement disorder which consists of adverse effects including diminished voluntary movements and the presence of involuntary movements, similar to tics or chorea.

Dyskinesia can be anything from a slight tremor of the hands to uncontrollable movement of, most commonly, the upper body but can also be seen in the lower extremities. Discoordination can also occur internally especially with the respiratory muscles and it often goes unrecognized. Dyskinesia is a symptom of several medical disorders, distinguished by the underlying cause and generally corresponding to one of three types: acute dyskinesia, chronic (or tardive) dyskinesia, and non-motor dyskinesia.

More specifically, a dyskinesia can include one or more the following: paroxysmal dyskinesias, e.g., primary and secondary paroxysmal dyskinesias; paroxysmal kinesigenic dyskinesias (PKD); paroxysmal non-kinesigenic dyskinesias (PNKD); paroxysmal exercise-induced (exertion-induced) dyskinesias (PED); and paroxysmal hypnogenic dyskinesias (PHD).

Trauma-Related Disorders

In specific embodiments, the present invention provides a method of treating a trauma-related disorder, comprising administering to an animal in need of such treatment an effective amount of a compound or pharmaceutical composition of the present invention.

In specific embodiments, trauma-related disorders comprise brain trauma; head trauma (closed and penetrating); head injury; tumors, especially cerebral tumors affecting the thalamic or temporal lobe head injuries; cerebrovascular disorders (diseases affecting the blood vessels in the brain), such as stroke, ischemia, hypoxia, and viral infection (e.g., encephalitis); excitotoxicity; and seizures (e.g., Huang et al., "Neuroprotective effect of rasagiline, a selective monoamine oxidase-B inhibitor, against closed head injury in the mouse", *Eur. J. Pharmacol.* 1999, 366, 127-135).

Conditions within the scope of the invention that are amenable to neuroprotection include: Stroke; traumatic brain injury (TB); Dementia; Alzheimer's disease; Parkinson's disease; Huntington's disease; Cerebral palsy; Post-polio syndrome; Guillain-Barre syndrome, and Multiple Sclerosis; and other developmental syndromes, genetic conditions, and progressive CNS diseases affecting cognitive function, such as autism spectrum disorders, fetal alcohol spectrum disorders (FASD), Rubinstein-Taybi syndrome, Down syndrome, and other forms of mental retardation.

Pain Disorders

In specific embodiments, the invention provides methods of treating pain, comprising administering to an animal in need of such treatment an effective amount of a compound or pharmaceutical composition described herein. The utility of MAO inhibitors in the treatment of pain is known in the literature (e.g., Pirildar et al., "A preliminary open-label study of moclobemide treatment of pain disorder", *Psychopharmacol. Bull.* 2003, S37, 127-134; and Silberstein et al., "Preventive treatment of Tragraine: an overview", *Cephalalgia.* 1997, 17, 67-72).

In particular embodiments, the pain disorder includes one or more of the following: dental pain, cancer pain, myofascial pain, perioperative pain, acute pain, chronic pain, posttraumatic pain, trigeminal neuralgia, migraine severe pain, intractable pain, neuropathic pain, post-traumatic pain, cancer pain, non-cancer pain. Pain also encompasses a pain disorder associated with psychological factors, a pain disorder associated with a general medical condition, and a pain disorder associated with both psychological factors and a general medical condition.

Cognitive Disorders

In particular embodiments of the invention, the neurological disorder is a cognitive disorder. Accordingly, the present invention provides a method of treating a cognitive disorder, comprising administering to an animal in need of such treatment an effective amount of a compound or pharmaceutical composition described herein. The utility of MAO inhibitors in the treatment of cognitive disorders is known in the literature (e.g., Schneider, "New therapeutic approaches to cognitive impairment", *J. Clin. Psychiatry* 1998, 59, 8-13; U.S. 2007-0203154, U.S. 2011-0160248, U.S. 2010-0317648, and U.S. Pat. No. 8,222,243).

Cognitive disorders can significantly impair social and occupational functioning, adversely impacting the autonomy and quality of life of the affected individual. An estimated four to five million Americans (about 2% of all ages and 15% of those older than 65) have some form and degree of cognitive impairment (Abrams et al., *Merck Manual of Geriatrics*, 1995, Whitehouse Station (NJ), Medical Services).

Cognitive disorders reflect problems in cognition, i.e., the general processes by which knowledge is acquired, retained and used. Accordingly, cognitive disorders can encompass impairments in such functions as concentration, perception, attention, information processing, learning, memory, or language. Cognitive disorders can also encompass impairments in psychomotor learning abilities, which include physical skills, such as movement and coordination; fine motor skills such as the use of precision instruments or tools; and gross motor skills, such as dance, musical, or athletic performance.

Cognitive disorders also encompass impairments in executive functions, which include abilities underlying the planning and execution of goal-oriented behaviors. Such abilities include flexibility, i.e., the capacity for quickly switching to the appropriate mental mode; anticipation and prediction based on pattern recognition; reasoning and problem-solving; decision making; working memory, i.e., the capacity to hold and manipulate internally- or externally-derived information in real time; emotional self-regulation, including the ability to recognize and manage one's emotions for good performance; sequencing, such as the ability to dissect complex actions into manageable units and prioritize them in the right order; and self-inhibition, i.e., the ability to withstand distraction and internal urges.

Cognitive disorders also comprise cognitive impairments (deficits or dysfunctions) that are associated with (due to) to CNS disorders. In one aspect, a cognitive impairment can be a direct result of a CNS disorder. For example, impairments in speech and language can directly result from a stroke or head-injury that damages the brain regions controlling speech and language, as in aphasia.

In another aspect, a cognitive impairment is associated with a complex CNS disorder, condition, or disease. For example, a cognitive impairment can comprise a deficit in executive control that accompanies autism or mental retardation; a deficit in memory associated with schizophrenia or Parkinson's disease; or a cognitive deficit arising from multiple sclerosis. In the case of multiple sclerosis (MS), for example, about one-half of MS patients will experience problems with cognitive function, such as slowed thinking, decreased concentration, or impaired memory. Such problems typically occur later in the course of MS—although in some cases they can occur much earlier, if not at the onset of disease.

Cognitive impairments can be due to many, non-exclusive categories of DNS disorders, including the following (and as described herein):

(1) dementias, such as those associated with Alzheimer's disease, Parkinson's disease; Huntington's disease, Pick's disease, Creutzfeldt-Jakob, AIDS Dementia, and other neurodegenerative disorders; and cognitive disabilities associated with progressive diseases involving the nervous system, such as multiple sclerosis.

(2) psychiatric disorders, which include affective (mood) disorders, such as depression and bipolar disorders; psychotic disorders, such as schizophrenia and delusional disorder; and neurotic and anxiety disorders, such as phobias, panic disorders, obsessive-compulsive disorder, generalized anxiety disorder; eating disorders; and posttraumatic stress disorders.

(3) developmental syndromes, genetic conditions, and progressive CNS diseases affecting cognitive function, such as autism spectrum disorders; fetal alcohol spectrum disorders (FASD); Rubinstein-Taybi syndrome; Down syndrome, and other forms of mental retardation; and multiple sclerosis.

(4) trauma-dependent losses of cognitive functions, i.e., impairments in memory, language, or motor skills resulting from brain trauma; head trauma (closed and penetrating); head injury; tumors, especially cerebral tumors affecting the thalamic or temporal lobe; cerebrovascular disorders (diseases affecting the blood vessels in the brain), such as stroke, ischemia, hypoxia, and viral infection (e.g., encephalitis); excitotoxicity; and seizures. Such trauma-dependent losses also encompass cognitive impairments resulting from extrinsic agents such as alcohol use, long-term drug use, and neurotoxins, e.g., lead, mercury, carbon monoxide, and certain insecticides (e.g., Duncan et al., "Monoamine oxidases in major depressive disorder and alcoholism", *Drug Discover. Ther.* 2012, 6, 112-122).

(5) age-associated cognitive deficits, including age-associated memory impairment (AAMI; also referred to herein as age-related memory impairment (AMI)), and deficits affecting patients in early stages of cognitive decline, as in Mild Cognitive Impairment (MCI); and (6) learning, language, or reading disabilities, such as perceptual handicaps, dyslexia, and attention deficit disorders.

Accordingly, the invention provides a method of treating a cognitive impairment associated with a CNS disorder selected from one or more of the group comprising: dementias, including those associated with neurodegenerative disorders; psychiatric disorders; developmental syndromes, genetic conditions, and progressive CNS diseases and genetic conditions; trauma-dependent losses of cognitive function, age-associated cognitive deficits; and learning, language, or reading disorders.

Dementias

In a specific embodiment, the invention provides a method of treating a cognitive deficit associated with dementia, comprising administering to an animal in need of such treatment an effective amount of a compound or pharmaceutical composition described herein.

Dementias are neurodegenerative diseases characterized by learning and cognitive deficiencies and are typically accompanied by behavioral symptoms, psychological symptoms and motor symptoms. More particularly, dementia symptoms can include difficulty with many areas of mental function, including emotional behavior or personality, language, memory, perception, and thinking and judgment.

Dementias include, but are not limited to, the following: dementia due to Alzheimer's disease (with early or late onset), dementia due to Parkinson's disease, dementia due to Pick's disease, dementia due to Creutzfeldt-Jakob disease, dementia due to HIV disease, dementia due to head trauma; dementia due to a vascular disease ("vascular dementia"), Lewy body dementia, fronto-temporal dementia, Pick's disease and corticobasal degeneration.

In one embodiment, dementia is due to Alzheimer's disease. Accordingly, the present invention provides a method of treating dementia due to Alzheimer's disease, comprising administering to an animal in need of such treatment a therapeutically effective amount of a compound or pharmaceutical composition described herein. The utility of MAO-B inhibitors in the treatment of Alzheimer's disease is known in the literature (e.g., Ono et al., "Antiparkinsonian agenst have anti-amyloidogenic activity for Alzheimer's beta-amyloid fibrils in vitro", Neurochem. Int. 2006, 48, 275-285). Accordingly, the invention provides a method of treating dementia due to Alzheimer's disease, comprising administering to an animal in need of such treatment a therapeutically effective amount of a compound or pharmaceutical composition described herein.

In another embodiment, dementia is due to Parkinson's disease. Accordingly, the invention provides a method of treating dementia due to Parkinson's disease, comprising administering to an animal in need of such treatment a therapeutically effective amount of a compound or pharmaceutical composition described herein. Dementia has been reported to occur in approximately 20%-60% of individuals with Parkinson's disease and is more likely to be present in older individuals or those with more severe or advanced disease. The dementia associated with Parkinson's disease is characterized by cognitive and motoric slowing; problems with executive functioning, such as planning tasks, organizing projects, or carrying out goals in the proper sequence; and impairment in memory retrieval. Declining cognitive performance in individuals with Parkinson's disease is frequently exacerbated by depression. The utility of MAO-B inhibitors in treating Parkinson's disease is known in the literature (e.g., Weinstock, et al., "A novel cholinesterdas and brain-selective monoamine oxidase inhibitor for the treatment of dementia comorbid with depression and Parkinson's disease", Prog. Neuropsychopharmacol. Biol. Psychiatry 2003, 27, 555-561).

Dementia has been reported to occur in approximately 20%-60% of individuals with Parkinson's disease and is more likely to be present in older individuals or those with more severe or advanced disease. The dementia associated with Parkinson's disease is characterized by cognitive and motoric slowing, executive dysfunction, and impairment in memory retrieval. Declining cognitive performance in individuals with Parkinson's disease is frequently exacerbated by depression. For a review, Davie, "A review of Parkinson's disease", Br. Med. Bull. 2008, 86, 109-127. The motor symptoms of Parkinson's disease result from the death of dopamine-generating cells in the substantia nigra, a region of the midbrain; the cause of this cell death is unknown. Early in the course of the disease, the most obvious symptoms are movement-related. Four motor symptoms are considered cardinal in PD: shaking (tremors), rigidity, slowness of movement, and postural instability, i.e., difficulty with walking and gait (e.g., Jankovic, "Parkinson's disease: clinical features and diagnosis", J. Neurol. Neurosurg. Psychiatr. 2008, 79, 368-376). Later, cognitive and behavioral problems may arise, with dementia commonly occurring in the advanced stages of the disease. Other symptoms include sensory, sleep and emotional problems. PD is more common in the elderly, with most cases occurring after the age of 50.

In another aspect, a cognitive impairment is associated with a complex CNS syndrome, condition, or disease. For example, a cognitive impairment can comprise a deficit in executive control that accompanies autism or mental retardation; a deficit in memory associated with schizophrenia or Parkinson's disease; or a cognitive deficit arising from multiple sclerosis. In the case of multiple sclerosis (MS), for example, about one-half of MS patients will experience problems with cognitive function, such as slowed thinking, decreased concentration, or impaired memory. Such problems typically occur later in the course of MS—although in some cases they can occur much earlier, if not at the onset of disease.

In one aspect, a cognitive impairment can be a direct result of a CNS disorder. For example, impairments in speech and language can directly result from a stroke or head-injury that damages the brain regions controlling speech and language, as in aphasia.

Psychiatric Disorders

In a specific embodiment, the invention provides a method of treating a cognitive deficit associated with a psychiatric disorder, comprising administering to an animal in need of such treatment an effective amount of a compound or pharmaceutical composition described herein. Psychiatric disorders include affective disorders (mood disorders), such as depression and bipolar disorders; psychotic disorders, such as schizophrenia and delusional disorder; and neurotic and anxiety disorders, such as phobias, panic disorders, obsessive-compulsive disorder, generalized anxiety disorder, eating disorders, and posttraumatic stress disorders.

Developmental Syndromes, Genetic Disorders, and Progressive Diseases

In a specific embodiment, the invention provides a method of treating a cognitive deficit associated with a developmental syndrome, genetic disorder, or progressive disease, comprising administering to an animal in need of such treatment an effective amount of a compound or pharmaceutical composition described herein. In a specific aspect, the cognitive deficit is associated with an autism spectrum disorder; a fetal alcohol spectrum disorder (FASD); Rubinstein-Taybi syndrome; Down syndrome, and other forms of mental retardation; and multiple sclerosis.

Trauma-Related Disorders

In a specific embodiment, the invention provides a method of treating a cognitive deficit associated with trauma. Such trauma-dependent losses of cognitive function include, but are not limited to, those due to cerebrovascular diseases, including stroke and ischemia; brain trauma, including subdural hematoma and brain tumor; traumatic brain injury (TBI) and head injury.

Such trauma-dependent losses also encompass cognitive impairments resulting from extrinsic agents such as alcohol use, long-term drug use, and neurotoxins such as lead, mercury, carbon monoxide, and certain insecticides.

Age-Associated Cognitive Deficits

AAMI

In a specific embodiment, the invention provides a method of treating an age-associated cognitive deficit. In one aspect, the age-associated cognitive deficit is age-related memory impairment (AAMI). Accordingly, the invention provides a method of treating age-associated memory impairment (AAMI), comprising administering to an animal in need of such treatment an effective amount of a compound or pharmaceutical composition described herein.

AAMI is a decline in various cognitive abilities, in particular memory abilities, associated with normal aging. For example, AAMI subjects show a decline in the ability to encode new memories of events or facts, as well as working memory (Hedden and Gabrieli, "Insights into the aging mind:

a view from cognitive neuroscience", *Nat. Rev. Neurosci.* 2004, 5, 87-96). In addition, AAMI subjects, when compared with age-matched controls, appeared to be impaired in tests of executive functions associated with frontal lobe function. These and other studies suggest an important role for frontal lobe dysfunction in the memory loss of elderly people. More generally, studies comparing the effects of aging on episodic memory, semantic memory, short-term memory and priming find that episodic memory is especially impaired in normal aging; but some types of short-term memory can also be impaired (Nilsson, "Memory function in normal aging", *Acta Neurol. Scand. Suppl.* 2003, 179, 7-13)

In general, an AAMI diagnosis identifies persons with subjectively and objectively evidenced memory loss without cognitive decline impaired enough to warrant the diagnosis of dementia. According to criteria established by the NIH working group (Crook et al., "Age-associated memory impairment: proposed diagnostic criteria and measures of clinical damage—report of a National Institute of Mental Health work group", *Devel. Neuropsychol.* 1986, 2, 261-276) a diagnosis of AAMI includes the following in a person aged 50 or older:

i) the presence of subjective memory decline, e.g., complaints of memory loss reflected in such everyday problems as difficulty remembering names of individuals introduced to the subject, misplacing objects, difficulty remembering a list of items to be purchased or a list of tasks to be performed;

ii) objective evidence of memory loss (e.g., a score at least one standard deviation below the mean of younger adults in a well standardized memory test);

iii) evidence of adequate intellectual function (e.g., a raw score of at least 32) on the Vocabulary subtest of the Wechsler Adult Intelligence Scale., and iv) the absence of dementia (or other memory-affecting disease, such as stroke), e.g., based on the Global Deterioration Scale for assessment of dementia, individuals with AAMI have very mild cognitive decline (level 2) (Reisberg et al., "The global deterioration Scale for assessment of primary degenerative dementia", *Am. J. Psych.* 1982, 139, 1136-1139).

Individuals with AAMI have been shown to have a threefold greater risk for development of dementia than individuals who do not meet AAMI criteria (Goldman and Morris, "Evidence that age-associated memory impairment is not a normal variant of aging" *Alzheimer Dis. Assoc. Disord.* 2002, 15:72-79).

MCI

In a specific embodiment, the invention provides a method of treating mild cognitive impairment (MCI), comprising administering to an animal in need of such treatment an effective amount of a compound or pharmaceutical composition described herein.

MCI may be diagnosed when an individual's memory declines below the level considered normal for that age group. In other words, MCI is a condition in which people face memory problems more often than that of the average person their age. These symptoms, however, do not prevent them from carrying out normal activities and are not as severe as the symptoms for Alzheimer's disease. Symptoms often include misplacing items, forgetting events or appointments, and having trouble thinking of desired words.

According to recent research, MCI has been called the transitional state between cognitive changes of normal aging and Alzheimer's disease (AD). Many people who experience mild cognitive impairment are at a high risk of developing Alzheimer's disease. Indeed, research suggests that: about 12% of people aged 65 or older diagnosed with MCI go on to develop Alzheimer's disease within a year; and that about 40% develop Alzheimer's within three years. This is a much higher rate than in the general population, wherein only about 1% of people aged 65 or older develop Alzheimer's each year.

Thus, people with MCI are considered at heightened risk to develop Alzheimer's disease. These symptoms, however, do not prevent them from carrying out normal activities and are not as severe as the symptoms for Alzheimer's disease. Symptoms often include misplacing items, forgetting events or appointments, and having trouble thinking of desired words (e.g., Arnaiz and Almkvist, "Neuropsychological features of mild cognitive impairment and preclinical Alzheimer's disease" *Acta Neurol. Scand. Suppl.* 2003, 179, 34-41). Some patients with MCI, however, never progress to AD.

Learning and Related Disabilities

In a specific embodiment, the invention provides a method of treating a learning, language, or reading disability, comprising administering to an animal in need of such treatment an effective amount of a compound or pharmaceutical composition described herein.

Neuroprotection

In specific embodiments, the invention provides a method of neuroprotection, comprising administering to animal in need thereof an effective amount of a chemical entity or composition of the present invention.

Like neuroplasticity, neuroprotection reflects an endogenous neurobiological process that is central to protection of the nervous system. More specifically, neuroprotection refers to the ability to halt or slow the loss of neurons, thereby preventing or slowing disease progression and secondary injuries. In a particular aspect, neuroprotection targets neuronal damage arising from oxidative stress and excitotoxicity—both of which are highly associated with CNS disorders, despite differences in symptoms or injuries.

The utility of MAO inhibitors in the treatment of neuronal damage is known in the literature. In addition to neurodegenerative diseases, neuronal damage can also result from other sources of trauma, such as cerebrovascular diseases, including stroke and ischemia; brain trauma, including subdural hematoma and brain tumor; and head injury (e.g., Dunnett and Björklund, "Prospects for new restorative and neuroprotective treatments in Parkinson's disease", *Nature* 1999, 399 (6738 Suppl), A32-A39; Anderson, "Oxidative stress in neurodegeneration: cause or consequence?" *Nat. Med.* 2004, 10 Suppl. S18-S25; Mandel et al., "Mechanism of neuroprotective action of the anti-Parkinson drug rasagiline and its derivatives", *Brain. Res.* 2005, 48, 379-387; and Muresanu et al., "Towards a roadmap in brain protection and recovery", *J. Cell. Mol. Med.* 2012, 116, 2861-2871).

Augmented Cognitive and Motor Training

In certain embodiments, a compound or composition herein is used as an augmenting agent in methods to enhance the efficiency of cognitive or motor training (collectively "training"). Such enhancement methods are collectively known as "augmented training," comprising "augmented cognitive training" or "augmented motor training."

Training generally requires multiple sessions to attain the desired benefits, for example, to rehabilitate a motor deficit or language deficit following stroke. This can be costly and time-consuming, deterring subject compliance and the realization of real world benefits that endure over time. The efficiency of such training protocols can be improved by administering certain agents (known as augmenting agents) in conjunction with the training protocol (e.g., U.S. Pat. No. 7,868,015; U.S. Pat. No. 7,947,731; US 2008-0188525). Augmented training comprises a specific training protocol for a particular brain function, such as that underlying declarative memory, performance of a fine motor skill, locomotion, language acquisition, an executive function, etc., and a general administration of CREB pathway-enhancing drugs. The training protocol (cognitive or motor training) induces neuronal activity in specific brain regions and produces improved performance of a specific brain (cognitive or motor) function.

In some embodiments, the invention provides methods of treating a cognitive disorder, and more particularly, methods for improving a cognitive deficit associated with a central nervous system (CNS) disorder or condition in an animal, comprising treating the animal with an augmenting agent that enhances CREB pathway function in conjunction with cognitive training, wherein the augmenting agent is a compound or composition of the present invention. Exemplary compounds of the present inventions, for example, have been shown to activate CREB in cell-based assays.

In one aspect, the method comprises: (a) providing cognitive training to a subject in need of treatment of a cognitive deficit under conditions sufficient to produce an improvement in performance by said animal of a cognitive function whose impairment is associated with said cognitive deficit; (b) administering a compound or composition of the present invention to the animal in conjunction with said cognitive training; repeating steps (a) and (b) one or more times; and (d) reducing the number of training sessions sufficient to produce the improvement in performance, relative to the same improvement in performance produced by cognitive training alone.

In another aspect, the method comprises: (a) providing cognitive training to a subject in need of treatment of a cognitive deficit under conditions sufficient to produce an improvement in performance by said animal of a cognitive function whose impairment is associated with said cognitive deficit; (b) administering a compound or composition of the present invention to the animal in conjunction with said cognitive training; repeating steps (a) and (b) one or more times; and (d) producing a long-lasting improvement in performance of said function relative to the improvement in performance of said function produced by cognitive training alone.

In one aspect, a compound or composition of the present invention can be used as an augmenting agent in conjunction with any psychotherapeutic approach intended to modulate cognitive function in the brain, thereby enhancing the efficacy of such therapy by reducing the number of sessions necessary to attain benefits.

In another aspect, the cognitive deficit treated by these methods is or includes memory impairment, and more particularly, a defect in long-term memory. Long-term memory (LTM) generally comprises two main biological properties. First, formation of long-term memory requires synthesis of new proteins. Second, it involves cAMP-responsive transcription and is mediated through the cAMP-response element binding protein (CREB) family transcription factors. Compounds of the present invention can act as CREB-augmenting agents and are therefore useful in enhancing memory formation in an animal, and more particularly, transcription-dependent memory. Indeed, exemplary compounds of the present invention activate CREB in cell-based assays.

In some embodiments, the invention provides methods of treating a motor disorder, and more particularly, methods for improving a motor deficit associated with a central nervous system (CNS) disorder or condition in an animal comprising treating the animal with an augmenting agent that enhances CREB pathway function in conjunction with motor training. Methods are also provided herein for providing sustained improvement in a motor deficit associated with a central nervous system (CNS) disorder or condition in an animal in need of said treatment comprising administering to the animal a compound or composition of the present invention; and detecting said sustained improvement In one aspect, the method comprises: (a) providing motor training to a subject in need of treatment of a motor deficit under conditions sufficient to produce an improvement in performance by said animal of a motor function whose impairment is associated with said cognitive deficit; (b) administering a compound or composition of the present invention to the animal in conjunction with said motor training; repeating steps (a) and (b) one or more times; and (d) reducing the number of training sessions sufficient to produce the improvement in performance, relative to the same improvement in performance produced by motor training alone.

In another aspect, the method comprises: (a) providing motor training to a subject in need of treatment of a motor deficit under conditions sufficient to produce an improvement in performance by said animal of a motor function whose impairment is associated with said cognitive deficit; (b) administering a compound or composition of the present invention to the animal in conjunction with said motor training; repeating steps (a) and (b) one or more times; and (d) producing a long-lasting improvement in performance of said function relative to the improvement in performance of said function produced by motor training alone.

In other embodiments, the invention provides methods for enhancing a specific aspect of cognitive performance in an otherwise healthy animal (particularly in a human or other mammal or vertebrate) comprising (a) administering to the animal an augmenting agent of the present invention; and (b) training the animal under conditions sufficient to produce an improvement in performance of a particular cognitive task by the animal. In other embodiments, the present invention provides methods of enhancing cognitive or motor performance, as well as methods for repeated stimulation of neuronal activity or a pattern of neuronal activity, such as that underlying a specific neuronal circuit(s).

Augmenting Agents

Augmenting agents, including the compounds and compositions herein, are able to enhance CREB pathway function. By enhancing CREB pathway function in conjunction with training, such augmented training can decrease the number of training sessions required to improve performance of a cognitive or motor function, relative to the improvement observed by training alone (e.g., U.S. 2007-0203154, U.S. 2011-0160248, U.S. 2010-0317648, and U.S. Pat. No. 8,222, 243).

The augmenting agent can be administered before, during or after one or more of the training sessions. In a particular embodiment, the augmenting agent is administered before and during each training session. Treatment with an augmenting agent in connection with each training session is also referred to as the "augmenting treatment".

Training Protocols

Training protocols are generally employed in rehabilitating individuals who have some form and degree of cognitive or motor dysfunction. For example, training protocols are commonly employed in stroke rehabilitation and in age-related memory loss rehabilitation. Because multiple training sessions are often required before an improvement or enhancement of a specific aspect of cognitive (or motor) performance (ability or function) is obtained in the individuals, training protocols are often very costly and time-consuming. Augmented training methods are more efficacious and therefore more cost-effective.

For example, human brain injury often results in motor and cognitive impairments. While advances in critical care medicine and patient management have led to improvements in patient outcome following traumatic brain injury (TBI), there is currently no known treatment to prevent the neuronal cell death and dysfunction that follows TBI. Although multiple treatments have proven neuroprotective in pre-clinical models of TBI, most have failed to show efficacy in humans.

Once a patient is stabilized following TBI, the standard of care dictates extensive motor or cognitive rehabilitation. During this rehabilitation the patient often regains lost skills, finally resulting in improved functional outcome. It would be beneficial if pharmaceutical treatments could be developed to enhance motor or cognitive rehabilitation following TBI, and thus improve functional outcome.

Cognitive and motor training protocols and the underlying principles are well known in the art (e.g., Allen et al., *Parkinsons Dis.* 2012, 1-15; Jaeggi et al., *Proc. Natl. Acad. Sci. USA* 2011, 108, 10081-10086; Chem et al., *Psychon. Bull. Rev.* 2010, 17, 193-199; Klingberg, *Trends Cogn. Sci.* 2010, 14, 317-324; Owen et al., *Nature* 2010, 465, 775-778; Tsao et al., *J. Pain* 2010, 11, 1120-1128; Lustig et al., *Neuropsychol. Rev.* 2009, 19, 504-522; Park and Reuter-Lorenz, *Ann. Rev. Psych.* 2009, 60, 173-196; Oujamaa et al., *Ann. Phys. Rehabil. Med.* 2009, 52, 269-293; Frazzitta et al., *Movement Disorders* 2009, 8, 1139-1143; Jaeggi et al., *Proc. Natl. Acad. Sci. USA* 2008, 105, 6829-6833; Volpe et al., *Neurorehabil. Neural Repair* 2008, 22, 305-310; Fischer et al., *Top. Stroke Rehab.* 2007, 14, 1-12; Jonsdottir et al., *Neurorehabil. Neural Repair* 2007, 21, 191-194; Stewart et al., *J. Neurol. Sci.* 2006, 244, 89-95; Krakauer, *Curr. Opin. Neurol.* 2006, 19, 84-90; Belleville et al., *Dement. Geriatr. Cogn. Disord.* 2006, 22, 486-499; Klingberg et al., *J. Am. Acad. Child. Adolesc. Psychiatry* 2005, 44, 177-186; Dean et al., *Arch. Phys. Med. Rehabil.* 2000, 81, 409-417; Whitall et al., *Stroke* 2000, 31, 2390-2395; Hummelsheim and Eickhof, *Scand. J. Rehabil. Med.* 1999, 31, 250-256; Merzenich et al., *Science* 1996, 271, 77-81; Merzenich et al., *Cold Spring Harb. Symp. Quant. Biol.* 1996, 61, 1-8; Rider and Abdulahad, *Percept. Mot. Skills* 1991, 73, 219-224 and Wek and Husak, *Percept. Mot. Skills,* 1989, 68, 107-113.

Cognitive training protocols are directed to numerous cognitive dimensions, including memory, concentration and attention, perception, learning, planning, sequencing, and judgment. Motor training protocols can be directed to numerous motor domains, such as the rehabilitation of arm or leg function after a stroke or head injury. One or more protocols (or modules) underlying a training program can be provided to a subject.

In some embodiments, the protocols can be used to treat, or rehabilitate, cognitive or motor impairments in afflicted subjects. Such protocols may be restorative or remedial, intended to reestablish prior skills and functions, or they may be focused on delaying or slowing cognitive or motor decline due to neurological disease. Other protocols may be compensatory, providing a means to adapt to a cognitive or motor deficit by enhancing function of related and uninvolved brain domains. In other embodiments, the protocols can be used to improve particular skills or cognitive or motor functions in otherwise healthy individuals. For example, a cognitive training program might include modules focused on delaying or preventing cognitive decline that normally accompanies aging; here the program is designed to maintain or improve cognitive health.

In general, a training protocol (or module) comprises a set of distinct exercises that can be process-specific or skill-based: Process-specific training focuses on improving a particular domain such as attention, memory, language, executive function, or motor function. Here the goal of training is to obtain a general improvement that transfers from the trained activities to untrained activities associated with the same cognitive or motor function or domain. For example, an auditory cognitive training protocol can be used to treat a student with impaired auditory attention. At the end of training, the student should show a generalized improvement in auditory attention, manifested by an increased ability to attend to and concentrate on verbal information presented in class—and therefore to remember to write down and complete homework assignments. Similarly, a cognitive training protocol may be directed to impaired executive function in an autistic subject, preventing the subject from carrying out instructions to complete an activity, such as making a meal, cleaning one's room, or preparing for school in the morning. Cognitive training allows the subject to focus his attention and concentration and as a result, complete the sequence of tasks required for such activities.

Skill-based training is aimed at improving performance of a particular activity or ability. Here the goal of training is to obtain a general improvement in the skill or ability. For example, a training protocol may focus on learning a new language, performing a musical instrument, improving memory, or learning a fine motor skill. The different exercises within such a protocol will focus on core components underlying the skill Modules for increasing memory, for example, may include tasks directed to the recognition and use of fact, and the acquisition and comprehension of explicit knowledge rules.

Some rehabilitation programs may rely on a single strategy (such as computer-assisted cognitive training) targeting either an isolated cognitive function or multiple functions concurrently. For example, the CogState testing method comprises a customizable range of computerized cognitive tasks able to measure baseline and change in cognitive domains underlying attention, memory, executive function, as well as language and social-emotional cognition (e.g., Yoshida et al., *PloS ON,* 2011, 6, e20469; Frederickson et al., *Neuroepidemiology* 2010, 34, 65-75). Other rehabilitation programs may use an integrated or interdisciplinary approach. Cognitive and motor training programs may involve computer games, hand-held game devices, interactive exercises, and may employ feedback and adaptive models.

Neurorehabilitation and Neurorecovery

In other embodiment, the invention further relates to the use of compounds and compositions of the present invention in neurorecovery and neurorehabilitation-endogenous neurobiological processes that are central to recovery of cognitive and motor impairments of the nervous system (e.g., Harkema et al., "Locomotor training: as a treatment of spinal cord injury and in the progression of neurologic rehabilitation", *Arch. Phys. Med. Rehabil.* 2012, 93, 1588-1597; Muresanu et al., "Towards a roadmap in brain protection and recovery", *J. Cell. Mol. Med.* 2012, 16, 2861-2871).

Neurorehabilitation or neurorecovery generally refers to a collection process that focuses on aiding a person's recovery from a neurological disorder, or helping that individual to live a more normal, active, and independent life. For example, the quality of life of a person can be greatly affected by a brain or spinal cord injury, or a medical condition which affects the mobility, cognitive functions, or other physical or psychological processes that have been affected by changes in the nervous system. The goal of neurorehabilitation is to combat those changes and improve quality of life by various therapies.

Conditions within the scope of the invention that are treated by neurorehabilitation and neurorecovery include: Stroke; traumatic brain injury (TB); Dementia; Alzheimer's disease; Parkinson's disease; Huntington's disease; Cerebral palsy; Post-polio syndrome; Guillain-Barre syndrome, and Multiple Sclerosis; and other developmental syndromes, genetic conditions, and progressive CNS diseases affecting cognitive function, such as autism spectrum disorders, fetal alcohol spectrum disorders (FASD), Rubinstein-Taybi syndrome, Down syndrome, and other forms of mental retardation.

By focusing on all aspects of a person's well-being, neurorehabilitation or neurorecovery offers a series of therapies from the psychological to occupational, teaching or re-training patients on mobility skills, communication processes, and other aspects of that person's daily routine. Neurorehabilitation or neurorecovery also provides focuses on nutrition, psychological, and creative parts of a person's recovery.

In one embodiment, the present invention provides a method of augmenting neurorehabilitation or neurorecovery from a cognitive impairment, comprising (a) providing cognitive training to a subject in need of treatment of a cognitive deficit under conditions sufficient to produce an improvement in performance by said animal of a cognitive function whose impairment is associated with said cognitive deficit; (b) administering a compound or composition of the present invention to the animal in conjunction with said cognitive training; repeating steps (a) and (b) one or more times; and (d) producing a long-lasting improvement in performance of said function relative to the improvement in performance of said function produced by cognitive training alone.

In another embodiment, the present invention provides a method of augmenting neurorehabilitation or neurorecovery from a motor impairment, comprising: (a) providing motor training to a subject in need of treatment of a motor deficit under conditions sufficient to produce an improvement in performance by said animal of a motor function whose impairment is associated with said cognitive deficit; (b) administering a compound or composition of the present invention to the animal in conjunction with said motor training; repeating steps (a) and (b) one or more times; and (d) reducing the number of training sessions sufficient to produce the improvement in performance, relative to the same improvement in performance produced by motor training alone.

Non-Human Animal Training Protocols

Aside from applications for humans, compounds and compositions of the present invention have additional uses for non-human animals, namely in enhancing (augmenting) the efficiency of training protocols directed to numerous cognitive and motor functions.

Conditions, under which non-human animals would benefit, include enhanced (augmented) training procedures for specific purposes, (e.g. hunting dogs, guide dogs, police dogs etc, or animals used in movie industry).

Enhanced training protocols can also benefit animals that have been exposed to stressful or traumatic conditions and are in need of training to treat the resulting cognitive impairments. Such a need may arise, for example, after such an animal has been captured or transported, subjected to new housing conditions (as in a change of domicile or owner), or has developed analogous disorders and is distressed or aggressive, or displays stereotypic behavior, obsessive-compulsive behavior, or anxiety. Animals which are subject to stress would also include animals used in racing (eg. dogs, horses, camels) or other sports, performing animals (such as circus animals and those appearing on stage, television or in the movies) and horses that perform dressage and other highly disciplined routines.

Compounds of the present invention can also enhance the efficiency of rehabilative protocols following physical injury to a non-human animal, such as limb amputation. For example, administering an augmenting agent of the present invention in conjunction with a trainin protocol can increase the efficiency of a rehabilitative program by decreasing the number of training sessions necessary to achieve an improvement in motor function.

In particular embodiments, compounds and compositions of the present invention are used in methods of training service animals. By combining augmenting agents of the present invention with training protocols, the efficiency of training non-human animals for service in both the public and private sectors will be enhanced. Service animals are typically dogs. However, other non-human animals can also be trained to perform services, such as assisting blind or disabled people. For example, miniature horses can be trained to guide the blind, to pull wheelchairs, or to provide support for Parkinson's patients. As another example, capuchin monkeys can be trained to assist disabled perform manual tasks, such as grasping items, operating knobs and switches, turning the pages of a book.

In specific embodiments, augmented training with compounds and compositions of the present invention can be used to reduce the number of training sessions necessary to teach an animal skills that are useful in public service, such as in law enforcement. In dogs, for example, such skills include, but are not limited to, the following: (i) public order maintenance, e.g., chasing, holding, or detaining suspects; (ii) search and rescue, e.g., locating suspects, missing persons, or objects; and (iii) contraband detection, e.g., detecting illicit substances such as drugs, narcotics, explosives, weapons, and even human remains. Such methods can therefore be applied to police dogs, bomb-sniffing dogs, drug-sniffing dogs, search and rescue dogs, etc.

In other embodiments, augmented training (with compounds and compositions of the present invention) can be used to reduce the number of training sessions required to teach animals skills that are useful in the private sector, such as security and medical care. In dogs, for example, such skills can include, but are not limited to, the following: (i) private security, e.g., guarding property or protecting an individual; (ii) handicap assistance, e.g., providing eyes for the visually impaired, ears for the hearing-impaired, arms and legs for the physically-disabled; (iii) health care, e.g., detecting cancer or altering a caregiver to seizures in a subject; (iv) psychiatric assistance, e.g., calming a phobic person under stress-triggering conditions, or alerting an autistic person to distracting repetitive movements such as hand flapping; and (v) pest control, e.g., identifying source of infestations by bedbugs or termites.

In some embodiments, the training protocol can be directed to a single skill or task, such as the detection of a single drug. In other embodiments, the training protocol can be directed to a complex set of skills, such as those underlying search and rescue. For a complex set of skills, training will therefore comprise more than one task.

In another aspect, when training is carried out with a wide enough scope of tasks, a generalized "rehabilitation" effect is expected, resulting in generalized improved function of one or more cognitive domains. This results in improved performance of the animal of related tasks (involving the same cognitive domains) that are not specifically part of the training protocol.

Accordingly, the present invention provides a method of reducing the time necessary to teach an animal one or more skills, wherein said reducing comprising: a) administering an augmenting agent of the present invention to the animal; b) providing a training protocol to said dog under conditions to improve performance of one or more tasks, wherein said training protocol comprises multiple training sessions; and c) decreasing the number of training sessions required to improve performance of said one or more tasks relative to the number of said training sessions required to produce said improvement in performance by the training protocol alone.

The training protocol can be provided to the animal under conditions to improve performance of a single task; a complex set of tasks; or a wide scope of tasks, resulting in generalized improved function of one or more cognitive domains. The tasks can relate to a skill involved in public service, such as public order maintenance, search and rescue, and contraband detection. The tasks can also relate to a skill involved in private service, such as private security, handicap assistance, health care, psychiatric assistance, and pest control.

Peripheral Disorders

MAO-B enzymes are located in a number of peripheral tissues, including adipose tissues, muscle, and liver. Thus, in one embodiment, the invention provides a method of treating a peripheral disorder associated with MAO-B, by administering to an animal in need thereof a therapeutically effective amount of a compound or pharmaceutical composition described herein.

Obesity, Diabetes, and Cardiometabolic Disorders

MAO-B inhibitors have been shown to reduce the amount of adipose tissue (i.e., body fat) in mammals (e.g., U.S. Pat. No. 8,138,209). Thus, in one embodiment, the invention provides a method of preventing or reversing the deposition of adipose tissue, by administering to an animal in need thereof a therapeutically effective amount of a compound or pharmaceutical composition described herein.

By preventing or reversing the deposition of adipose tissue, MAO-B inhibitors can also reduce the incidence or severity of obesity, diabetes, and cardiometabolic disorders. Accordingly, the invention provides a method of treating obesity, diabetes, or a cardiometabolic disorder, or a combination thereof, comprising administering to an animal in need of such treatment an effective amount of a compound or pharmaceutical composition described herein. In specific embodiments, the cardiometabolic disorder is selected from hypertension, dyslipidemias (e.g., undesired blood lipid levels, elevated cholesterol levels, and lowered LDL levels), high blood pressure, and insulin resistance.

A specific embodiment of the invention is a method of treating obesity in a mammal in need of such treatment, comprising administering to the mammal a therapeutically effective amount of a compound or pharmaceutical composition described herein (e.g., Visentin et al., "Alteration of amine oxidase activity in the adipose tissue of obese subjects." Obes. Res. 2004, 12, 547-55).

Comorbidities

Moreover, by reducing the incidence or severity of obesity, diabetes, and cardiometabolic disorders, MAO-B inhibitors reduce the incidence or severity of associated comorbidities. Accordingly, the invention provides a method of treating a comorbidity associated with obesity, diabetes, or a cardiometabolic disorder, or a combination thereof, in a mammal in need of such treatment, comprising administering to the mammal a therapeutically effective amount of a compound or pharmaceutical composition described herein. In specific embodiments, the comorbidity is a comorbidity of obesity, which includes diabetes, Metabolic Syndrome, dementia, cancer, and heart disease.

Examples

The present disclosure will be further illustrated by the following non-limiting Examples. These Examples are understood to be exemplary only, and they are not to be construed as limiting the scope of the invention herein, and as defined by the appended claims.

Preparative Examples

Exemplary compounds useful in methods of the invention will now be described by reference to the illustrative synthetic schemes for their general preparation below and the specific examples to follow.

Synthetic Schemes

One skilled in the art will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I). Reactions may be performed between −78° C. and the reflux temperature of the solvent. Reactions may be heated employing conventional heating or microwave heating. Reactions may also be conducted in sealed pressure vessels above the normal reflux temperature of the solvent.

Scheme A

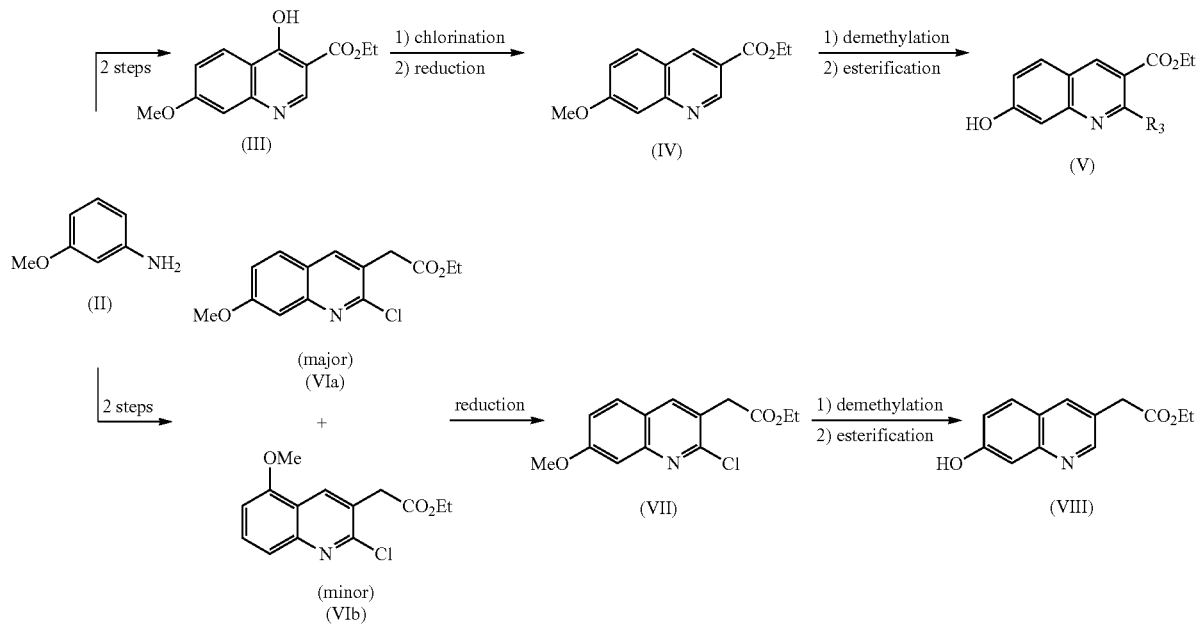

According to Scheme A, ethyl 4-hydroxy-7-methoxyquinoline-3-carboxylate (VIII) is obtained in four steps from commercially available synthetically accessible m-anisidine (II). m-Anisidine is combined with diethyl ethoxymethylenemalonate at temperatures ranging from 100° C. to about 125° C., preferably 125° C. for a period of 1 to 5 h, preferably about 3 h to provide diethyl 2-(((3-methoxyphenyl)amino)methylene)malonate. Ethyl 4-hydroxy-7-methoxyquinoline-3-carboxylate (III) is obtained by heating Dowtherm™ at a temperature of 257° C. and diethyl 2-(((3-methoxyphenyl)amino)methylene)malonate for a period of 15 minutes to 2 h. Compound (IV) ethyl 7-methoxyquinoline-3-carboxylate is commercially available or synthetically accessible from ethyl 4-hydroxy-7-methoxyquinoline-3-carboxylate (III) in two steps. Chlorination of compound (III) under conditions known to one skilled in the art, for example, but not limited to, oxalyl chloride, thionyl chloride, or phosphorus oxychloride, with or without a catalytic amount of DMF, in the presence or absence of a solvent such as DCM or CHCl$_3$, at temperatures ranging from 50° C. to about 70° C., for a period ranging from 2 to 4 h, preferably 2.5 h, provides ethyl 4-chloro-7-methoxyquinoline-3-carboxylate. Subsequent reduction of ethyl 4-chloro-7-methoxyquinoline-3-carboxylate, employing Pd/C under hydrogenation conditions, in a solvent such as MeOH or EtOH, in the presence or absence of an acid such as acetic or formic acid, provides ethyl 7-methoxyquinoline-3-carboxylate (IV). Commercially available or synthetically accessible ethyl 7-methoxyquinoline-3-carboxylate (IV) is reacted under demethylation conditions, for example, HBr in H$_2$O or HOAc, at temperatures ranging from 80° C. to about 110° C., preferably 105° C. for a period of 0.5 h to 24 h, preferably about 2 h, to provide 7-hydroxyquinoline-3-carboxylic acid. Ethyl 7-hydroxyquinoline-3-carboxylate (V), where R$^3$ is H, is obtained by esterification of 7-hydroxyquinoline-3-carboxylic acid, employing methods known to one skilled in the art, for example, but not limited to, reaction of 7-hydroxyquinoline-3-carboxylic acid with an acid such as H$_2$SO$_4$, and the like, in a solvent such as EtOH, at temperatures ranging from 60° C. to about 80° C., preferably 75° C. for a period of about 12 to 24 h, preferably 20 h.

Ethyl 7-hydroxy-2-methylquinoline-3-carboxylate (V), where R$_3$ is —CH$_3$, is obtained in two steps from commercially available or synthetically accessible 7-methoxy-2-methylquinoline-3-carboxylic acid. Demethylation of 7-methoxy-2-methylquinoline-3-carboxylic acid, employing methods previously described, for example, HBr in H$_2$O, at temperatures ranging from 80° C. to about 100° C., preferably ° C. for a period of 0.5 h to 24 h, preferably about 2 h provides 7-hydroxy-2-methylquinoline-3-carboxylic acid. Subsequent esterification of 7-hydroxy-2-methylquinoline-3-carboxylic acid employing methods previously described, provides ethyl 7-hydroxy-2-methylquinoline-3-carboxylate (V), where R$_3$ is —CH$_3$.

According to Scheme A, ethyl 2-(7-hydroxyquinolin-3-yl) acetate (VIII) is obtained in four steps from commercially available synthetically accessible m-anisidine (II). m-Anisidine is treated with ethyl succinyl chloride in a solvent such as THF, a suitably selected tertiary organic base such as triethylamine (TEA), and the like, at a temperature between 0° C. to about 65° C. and the reflux temperature of the solvent, to afford ethyl 4-((3-methoxyphenyl)amino)-4-oxobutanoate. Subsequent chlorination and cyclization of ethyl 4-((3-methoxyphenyl)amino)-4-oxobutanoate with phosphoryl chloride and DMF, at temperatures ranging from 0° C. to about 80° C., preferably 0° C. for 20 minutes followed by 75° C. for 1.5 h, provides ethyl 2-(2-chloro-7-methoxyquinolin-3-yl)acetate (VIa) and ethyl 2-(2-chloro-5-methoxyquinolin-3-yl)acetate (VIb). Reduction of compounds (VIa) and (VIb) employing conditions known to one skilled in the art, for example Pd/C under hydrogenation conditions, in a solvent such as MeOH or EtOH, provides ethyl 2-(7-methoxyquinolin-3-yl)acetate (VII). Demethylation of ethyl 2-(7-methoxyquinolin-3-yl)acetate (VII), employing conditions known to one skilled in the art, for example, HBr in H$_2$O or HOAc, at temperatures ranging from 95° C. to about 110° C., preferably 105° C., for a period of about 48 to 96 h, preferably 96 h. Subsequent esterification of 7-hydroxy-2-quinoline-3-carboxylic acid employing methods previously described provides ethyl 2-(7-hydroxyquinolin-3-yl)acetate (VIII).

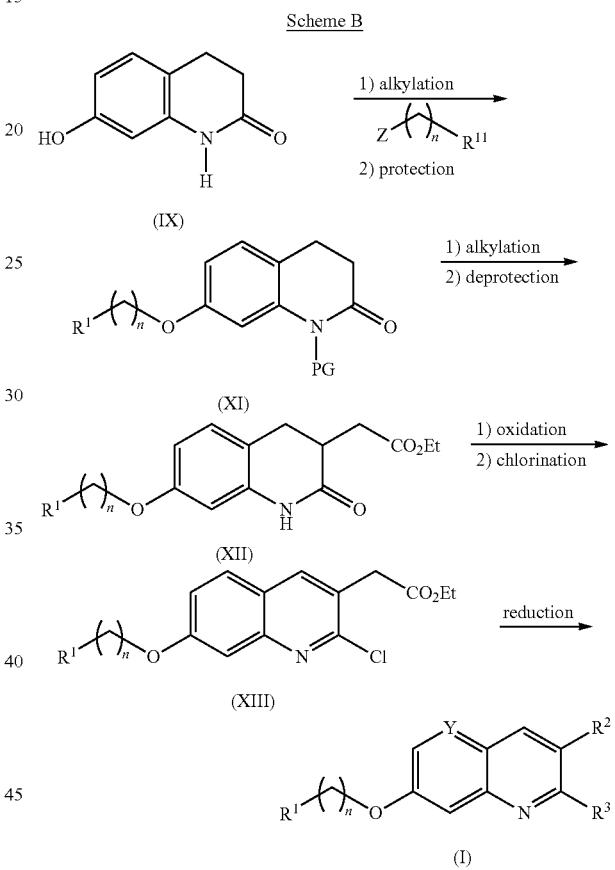

Scheme B

According to Scheme B, compound (XI) is obtained in two steps from 7-hydroxy-3,4-dihydroquinolin-2(1H)-one (IX). Alkylation of 7-hydroxy-3,4-dihydroquinolin-2(1H)-one (IX) with commercially available or synthetically accessible substituted benzyl halides of formula (X), where Z is —Br, n is 1 or 2 and R$^1$ is a suitably substituted aryl or heteroaryl moiety, in the presence of a base such as Cs$_2$CO$_3$, K$_2$CO$_3$, Na$_2$CO$_3$, NaH, DBU, and the like, in a polar aprotic solvent such as DMF, DMA, THF, ACN, DMSO, or a mixture thereof, at a temperature of about 25° C. to 75° C., preferably 25° C., for a period of 5 h provides substituted 3,4-dihydroquinolin-2(1H)-ones. In a preferred embodiment, the base is Cs$_2$CO$_3$ and the solvent is ACN. The variable "PG" refers to a suitable nitrogen protecting group, for example, tert-butylcarbamoyl (BOC), benzyl, or substituted benzyl. Subsequent protection with a —BOC group, under conditions known to one skilled in the art, for example, by reaction with di-tert-butyl dicarbonate (BOC$_2$O), triethylamine, DMAP, in a solvent such as DCM provides compounds of formula (XI). Alkylation of compounds of formula (XI), by reaction with a base such as lithium bis(trimethylsilyl)amide (LiHMDS), and the like, in a solvent such as THF, and the like, ethyl bromoacetate, at temperatures ranging from −78° C. to 25° C., for a period of 16 to 24 h. In a separate step, subsequent deprotection of the —BOC protecting group, under conditions known to one skilled in the art, for example, removal using HCl, TFA, or p-toluenesulfonic acid, in a solvent such as MeOH, dioxane, or DCM, provides compounds of formula (XII). Substituted quinolin-2(1H)-ones are obtained from 3,4-dihydroquinolin-2(1H)-ones of formula (XII), under oxidation conditions, for example, by reaction with 2,3-dichloro-5,6-dicyano-1,4-benzoquinone (DDQ), in a solvent such as chloroform, and the like, at ambient temperature for a period of about 3 h. Substituted chloroquinoline compounds of formula (XIII) are prepared from substituted quinolin-2(1H)-ones, under conditions previously described, for example, reaction with a chlorinating agent such as oxalyl chloride, sulfonyl chloride or phosphorus oxychloride, in the presence or absence of a catalytic amount of DMF, at temperatures ranging from 50° C. to about 70° C., for a period of about 1 hour. Compounds of Formula (I), where $R^1$ is a suitably substituted aryl or heteroaryl moiety, $R^2$ is —CH$_2$CO$_2$Et, and $R^3$ is —H, is obtained by reacting a compound of formula (XIII) with a palladium catalyst such as [1'1'-bis(diphenylphosphino)ferrocene]palladium(ll) dichloride dichloromethane adduct, in a solvent such as THF, and the like, N1,N1,N2,N2-tetramethylethane-1,2-diamine, sodium tetrahydroborate, at 25° C., for a period of 24 to 48 h.

such as DMF, ACN, DMSO, xylenes or a mixture thereof, at temperatures ranging from 0° C. to 140° C. Palladium-catalyzed carbonylation of 3-(benzyloxy)-7-bromo-1,5-naphthyridine (XV), employing methods known to one skilled in the art, for example, reacting 3-(benzyloxy)-7-bromo-1,5-naphthyridine with a palladium catalyst such as Pd$_2$(dba)$_3$, (Pd(allyl)$_2$Cl$_2$)$_2$, and the like, in a solvent such as toluene or xylenes, in an atmosphere of carbon monoxide provides ethyl 7-(benzyloxy)-1,5-naphthyridine-3-carboxylate. Removal of the benzyl protecting group under conditions known to one skilled in the art, for example, by catalytic hydrogenation conditions including a catalyst such as Pd black or Pd/C, a hydrogen source such as cyclohexadiene, ammonium formate, or gaseous H$_2$, in a solvent such as MeOH, EtOH, or EtOAc, provides ethyl 7-hydroxy-1,5-naphthyridine-3-carboxylate (XVI). Preferably, hydrogenation is performed using Pd/C and gaseous H$_2$ in a solvent such as MeOH or EtOH.

Compounds of formula (XVIII), are obtained by reacting substituted benzyl alcohols of formula (XVII), where $R^1$ is a suitably substituted aryl or heteroaryl moiety, with 3,7-dibromo-1,5-naphthyridine, in the presence of a base such as Cs$_2$CO$_3$, K$_2$CO$_3$, Na$_2$CO$_3$, NaH, or a mixture thereof, in a solvent such as NMP, DMA, DMF, DMSO or a mixture thereof, at temperatures ranging from 0° C. to 100° C., for a period of 3 to 24 h. Compounds of Formula (I), where Y is N, $R^2$ is CH$_2$CO$_2$Et, and $R^3$ is H, are obtained by palladium-catalyzed alkylation of intermediates of formula (XVIII). Alkylation reactions are performed in the presence of a palladium catalyst such as Pd$_2$(dba)$_3$, (Pd(allyl)$_2$Cl$_2$)$_2$, Pd(dba)$_2$, Scheme C

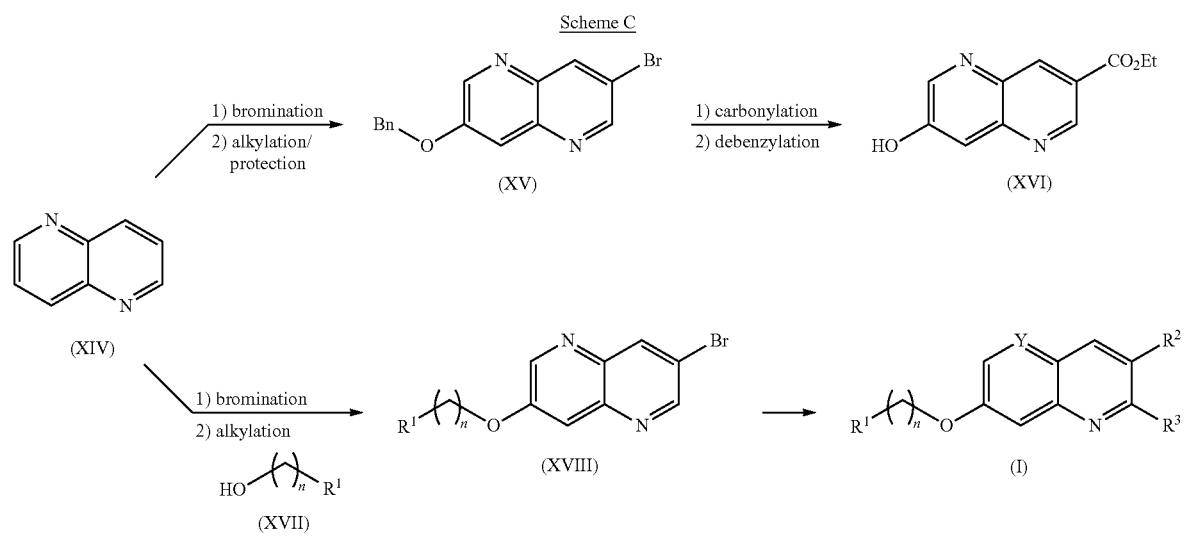

According to Scheme C, commercially available or synthetically accessible 1,5-naphthyridine (XIV) is treated with a brominating agent, such as, but not limited to, Br$_2$, in the presence of sodium acetate, in a solvent such as, but not limited to, acetic acid, at temperatures ranging from 23° C. to 60° C., preferably 60° C. for a period of about 24 h, preferably about 22 h, to provide 3,7-dibromo-1,5-naphthyridine. 3-(Benzyloxy)-7-bromo-1,5-naphthyridine (XV), is obtained by reacting 3,7-dibromo-1,5-naphthyridine, with sodium benzoxide, or a mixture of benzyl alcohol in the presence of a base such as Cs$_2$CO$_3$, K$_2$CO$_3$, DBU or NaH, in a solvent Pd(OAc)$_2$, and the like, a ligand such as t-Bu$_3$P, [(t-Bu)$_3$PH]BF$_4$, BINAP, and the like, and a base such as K$_3$PO$_4$, sodium tert-butoxide, Cs$_2$CO$_3$, LHMDS, NaOH, KOH, 4-DMAP, and the like, in a solvent such as DME, diethylmalonate, DMA, NMP, toluene, xylenes, DMF, or a mixture thereof, at a temperature from about 100° C. to about 140° C. Preferably, reactions are performed using Pd$_2$(dba)$_3$, [(t-Bu)$_3$PH]BF$_4$, and K$_3$PO$_4$, and 18-crown-6, in diethylmalonate, at a temperature of about 115° C. for 24 to 48 h; or (Pd(allyl)$_2$Cl$_2$)$_2$, BINAP, 4-DMAP, and potassium ethyl malonate, in xylenes, at 120° C. to 24 to 48 h.

Scheme D

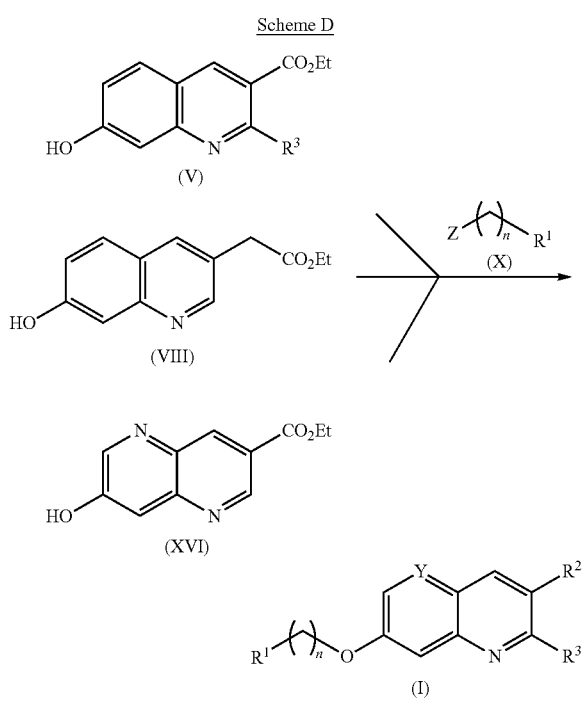

Compounds of Formula (I), where Y is CH, R² is —CO₂Et or —CH₂CO₂Et, and R³ is —H or —CH₃, are prepared according to Scheme D, by the reaction of compounds of formula (V) or (VIII) with commercially available or synthetically accessible substituted benzyl halide of formula (X), where Z is —Cl or —Br, n is 1 or 2, and R¹ is a suitably substituted aryl or heteroaryl moiety, in the presence of a base such as $Cs_2CO_3$, $K_2CO_3$, $Na_2CO_3$, NaH, LHMDS, and the like, in a polar aprotic solvent such as DMF, DMA, THF, NMP, DMSO, or a mixture thereof, at a temperature of about 25° C. for a period of 3 h. In a preferred embodiment, the base is $Cs_2CO_3$ and the solvent is DMF. Compounds of Formula (I), where Y is N, R³ is —H, and R² is CO₂Et, are prepared according to Scheme D, by the reaction of ethyl 7-hydroxy-1,5-naphthyridine-3-carboxylate (XVI) with commercially available or synthetically accessible substituted benzyl chlorides of formula (X), where n is 1 or 2 and R¹ is a suitably substituted aryl or heteroaryl moiety, in the presence of a base such as $Cs_2CO_3$, $K_2CO_3$, $Na_2CO_3$, NaH, and the like, in a polar aprotic solvent such as DMF, DMA, THF, or a mixture thereof, at a temperature of about 0° C. to 140° C. for a period of 2 to 24 h. In a preferred embodiment, the base is $Cs_2CO_3$ and the solvent is DMF. Transesterification of compounds of Formula (I), where Y is CH, R² is —CO₂Et or CH₂CO₂Et, under conditions known to one skilled in the art, for example, employing a base such as $K_2CO_3$, in a solvent such as MeOH, at ambient temperature, for about 8 to 24 h, provides compounds of Formula (I) where Y is CH, and R² is —CO₂CH₃ or CH₂CO₂CH₃. Transesterification can be conducted under acidic or basic conditions.

Dialkyl-esters of Formula (I), where Y is CH, and R² is —C(CH₃)₂CO₂Et are prepared by the reaction of esters of Formula (I) where Y is CH or N, and R² is —CH₂CO₂Et, with a base such as KHMDS, LiHMDS, and the like, an alkylating agent such as methyl iodide, and the like, in a solvent such as THF, dioxane, and the like, at a temperature of about 0° C. to ambient temperature for about 0.25 to 2 h. Dialkyl-amides of Formula (I), where Y is CH, and R² is —C(CH₃)₂CONH₂, are prepared from the saponification of esters of Formula (I), where Y is CH, and R² is —C(CH₃)₂CO₂Et employing conditions known to one skilled in the art. Subsequent chlorination employing methods previously described provides acid chlorides of Formula (I), where Y is CH, and R² is —C(CH₃)₂COCl, followed by amide formation, employing ammonium hydroxide, in a solvent such as THF, at ambient temperature, for about 8 to 24 h, provides compounds of Formula (I), where Y is CH, and R² is —C(CH₃)₂CONH₂.

Amides of Formula (I), where Y is CH or N, and R² is —CH₂CONH₂, —CONH₂, are prepared employing methods known to one skilled in the art, for example, reacting compounds of Formula (I) where Y is CH or N, and R² is —CH₂CO₂Et, —CO₂Et, with a suitable amine, such as ammonia, in a solvent such as MeOH, and the like, at temperatures ranging from 0° C. to 40° C., for about 0.5 to 48 h. Alternatively, amides of Formula (I), where Y is CH, and R² is —CONH(alkyl) are prepared in three steps from ester compounds of Formula (I), where Y is CH, and R² is —CO₂Et. Saponification of ester compounds of Formula (I), where R² is —CO₂Et, under conditions known to one skilled in the art, for example by reaction with a base such as LiOH, and the like, in a solvent such as THF, MeOH, or a mixture thereof, at a temperature of about 25° C., for about 2 to 48 h, provide intermediate acid compounds, where R² is —CO₂H. Acid chloride intermediate compounds, where R² is —COCl, are prepared under standard acid chloride formation conditions, for example, reaction of intermediate acid compounds, where R² is —CO₂H, with a chlorinating agent such as oxalyl chloride, thionyl chloride, or phosphorus oxychloride, in the presence or absence of a catalytic amount of DMF, in a solvent such as DCM, THF, or a mixture thereof, at ambient temperature for about 0.5 to 2 h. Reaction of intermediate acid chloride compounds, where R² is —COCl, with primary amines, such as, methylamine, tert-butyl (2-aminoethyl)(methyl)carbamate, or tert-butyl (2-aminoethyl)carbamate, and the like, in a solvent such as DCM, and the like, provide amide compounds of Formula (I), where Y is CH, and R² is —CONH(alkyl). In the case where a —BOC group is employed, it may be removed using HCl, TFA or p-toluenesulfonic acid, in a solvent such as MeOH, dioxane, or DCM. Preferably, a —BOC group is removed with TFA in DCM.

Compound 2-(7-((3-Chlorobenzyl)oxy)-2-oxo-1,2,3,4-tetrahydroquinolin-3-yl)acetamide is prepared from compounds of the formula (XII) with a suitable amine, such as ammonia, in a solvent such as MeOH, and the like, at temperatures ranging from 0° C. to 40° C., for about 0.5 to 48 h. Compound 2-(7-((3-chlorobenzyl)oxy)-2-oxo-1,2-dihydroquinolin-3-yl)acetamide is prepared from compounds of formula (XII) after oxidation, and reaction with an amine as described above.

Alcohols of Formula (I), where Y is CH or N, and R² is —CH₂CH₂OH, —C(CH₃)₂CH₂OH, or —CH₂OH are prepared employing methods known to one skilled in the art, for example, reacting compounds of Formula (I) where Y is CH or N, and R² is —CH₂CO₂Et, C(CH₃)₂CO₂Et, or —CO₂Et, with a reducing agent such as LAH, NaBH₄, and the like, in a solvent such as THF, diethyl ether, diglyme, and the like, at temperatures ranging from −78° C. to 80° C., for about 0.5 to 6 h.

Dialkyl-alcohols of Formula (I), where Y is CH or N, and R² is —CH₂C(CH₃)₂OH or —C(CH₃)₂OH are prepared by the reaction of esters of Formula (I) where Y is CH or N, and R² is —CH₂CO₂Et or —CO₂Et, under standard Grignard conditions, with methylmagnesium bromide, in a solvent such as THF, diethyl ether and the like, at a temperature of about 0° C., for about 0.25 to 2 h. Compounds of Formula (I), where Y is CH, and R² is —C(CH₃)₂OH are oxidized, under standard oxidation conditions, with 3-chloroperoxybenzoic acid, in a solvent such as DCM, at temperatures of about 0° C. to room temperature, to provide N-oxide compounds of Formula (I).

Fluoro compounds of Formula (I), where Y is CH or N, and R² is —C(CH₃)₂F are prepared by the reaction of alcohols of Formula (I), where Y is CH or N, and R² is —C(CH₃)₂OH, employing fluorinating conditions such, but not limited to, reaction with XtalFluor®, triethylamine trihydrofluoride, TEA, in a solvent such as DCM, and the like, at a temperature of about 0° C., for about 1 to 3 h.

Nitrile compounds of Formula (I), where Y is N, and R² is —CH₂CN, are prepared from alcohols of Formula (I), where Y is N, and R² is —CH₂OH in two steps. Alcohols of Formula (I), where Y is N, and R² is —CH₂OH, are mesylated, under standard mesylation conditions, for example, by reaction with methanesulfonyl chloride, a base such as TEA, DIPEA, and the like, in a solvent such as DCM, THF, and the like, at ambient temperature, for about 2 to 24 h. Subsequent reaction of mesylated compounds of Formula (I) with sodium cyanide, in a solvent such as DMSO, at temperatures of 60° C. to 100° C., for about 2 to 48 h, provides nitrile compounds of Formula (I), where Y is N, and R² is —CH₂CN.

Amine compounds of Formula (I), where Y is CH, and R² is —CH₂NH₂, are prepared from alcohols of Formula (I), where Y is CH, and R² is —CH₂OH in two steps. Alcohols of Formula (I), where Y is CH, and R² is —CH₂OH, are mesylated, under standard mesylation conditions as previously described. Subsequent reaction of mesylated compounds of Formula (I) with ammonia, in a solvent such as MeOH, at temperatures of 80° C. to 120° C., for about 1 to 6 h, provide amine compounds of Formula (I), where Y is CH, and R² is —CH₂NH₂.

Keto compounds of Formula (I), where Y is CH, and R² is —C(O)CH₃, are prepared from ester compounds of Formula (I), where Y is CH, and R² is —CO₂Et. Saponification of ester compounds of Formula (I) where Y is CH, and R² is —CO₂Et, under conditions known to one skilled in the art, for example, employing sodium hydroxide, in a solvent such as MeOH, THF, or a mixture thereof, at ambient temperature, for about 1-4 h, provides carboxylate intermediates where R² is —CO₂H. Acid chloride intermediate compounds, where R² is —COCl, are prepared as previously described, for example, reaction of intermediate acid compounds, where R² is —CO₂H, with a chlorinating agent such as oxalyl chloride, with or without a catalytic amount of DMF, in a solvent such as DCM, THF, or a mixture thereof, at ambient temperature, for about 0.5 to 2 h. Following standard Weinreb ketone synthesis, acid chloride intermediates, where R² is —COCl are first converted to the Weinreb amide, where R² is —C(O)N(CH₃)OCH₃, under conditions known to one skilled in the art, followed by treatment with an organometallic reagent, such as methyl magnesium bromide, in a solvent such as THF, diethyl ether, or a mixture thereof, at a temperatures of about 0° C., for about 0.5 to 4 h, to provide keto compounds of Formula (I), where Y is CH, and R² is —C(O)CH₃.

Alcohols of Formula (I), where Y is CH, and R² is —CH(OH)CH₃, are prepared by reducing keto compounds of Formula (I), where Y is CH, and R² is —C(O)CH₃, with a reducing agent such as sodium borohydride, lithium borohydride, or a mixture thereof, in a solvent such as THF, diethyl ether, and the like, at temperatures ranging from 0° C. to ambient temperature. Enantiomerically pure alcohols of Formula (I), where Y is CH, and R² is —CH(OH)CH₃, are prepared by reducing keto compounds of Formula (I), where Y is CH, and R² is —C(O)CH₃, with an organo-boron catalyst such as (R) or (S) 2-methyl-CBS-oxazaborolidine, a reducing agent such as borane, in a solvent such as toluene, THF, and the like, at temperatures ranging from −20° C. to ambient temperature.

Ethers of Formula (I), where Y is CH, and R² is —CH₂OCH₃, are prepared employing methods known to one skilled in the art, for example, by reacting compounds of Formula (I) where Y is CH, and R² is —CH₂OH, with a suitable base, such as sodium hydride, an alkylating agent such as methyl iodide, in a solvent such as DMF, and the like, at temperatures ranging from 0° C. to 100° C.

Cycloalkyl compounds of Formula (I), where Y is CH or N, and R² is C₃₋₆cycloalkyl)OH, may be prepared from acid chlorides of compounds of Formula (I), where Y is CH or N, and R² is —CO₂Cl. Acid chlorides of Formula (I), prepared according to methods previously described, may be treated with ClCH₂I, MeLi and LiBr, and subsequently Li, as described in Barluenga et al., *Synthesis,* 1987, 6, 584-586, to provide cycloalkyl compounds of Formula (I), where Y is CH or N and R² is

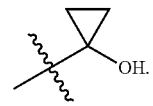

Fluoro compounds of Formula (I), where Y is CH or N, and R² is —CF₂CO₂Et may be prepared by the reaction of esters of Formula (I), where Y is CH or N, and R² is —CH₂CO₂Et, by reaction with a base such as lithium bis(trimethylsilyl)amide, and the like, in a solvent such as THF, at a temperature of about −70° C., and a fluorinating agent such as n-fluorobis(phenylsulfonyl)amine, for about 1 to 3 h at a temperature of about 0° C.

Compounds of Formula (I) may be converted to their corresponding salts using methods known to those skilled in the art. For example, compounds of Formula (I) may be treated with TFA, HCl, maleic acid, or citric acid in a solvent such as Et₂O, DCM, THF, or MeOH to provide the corresponding salt forms.

Compounds prepared according to the schemes described above may be obtained as single enantiomers, diastereomers, or regioisomers, by enantio-, diastereo-, or regiospecific synthesis, or by resolution. Where compounds according to this invention have at least one chiral center, they may accordingly exist as enantiomers. Where compounds possess two or more chiral centers, they may additionally exist as diastereomers. It is to be understood that all such isomers and mixtures thereof are encompassed within the scope of the present invention. Compounds prepared according to the schemes above may alternately be obtained as racemic (1:1) or non-racemic (not 1:1) mixtures of mixtures as diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

Protocols

In obtaining the compounds described in the examples below, and the corresponding analytical data, the following experimental and analytical protocols were followed unless otherwise indicated.

Unless otherwise stated, reaction mixtures were magnetically stirred at room temperature (rt) under nitrogen atmosphere. Where solutions were "dried", they were generally dried over a drying agent such as $Na_2SO_4$ or $MgSO_4$. Where mixtures, solutions, and extracts were "concentrated", they were typically concentrated on a rotary evaporator under reduced pressure.

Reactions under microwave irradiation conditions were carried out in a CEM Discover-SP with Activent microwave reaction apparatus, model number 909150, or Biotage Initiator, model number 355302.

Normal-phase flash column chromatography (FCC) was performed on silica gel ($SiO_2$) using packed or prepackaged cartridges, eluting with the indicated solvents.

LC/MS were obtained on a Waters 2695 Separations Unit, 2487 Dual Absorbance Detector, Micromass ZQ fitted with ESI Probe, or a Waters Acquity™ Ultra Performance LC (UPLC) Photodiode Array Detector (PDA).

Nuclear magnetic resonance (NMR) spectra were obtained in a Varian 400 MHz or Bruker 400 MHz NMR. Samples were analyzed in either deuterated chloroform ($CDCl_3$), methanol-$d_4$ ($CD_3OD$), or dimethyl sulfoxide-$d_6$ ($DMSO-d_6$). For $CDCl_3$ samples, tetramethylsilane (TMS) was used as an internal standard with the TMS resonance set to a chemical shift of 0.00 ppm for $^1H$ NMR spectra. For $CD_3OD$ the residual central resonance peak at 3.31 for $^1H$ was used for chemical shift assignment and for $DMSO-d_6$ the residual central resonance peak at 2.50 ppm for $^1H$ was used for chemical shift assignment. The format of the $^1H$ NMR data below is: chemical shift in ppm downfield the tetramethylsilane reference (multiplicity, coupling constant J in Hz, integration).

Chemical names were generated using ChemDraw Ultra 12.0 (CambridgeSoft Corp., Cambridge, Mass.) or ChemAxon.

Intermediates

Intermediate 1. Ethyl 7-hydroxyquinoline-3-carboxylate

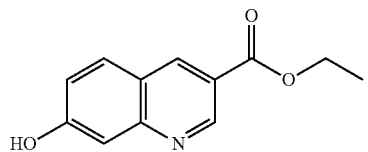 [SMILES: CCOC(=O)c1cnc2cc(O)ccc2c1]

Step A. Diethyl 2-(((3-methoxyphenyl)amino)methylene)malonate. Diethyl ethoxymethylenemalonate (5.00 g, 40.6 mmol) and m-anisidine (8.13 mL, 40.6 mmol) were mixed and heated at 125° C. for 3 h. After cooling to ambient temperature, residual solvent was removed under reduced pressure and dried under high vacuum to afford the title compound as a yellow oil (11.81 g, 99%). $^1H$ NMR (400 MHz, $CDCl_3$) δ 11.57 (d, J=13.7 Hz, 1H), 9.11 (d, J=13.7 Hz, 1H), 7.90-7.83 (m, 1H), 7.31 (ddd, J=15.5, 8.2, 2.2 Hz, 2H), 7.25 (d, J=2.3 Hz, 1H), 4.90 (q, J=7.0 Hz, 2H), 4.84 (q, J=7.3 Hz, 2H), 4.42 (s, 3H), 1.98 (t, J=7.0 Hz, 3H), 1.92 (t, J=7.0 Hz, 3H). [M+H]=294.3.

Step B. Ethyl 4-hydroxy-7-methoxyquinoline-3-carboxylate. To a solution of boiling Dowtherm™ (100 mL) was added diethyl 2-(((3-methoxyphenyl)amino)methylene)malonate (20.0 g, 68.3 mmol). After 15 minutes the reaction was cooled to ambient temperature and poured into hexanes (500 mL). The precipitate was collected by filtration and dried under high vacuum to yield the title compound as a brown solid (15.2 g, 90%). $^1H$ NMR (400 MHz, $DMSO-d_6$) δ 12.09 (d, J=5.9 Hz, 1H), 8.47 (d, J=6.7 Hz, 1H), 8.03 (d, J=9.4 Hz, 1H), 7.04-6.97 (m, 2H), 4.18 (q, J=7.0 Hz, 2H), 3.85 (s, 3H), 1.25 (t, J=7.2 Hz, 4H).

Step C. Ethyl 4-chloro-7-methoxyquinoline-3-carboxylate. To a solution of ethyl 4-hydroxy-7-methoxyquinoline-3-carboxylate (2.72 g, 11.0 mmol) in chloroform (100 mL) was added oxalyl chloride (2.93 mL, 33.0 mmol) followed by 5 drops of DMF. The reaction was heated at 65° C. for 2.5 h before cooling to ambient temperature. The reaction mixture was poured into saturated $NaHCO_3$ (aq.) solution and the organics were extracted with DCM. The combined organics were dried over $MgSO_4$, filtered and concentrated under reduced pressure to afford the title compound as a yellow solid (2.69 g, 92%). $^1H$ NMR (400 MHz, $CDCl_3$) δ 9.20 (s, 1H), 8.33 (d, J=9.4 Hz, 1H), 7.58 (br. s., 1H), 7.37 (d, J=9.0 Hz, 1H), 4.48 (q, J=6.8 Hz, 2H), 4.01 (s, 3H), 1.45 (t, J=7.0 Hz, 3H). [M+H]=266.2.

Step D. Ethyl 7-methoxyquinoline-3-carboxylate. To a solution of ethyl 4-chloro-7-methoxyquinoline-3-carboxylate (1.24 g, 4.67 mmol) in a mixture of EtOAc (30 mL) and ethanol (30 mL) was added 10% Pd/C (10 mg). The flask was evacuated and filled with nitrogen three times and evacuated and filled with hydrogen three times and stirred overnight. After filtration through a plug of silica the reaction mixture was concentrated onto silica. Purification by FCC ($SiO_2$, 0-10% MeOH/DCM) afforded the title compound as a brown solid (955 mg, 89%). $^1H$ NMR (400 MHz, $CDCl_3$) δ 9.37 (d, J=2.0 Hz, 1H), 8.75 (d, J=2.0 Hz, 1H), 7.80 (d, J=9.0 Hz, 1H), 7.47 (d, J=2.3 Hz, 1H), 7.27 (d, J=2.3 Hz, 1H), 4.45 (q, J=7.0 Hz, 2H), 4.01-3.93 (m, 3H), 1.44 (t, J=7.2 Hz, 3H). [M+H]=232.2.

Step E. 7-Hydroxyquinoline-3-carboxylic acid. Ethyl 7-methoxyquinoline-3-carboxylate (7.03 g, 30.4 mmol) was dissolved in HBr (48% aq., 150 mL) and was heated at 105° C. for 88.5 h. The reaction was cooled to ambient temperature and the precipitate was collected by filtration to afford the title compound as a brown solid (5.2 g, 90%). $^1H$ NMR (400 MHz, $DMSO-d_6$) δ 12.05-11.67 (m, 1H), 9.49 (d, J=2.0 Hz, 1H), 9.43 (s, 1H), 8.39 (d, J=9.8 Hz, 1H), 7.55-7.51 (m, 2H). [M+H]=190.2.

Step F. Ethyl 7-hydroxyquinoline-3-carboxylate. To a solution of 7-hydroxyquinoline-3-carboxylic acid (273 mg, 1.44 mmol) in ethanol (6.0 mL) was added $H_2SO_4$ (60 μL). The reaction was heated at 75° C. overnight. After cooling to ambient temperature the reaction was concentrated onto silica gel. Purification by FCC ($SiO_2$, 0-10% MeOH/DCM) afforded the title compound as a yellow solid (181 mg, 58%). $^1H$ NMR (400 MHz, $DMSO-d_6$) δ 10.70 (s, 1H), 9.20 (d, J=2.3 Hz, 1H), 8.86 (d, J=2.0 Hz, 1H), 8.08 (d, J=8.6 Hz, 1H), 7.33 (d, J=2.7 Hz, 1H), 7.28 (dd, J=9.0, 2.3, Hz, 1H), 4.41 (q, J=7.3 Hz, 2H), 1.39 (t, J=7.0 Hz, 3H). [M+H]=218.2.

Intermediate 2. Ethyl 2-(7-hydroxyquinolin-3-yl)acetate

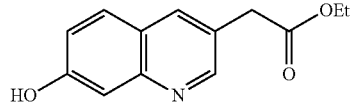 [SMILES: CCOC(=O)Cc1cnc2cc(O)ccc2c1]

Step A: Ethyl 4-((3-methoxyphenyl)amino)-4-oxobutanoate. To a solution of m-anisidine (10 g, 81.3 mmol) in THF (240 mL) was added Et₃N (22 mL, 217.8 mmol) followed by ethyl succinyl chloride (11.14 g, 67.9 mmol). The reaction mixture was stirred at ambient temperature for 15 minutes. The reaction was diluted with H₂O and EtOAc and the organic layer was separated. The organic layers were washed with H₂O, 10% HCl (aq), sat. NaHCO₃ (aq) and brine, dried over MgSO₄ and concentrated under reduced pressure to give the title compound as a pale yellow solid (17.5 g, 86%). $^1$H NMR (400 MHz, CDCl₃) δ 7.62-7.56 (m, 1H), 7.32-7.28 (m, 1H), 7.19 (t, J=8.0 Hz, 1H), 6.95 (d, J=8.2 Hz, 1H), 6.65 (dd, J=8.2, 2.0 Hz, 1H), 4.17 (d, J=7.0 Hz, 2H), 3.80 (s, 3H), 2.81-2.70 (m, 2H), 2.70-2.60 (m, 2H), 1.26 (t, J=7.2 Hz, 3H). [M+H]=252.3.

Step B. Ethyl 2-(2-chloro-7-methoxyquinolin-3-yl)acetate and ethyl 2-(2-chloro-5-methoxyquinolin-3-yl)acetate. DMF (8.0 mL, 95.9 mmol) was cooled to 0° C. and phosphoryl chloride (44 mL, 472 mmol) was slowly added and stirred at 0° C. for 5 minutes. Ethyl 4-((3-methoxyphenyl)amino)-4-oxobutanoate (17.5 g, 69.7 mmol) was added in one portion and stirred for 20 minutes at ambient temperature, the reaction was then heated at 75° C. for 1.5 h. The reaction mixture was concentrated under reduced pressure to yield a crude mixture of the title compounds as a brown oil. This was used directly in the next step with no further purification. [M+H]=280.19.

Step C. Ethyl 2-(7-methoxyquinolin-3-yl)acetate. To a solution of a crude mixture of ethyl 2-(2-chloro-7-methoxyquinolin-3-yl)acetate and ethyl 2-(2-chloro-5-methoxyquinolin-3-yl)acetate in EtOAc (200 mL) and EtOH (200 mL) was added 10% Pd/C (50 mg, 0.47 mmol). The reaction mixture was placed under an atmosphere of hydrogen and stirred at ambient temperature for 3 days. The crude reaction mixture was filtered through silica and concentrated to afford a brown oil. Purification by FCC (SiO₂, 0-5%, MeOH/DCM) yielded the title compound as a light brown solid (6.0 g, 35% over 2 steps). $^1$H NMR (400 MHz, CDCl₃) δ 8.76 (d, J=2.0 Hz, 1H), 8.00 (d, J=2.3 Hz, 1H), 7.67 (d, J=8.6 Hz, 1H), 7.41 (d, J=2.3 Hz, 1H), 7.20 (dd, J=9.0, 2.3 Hz, 1H), 4.18 (q, J=7.2 Hz, 2H), 3.95 (s, 3H), 3.76 (s, 2H), 1.26 (t, J=6.8 Hz, 3H). [M+H]=246.2.

Step D. Ethyl 2-(7-hydroxyquinolin-3-yl)acetate. Ethyl 2-(7-methoxyquinolin-3-yl)acetate (6 g, 24.5 mmol) was dissolved in HBr (48% aq., 40 mL) and heated at 105° C. for 4 days. The reaction mixture was concentrated to a brown oil, which was dissolved in EtOH (50 mL) and H₂SO₄ (200 µL) was added. The reaction mixture was heated at 75° C. for 2 h. The solution was concentrated under reduced pressure to an oil, which was quenched by the addition of saturated sodium carbonate solution. The organics were extracted with DCM, combined and washed with brine, and concentrated onto silica. Purification by FCC (SiO₂, 0-5%, MeOH/DCM) afforded the title compound as a light brown solid (2.19 g, 39%). $^1$H NMR (400 MHz, DMSO-d₆) δ 10.17 (s, 1H), 8.69 (d, J=2.0 Hz, 1H), 8.11 (d, J=2.0 Hz, 1H), 7.82 (d, J=8.6 Hz, 1H), 7.27 (d, J=2.3 Hz, 1H), 7.20 (dd, J=8.8, 2.5 Hz, 1H), 4.15 (q, J=7.0 Hz, 2H), 3.88 (s, 2H), 1.24 (t, J=7.0 Hz, 3H). [M+H]=322.2.

Intermediate 3. 3,7-Dibromo-1,5-naphthyridine

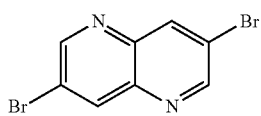

1,5-Naphthyridine (30.80 g, 236.7 mmol) and sodium acetate (38.83 g, 473.3 mmol) were dissolved in acetic acid (236.7 mL) and heated to 60° C. A solution of bromine (25.6 mL, 496.9 mmol) in acetic acid (35 mL) was added dropwise over 30 minutes. The solution was allowed to stir for 22 h at 60° C. The reaction was cooled to ambient temperature then diluted with water (250 mL) and basified with 4 N NaOH (aq.) (300 mL), where upon addition of base, a beige precipitate formed. The precipitate was collected by filtration then washed with water, MeOH, and acetone. The remaining solid (54.7 g) was recrystallized from chloroform (1.36 L) to give the title compound as a pure, cream colored solid (30 g, 44%). $^1$H NMR (400 MHz, CDCl₃) δ 9.08-8.95 (m, 2H), 8.62 (dd, J=2.2, 0.7 Hz, 1H), 8.46-8.35 (m, 1H), 8.23 (d, J=8.8 Hz, 1H), 7.79 (d, J=8.8 Hz, 1H), 7.69 (dd, J=8.5, 4.3 Hz, 1H). [M+H]=286.9.

Intermediate 4. Ethyl 7-hydroxy-1,5-naphthyridine-3-carboxylate

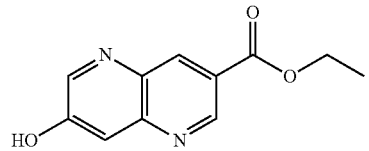

Step A: 3-(Benzyloxy)-7-bromo-1,5-naphthyridine. To a solution of benzyl alcohol (2.25 g, 20.8 mmol) in DMF (25 mL) was added NaH (60% in mineral oil, 0.83 g, 20.8 mmol). The resulting mixture was heated to 60° C. for 10 minutes and was added to 3,7-dibromo-1,5-naphthyridine (Intermediate 3, 5.0 g, 17.4 mmol) in DMF (25.0 mL) at 100° C. The resulting mixture was stirred over night at 100° C., cooled, and concentrated under reduced pressure. Water (50 mL) was added and the aqueous layer was washed with DCM (3×50 mL). The organic layers were combined, dried over Na₂SO₄, filtered and concentrated under reduced pressure. Purification (FCC, SiO₂, DCM/petroleum ether, 1:1) afforded the title compound as a white solid (2.0 g, 36.7%).

Step B. Ethyl 7-(benzyloxy)-1,5-naphthyridine-3-carboxylate. A mixture of 3-(benzyloxy)-7-bromo-1,5-naphthyridine (30.0 g, 95.5 mmol), Et₃N (19.47 g, 193 mmol), Pd(PhCN)₂Cl₂ (1.2 g, 3.13 mmol) and dppf (5.28 g, 9.5 mmol) in EtOH (500 mL) was pressurized to 15 bars with CO gas. Then the mixture was heated at 140° C. for 24 h. After cooling to ambient temperature, the solvent was removed under reduced pressure. Purification (FCC, SiO₂, DCM/EtOAc, 1:1) afforded the title compound as a yellow solid (14 g, 67%). [M+H]=309.3.

Step C: Ethyl 7-hydroxy-1,5-naphthyridine-3-carboxylate. The title compound was prepared in a manner analogous to Intermediate 2, Step C, substituting ethyl 7-(benzyloxy)-1,5-naphthyridine-3-carboxylate for ethyl 2-(2-chloro-7-methoxyquinolin-3-yl)acetate. $^1$H NMR (400 MHz, DMSO-d₆) δ 11.31 (br s, 1H), 9.28 (d, J=2.0 Hz, 1H), 8.90-8.61 (m, 2H), 7.62 (d, J=2.0 Hz, 1H), 4.41 (q, J=7.1 Hz, 2H), 1.38 (t, J=7.2 Hz, 3H). [M+H]=219.2.

EXEMPLARY COMPOUNDS

Example 1

Ethyl 7-[(4-chlorophenyl)methoxy]quinoline-3-carboxylate

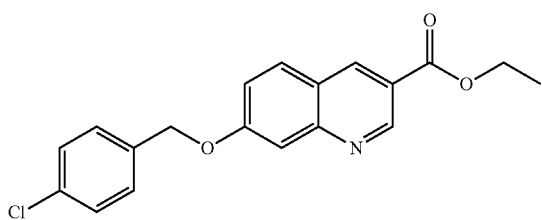 [SMILES: CCOC(=O)c1cnc2cc(OCc3ccc(Cl)cc3)ccc2c1]

To a solution of ethyl 7-hydroxyquinoline-3-carboxylate (Intermediate 1, 50 mg, 0.23 mmol) in DMF (1.15 mL) was added $Cs_2CO_3$ (150 mg, 0.46 mmol) and 4-chlorobenzyl chloride (41 mg, 0.25 mmol). The reaction was stirred overnight at ambient temperature. The reaction mixture was loaded directly onto a column and purification (FCC, $SiO_2$, EtOAc/hexanes, 0-20%) afforded the title compound as a white solid (50 mg, 63%). $^1$H NMR (400 MHz, $CDCl_3$) δ 9.37 (d, J=2.3 Hz, 1H), 8.74 (d, J=2.0 Hz, 1H), 7.83 (d, J=9.0 Hz, 1H), 7.50 (d, J=2.3 Hz, 1H), 7.45-7.35 (m, 4H), 7.34-7.29 (m, 1H), 5.20 (s, 2H), 4.45 (q, J=7.3 Hz, 2H), 1.44 (t, J=7.0 Hz, 3H). [M+H]=342.3.

Example 2

Ethyl 7-[(4-fluorophenyl)methoxy]quinoline-3-carboxylate

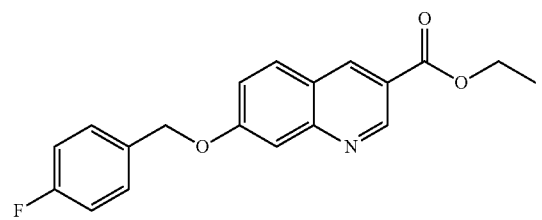 [SMILES: CCOC(=O)c1cnc2cc(OCc3ccc(F)cc3)ccc2c1]

The title compound was prepared in a manner analogous to Example 1, substituting 4-fluorobenzyl chloride for 4-chlorobenzyl chloride. $^1$H NMR (400 MHz, $CDCl_3$) δ 9.37 (d, J=2.0 Hz, 1H), 8.74 (d, J=2.3 Hz, 1H), 7.82 (d, J=9.0 Hz, 1H), 7.52 (d, J=2.3 Hz, 1H), 7.46 (dd, J=8.4, 5.7 Hz, 2H), 7.31 (dd, J=9.0, 2.3, Hz, 1H), 7.09 (t, J=8.8 Hz, 2H), 5.19 (s, 2H), 4.45 (q, J=7.0 Hz, 2H), 1.44 (t, J=7.2 Hz, 3H). [M+H]=326.2.

Example 3

Ethyl 7-[(3-chlorophenyl)methoxy]quinoline-3-carboxylate

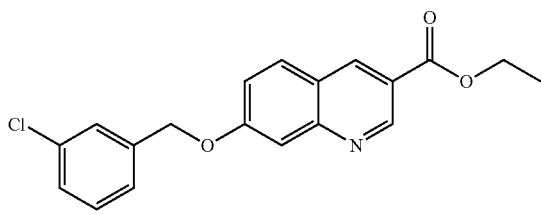 [SMILES: CCOC(=O)c1cnc2cc(OCc3cccc(Cl)c3)ccc2c1]

The title compound was prepared in a manner analogous to Example 1, substituting 3-chlorobenzyl chloride for 4-chlorobenzyl chloride. $^1$H NMR (400 MHz, $CDCl_3$) δ 9.38 (d, J=2.0 Hz, 1H), 8.76 (d, J=2.0 Hz, 1H), 7.85 (d, J=9.0 Hz, 1H), 7.51 (d, J=2.7 Hz, 2H), 7.40-7.29 (m, 4H), 5.22 (s, 2H), 4.47 (q, J=7.3 Hz, 2H), 1.46 (t, J=7.0 Hz, 3H). [M+H]=342.3.

Example 4

Ethyl 7-[(3-fluorophenyl)methoxy]quinoline-3-carboxylate

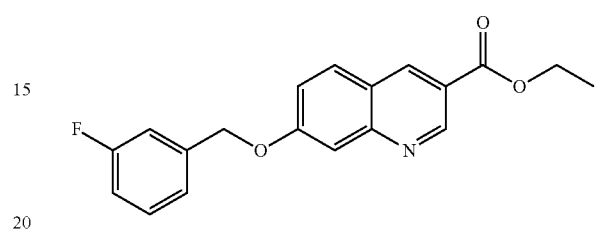

The title compound was prepared in a manner analogous to Example 1, substituting 3-fluorobenzyl chloride for 4-chlorobenzyl chloride. $^1$H NMR (400 MHz, $CDCl_3$) δ 9.37 (d, J=2.0 Hz, 1H), 8.75 (d, J=1.6 Hz, 1H), 7.83 (d, J=9.0 Hz, 1H), 7.50 (d, J=2.3 Hz, 1H), 7.43-7.20 (m, 4H), 7.07-6.99 (m, 1H), 5.23 (s, 2H), 4.45 (q, J=7.3 Hz, 2H), 1.44 (t, J=7.2 Hz, 3H). [M+H]=326.3.

Example 5

Ethyl 7-((3-(trifluoromethyl)benzyl)oxy)quinoline-3-carboxylate

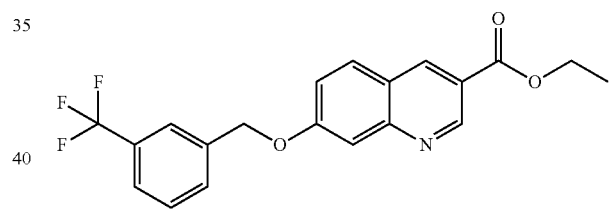

The title compound was prepared in a manner analogous to Example 1, substituting 3-trifluoromethylbenzyl chloride for 4-chlorobenzyl chloride. $^1$H NMR (400 MHz, $CDCl_3$) δ 9.38 (d, J=2.0 Hz, 1H), 8.76 (d, J=1.6 Hz, 1H), 7.86 (d, J=9.0 Hz, 1H), 7.76 (s, 1H), 7.71-7.49 (m, 4H), 7.36 (dd, J=9.0, 2.7 Hz, 1H), 5.28 (s, 2H), 4.47 (q, J=7.2 Hz, 2H), 1.45 (t, J=7.2 Hz, 3H). [M+H]=376.3.

Example 6

Ethyl 7-((4-(trifluoromethyl)benzyl)oxy)quinoline-3-carboxylate

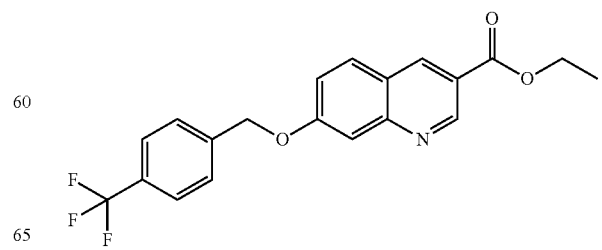

The title compound was prepared in a manner analogous to Example 1, substituting 4-trifluoromethylbenzyl chloride for 4-chlorobenzyl chloride. ¹H NMR (400 MHz, CDCl₃) δ 9.38 (d, J=2.3 Hz, 1H), 8.76 (d, J=1.6 Hz, 1H), 7.85 (d, J=9.0 Hz, 1H), 7.70-7.57 (m, 4H), 7.51 (d, J=2.3 Hz, 1H), 7.35 (dd, J=9.0, 2.3 Hz, 1H), 5.30 (s, 2H), 4.46 (q, J=7.3 Hz, 2H), 1.45 (t, J=7.0 Hz, 3H). [M+H]=376.2.

Example 7

Ethyl 7-((3-methylbenzyl)oxy)quinoline-3-carboxylate

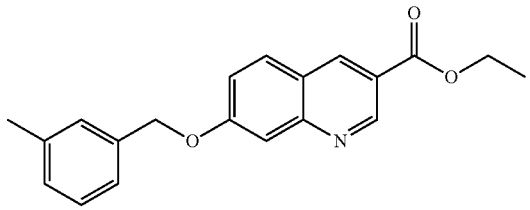 [SMILES: CCOC(=O)c1cnc2cc(OCc3cccc(C)c3)ccc2c1]

The title compound was prepared in a manner analogous to Example 1, substituting 3-methylbenzyl chloride for 4-chlorobenzyl chloride. ¹H NMR (400 MHz, CDCl₃) δ 9.38 (d, J=2.0 Hz, 1H), 8.75 (d, J=2.0 Hz, 1H), 7.83 (d, J=9.0 Hz, 1H), 7.55 (d, J=2.3 Hz, 1H), 7.36-7.28 (m, 4H), 7.17 (d, J=5.9 Hz, 1H), 5.20 (s, 2H), 4.46 (q, J=7.0 Hz, 2H), 2.39 (s, 3H), 1.45 (t, J=7.0 Hz, 3H). [M+H]=322.2.

Example 8

Ethyl 7-((4-methylbenzyl)oxy)quinoline-3-carboxylate

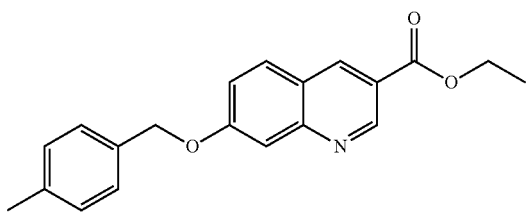 [SMILES: CCOC(=O)c1cnc2cc(OCc3ccc(C)cc3)ccc2c1]

The title compound was prepared in a manner analogous to Example 1, substituting 4-methylbenzyl chloride for 4-chlorobenzyl chloride. ¹H NMR (400 MHz, CDCl₃) δ 9.37 (d, J=2.0 Hz, 1H), 8.74 (d, J=2.0 Hz, 1H), 7.81 (d, J=9.0 Hz, 1H), 7.54 (d, J=2.3 Hz, 1H), 7.38 (d, J=8.2 Hz, 2H), 7.32 (dd, J=8.8, 2.5 Hz, 1H), 7.22 (d, J=7.8 Hz, 2H), 5.19 (s, 2H), 4.46 (q, J=7.2 Hz, 2H), 2.37 (s, 3H), 1.45 (t, J=7.2 Hz, 3H). [M+H]=322.2.

Example 9

Ethyl 7-((3-methoxybenzyl)oxy)quinoline-3-carboxylate

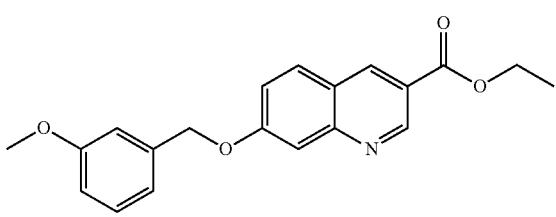 [SMILES: CCOC(=O)c1cnc2cc(OCc3cccc(OC)c3)ccc2c1]

The title compound was prepared in a manner analogous to Example 1, substituting 3-methoxybenzyl chloride for 4-chlorobenzyl chloride. ¹H NMR (400 MHz, CDCl₃) δ 9.38 (d, J=2.3 Hz, 1H), 8.75 (d, J=2.0 Hz, 1H), 7.83 (d, J=9.0 Hz, 1H), 7.54 (d, J=2.3 Hz, 1H), 7.38-7.30 (m, 2H), 7.10-7.00 (m, 2H), 6.95-6.87 (m, 1H), 5.22 (s, 2H), 4.47 (q, J=7.3 Hz, 2H), 3.83 (s, 3H), 1.46 (t, J=7.2 Hz, 3H). [M+H]=338.2.

Example 10

Ethyl 7-((4-methoxybenzyl)oxy)quinoline-3-carboxylate

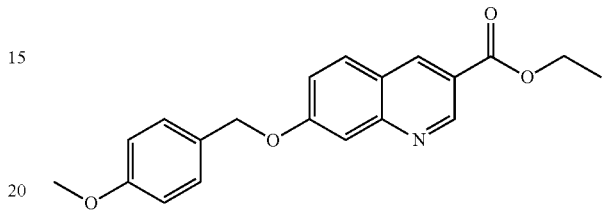

The title compound was prepared in a manner analogous to Example 1, substituting 4-methoxybenzyl chloride for 4-chlorobenzyl chloride. ¹H NMR (400 MHz, CDCl₃) δ 9.37 (d, J=2.0 Hz, 1H), 8.74 (d, J=2.0 Hz, 1H), 7.81 (d, J=9.0 Hz, 1H), 7.55 (d, J=2.3 Hz, 1H), 7.42 (d, J=8.6 Hz, 2H), 7.33-7.27 (m, 1H), 6.96-6.92 (m, 2H), 5.16 (s, 2H), 4.46 (q, J=7.0 Hz, 2H), 3.82 (s, 3H), 1.45 (t, J=7.2 Hz, 3H). [M+H]=338.4.

Example 11

Ethyl 7-((4-nitrobenzyl)oxy)quinoline-3-carboxylate

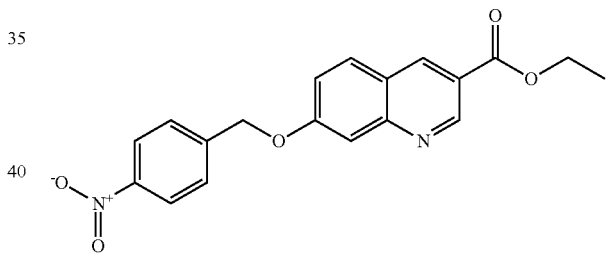

The title compound was prepared in a manner analogous to Example 1, substituting 4-nitrobenzyl bromide for 4-chlorobenzyl chloride. ¹H NMR (400 MHz, CDCl₃) δ 9.41-9.35 (m, 1H), 8.77 (d, J=2.0 Hz, 1H), 8.28 (d, J=7.8 Hz, 2H), 7.87 (d, J=9.0 Hz, 1H), 7.67 (d, J=8.2 Hz, 2H), 7.49 (d, J=2.0 Hz, 1H), 7.37 (dd, J=9.0, 2.3 Hz, 1H), 5.35 (s, 2H), 4.51-4.41 (m, 2H), 1.45 (dt, J=7.1, 1.0 Hz, 3H). [M+H]=353.3.

Example 12

Ethyl 7-((4-fluoro-3-(trifluoromethyl)benzyl)oxy)quinoline-3-carboxylate

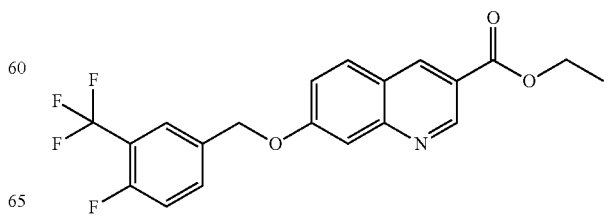

The title compound was prepared in a manner analogous to Example 1, substituting 4-fluoro-3-trifluorobenzyl chloride for 4-chlorobenzyl chloride. ¹H NMR (400 MHz, CDCl₃) δ 9.39 (d, J=2.3 Hz, 1H), 8.77 (d, J=2.0 Hz, 1H), 7.87 (d, J=9.0 Hz, 1H), 7.55 (s, 1H), 7.50 (d, J=2.3 Hz, 1H), 7.44-7.29 (m, 3H), 5.28 (s, 2H), 4.47 (q, J=7.0 Hz, 2H), 1.46 (t, J=7.2 Hz, 3H). [M+H]=394.3.

Example 13

Ethyl 7-((3-fluoro-5-(trifluoromethyl)benzyl)oxy)quinoline-3-carboxylate

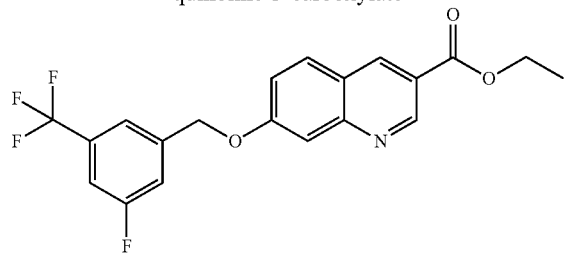

The title compound was prepared in a manner analogous to Example 1, substituting 3-trifluoro-5-fluorobenzyl bromide for 4-chlorobenzyl chloride. ¹H NMR (400 MHz, CDCl₃) δ 9.39 (d, J=2.3 Hz, 1H), 8.77 (d, J=2.0 Hz, 1H), 7.86 (d, J=9.0 Hz, 1H), 7.75 (d, J=6.7 Hz, 1H), 7.71-7.64 (m, 1H), 7.51 (d, J=2.3 Hz, 1H), 7.34 (dd, J=2.5, 8.8 Hz, 1H), 7.28-7.26 (m, 1H), 5.23 (s, 2H), 4.47 (q, J=7.0 Hz, 2H), 1.45 (t, J=7.2 Hz, 3H). [M+H]=394.3.

Example 14

Ethyl 7-((3,4-difluorobenzyl)oxy)quinoline-3-carboxylate

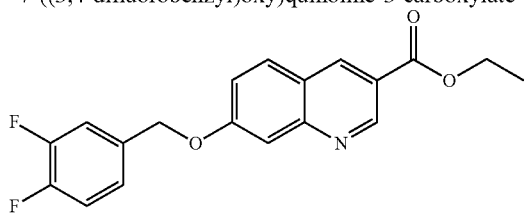

The title compound was prepared in a manner analogous to Example 1, substituting 3,4-difluorobenzyl chloride for 4-chlorobenzyl chloride. ¹H NMR (400 MHz, CDCl₃) δ 9.38 (d, J=2.3 Hz, 1H), 8.76 (d, J=2.0 Hz, 1H), 7.85 (d, J=9.0 Hz, 1H), 7.49 (d, J=2.7 Hz, 1H), 7.36-7.29 (m, 2H), 7.23-7.17 (m, 2H), 5.18 (s, 2H), 4.46 (q, J=7.0 Hz, 2H), 1.45 (t, J=7.0 Hz, 3H). [M+H]=344.3.

Example 15

Ethyl 7-((3,5-difluorobenzyl)oxy)quinoline-3-carboxylate

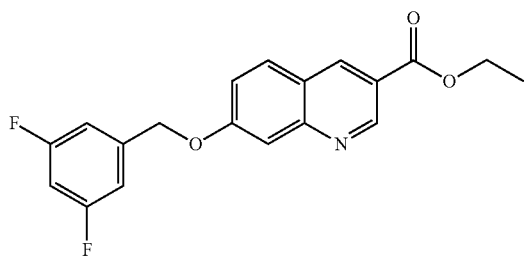 [SMILES: CCOC(=O)c1cnc2cc(OCc3cc(F)cc(F)c3)ccc2c1]

The title compound was prepared in a manner analogous to Example 1, substituting 3,5-difluorobenzyl chloride for 4-chlorobenzyl chloride. ¹H NMR (400 MHz, CDCl₃) δ 9.38 (d, J=2.0 Hz, 1H), 8.76 (d, J=2.0 Hz, 1H), 7.86 (d, J=9.0 Hz, 1H), 7.47 (d, J=2.3 Hz, 1H), 7.35 (dd, J=2.5, 8.8 Hz, 1H), 7.04-6.97 (m, 2H), 6.79 (tt, J=2.3, 8.8 Hz, 1H), 5.22 (s, 2H), 4.47 (q, J=7.0 Hz, 2H), 1.46 (t, J=7.0 Hz, 3H). [M+H]=344.3.

Example 16

Ethyl 7-((3,4,5-trifluorobenzyl)oxy)quinoline-3-carboxylate

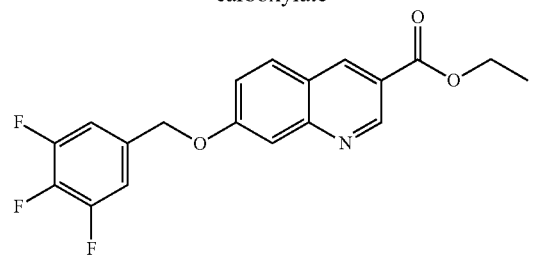

The title compound was prepared in a manner analogous to Example 1, substituting 3,4,5-trifluorobenzyl chloride for 4-chlorobenzyl chloride. ¹H NMR (400 MHz, CDCl₃) δ 9.37 (d, J=2.0 Hz, 1H), 8.75 (d, J=1.2 Hz, 1H), 7.84 (d, J=9.0 Hz, 1H), 7.44 (d, J=2.3 Hz, 1H), 7.31 (dd, J=2.3, 9.0 Hz, 1H), 7.11 (t, J=7.0 Hz, 2H), 5.15 (s, 2H), 4.45 (q, J=7.2 Hz, 2H), 1.47-1.39 (m, 3H). [M+H]=362.2.

Example 17

Ethyl 7-((3-chloro-4-fluorobenzyl)oxy)quinoline-3-carboxylate

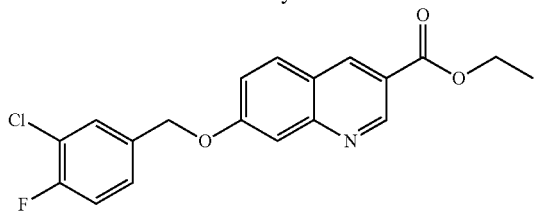

The title compound was prepared in a manner analogous to Example 1, substituting 3-chloro-4-fluorobenzyl bromide for 4-chlorobenzyl chloride. ¹H NMR (400 MHz, CDCl₃) δ 9.38 (d, J=2.0 Hz, 1H), 8.76 (d, J=2.3 Hz, 1H), 7.85 (d, J=9.0 Hz, 1H), 7.56 (dd, J=2.0, 7.0 Hz, 1H), 7.50 (d, J=2.3 Hz, 1H), 7.39-7.30 (m, 2H), 7.18 (t, J=8.6 Hz, 1H), 5.18 (s, 2H), 4.47 (q, J=7.0 Hz, 2H), 1.46 (t, J=7.2 Hz, 3H). [M+H]=360.2.

Example 18

Ethyl 7-((3-nitrobenzyl)oxy)quinoline-3-carboxylate

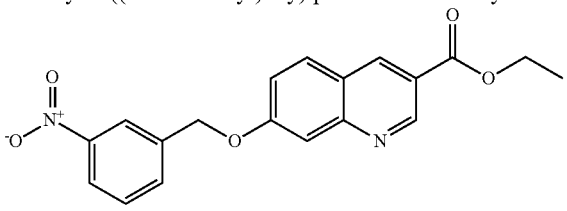

The title compound was prepared in a manner analogous to Example 1, substituting 3-nitrobenzyl chloride for 4-chlorobenzyl chloride. ¹H NMR (400 MHz, CDCl₃) δ 9.39 (d, J=2.0 Hz, 1H), 8.77 (d, J=2.0 Hz, 1H), 8.39 (s, 1H), 8.23 (dd, J=1.6, 8.2 Hz, 1H), 7.88 (d, J=9.0 Hz, 1H), 7.85-7.80 (m, 1H), 7.61 (t, J=8.0 Hz, 1H), 7.51 (d, J=2.3 Hz, 1H), 7.38 (dd, J=2.7, 9.0 Hz, 1H), 5.34 (s, 2H), 4.47 (q, J=7.2 Hz, 2H), 1.46 (t, J=7.0 Hz, 3H). [M+H]=353.3.

Example 19

Ethyl 7-((3-chloro-5-fluorobenzyl)oxy)quinoline-3-carboxylate

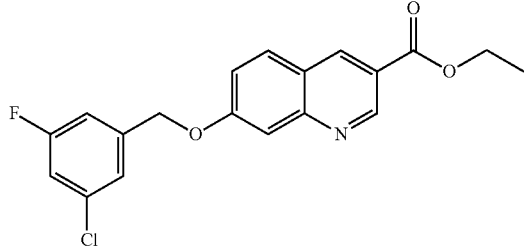

The title compound was prepared in a manner analogous to Example 1, substituting 5-chloro-3-fluorobenzyl chloride for 4-chlorobenzyl chloride. ¹H NMR (400 MHz, CDCl₃) δ 9.41-9.34 (m, 1H), 8.76 (d, J=2.0 Hz, 1H), 7.85 (d, J=9.0 Hz, 1H), 7.47 (d, J=2.3 Hz, 1H), 7.34 (dd, J=2.7, 9.0 Hz, 1H), 7.27 (s, 1H), 7.13-7.03 (m, 2H), 5.20 (s, 2H), 4.46 (q, J=7.0 Hz, 2H), 1.45 (t, J=7.2 Hz, 3H). [M+H]=360.2.

Example 20

Ethyl 7-((3-chlorobenzyl)oxy)-2-methylquinoline-3-carboxylate

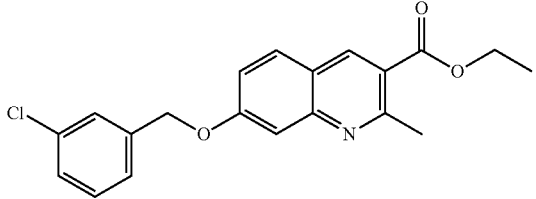 [SMILES: CCOC(=O)c1cc2ccc(OCc3cccc(Cl)c3)cc2nc1C]

Step A: 7-Hydroxy-2-methylquinoline-3-carboxylic acid. 7-Methoxy-2-methylquinoline-3-carboxylic acid (100 mg, 0.46 mmol) was suspended in HBr (aq.) (48%, 5 ml) and heated at 105° C. overnight. The reaction was cooled to ambient temperature. The precipitate was collected by filtration and dried under high vacuum to afford the title compound as a yellow solid (86 mg, 91%).

Step B: Ethyl 7-hydroxy-2-methylquinoline-3-carboxylate. 7-Hydroxy-2-methylquinoline-3-carboxylic acid (860 mg, 4.24 mmol) was dissolved in EtOH (29 mL) and H₂SO₄ (0.3 mL) was added. The reaction was heated at 75° C. for 23 h before being concentrated onto silica. Purification (FCC, SiO₂, 0-5%, MeOH/DCM) afforded the title compound as a yellow solid sulfate salt (1.128 g, 81%).

Step C: To a solution of ethyl 7-hydroxy-2-methylquinoline-3-carboxylate (100 mg, 0.43 mmol) in DMF (3.0 mL) was added Cs₂CO₃ (212 mg, 0.65 mmol) and 3-chlorobenzyl chloride (0.052 mL, 0.43 mmol). The reaction was stirred overnight at ambient temperature. The reaction mixture was loaded directly onto a column and purification (FCC, SiO₂, 0-40%, EtOAc/hexanes) afforded the title compound as a white solid (86 mg, 59%). ¹H NMR (400 MHz, CDCl₃) δ 8.68 (s, 1H), 7.77 (d, J=8.6 Hz, 1H), 7.48 (s, 1H), 7.40 (d, J=2.3 Hz, 1H), 7.37-7.30 (m, 3H), 7.29-7.26 (m, 1H), 5.19 (s, 2H), 4.42 (q, J=7.0 Hz, 2H), 2.97 (s, 3H), 1.44 (t, J=7.2 Hz, 3H). [M+H]=356.3.

Example 21

Ethyl 7-((3-fluorobenzyl)oxy)-2-methylquinoline-3-carboxylate

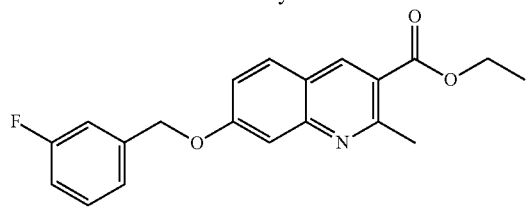

The title compound was prepared in a manner analogous to Example 20, substituting 3-fluorobenzyl chloride for 3-chlorobenzyl chloride in Step C. ¹H NMR (400 MHz, CDCl₃) δ 8.67 (s, 1H), 7.76 (d, J=9.0 Hz, 1H), 7.42-7.38 (m, 1H), 7.38-7.33 (m, 1H), 7.25-7.15 (m, 3H), 7.03 (dt, J=2.5, 8.5 Hz, 1H), 5.20 (s, 2H), 4.49-4.32 (m, 2H), 2.96 (s, 3H), 1.49-1.35 (m, 3H). [M+H]=340.2.

Example 22

Ethyl 7-((4-fluorobenzyl)oxy)-2-methylquinoline-3-carboxylate

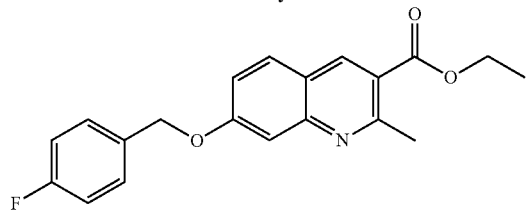

The title compound was prepared in a manner analogous to Example 20, substituting 4-fluorobenzyl chloride for 3-chlorobenzyl chloride in Step C. ¹H NMR (400 MHz, CDCl₃) δ 8.67 (s, 1H), 7.75 (d, J=9.0 Hz, 1H), 7.50-7.38 (m, 3H), 7.22 (d, J=2.7 Hz, 1H), 7.09 (t, J=8.8 Hz, 2H), 5.16 (s, 2H), 4.46-4.37 (m, 2H), 2.96 (s, 3H), 1.47-1.36 (m, 3H). [M+H]=340.3.

Example 23

Ethyl 7-((3-chloro-4-fluorobenzyl)oxy)-2-methylquinoline-3-carboxylate

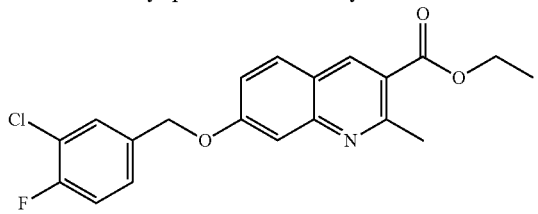

The title compound was prepared in a manner analogous to Example 20, substituting 3-chloro-4-fluorochlorobenzyl chloride for 3-chlorobenzyl chloride in Step C. ¹H NMR (400 MHz, CDCl₃) δ 8.67 (s, 1H), 7.79-7.74 (m, 1H), 7.53 (dd, J=2.0, 7.0 Hz, 1H), 7.39 (s, 1H), 7.33 (ddd, J=2.0, 4.2, 8.3 Hz, 1H), 7.24-7.21 (m, 1H), 7.19-7.13 (m, 1H), 5.14 (s, 2H), 4.48-4.37 (m, 2H), 2.99-2.92 (m, 3H), 1.48-1.42 (m, 3H). [M+H]=374.2.

Example 24

Ethyl 7-(3-fluorophenethoxy)quinoline-3-carboxylate

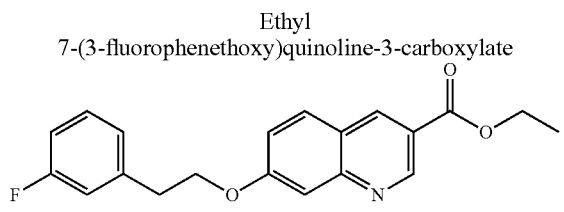

The title compound was prepared in a manner analogous to Example 1, substituting 2-(3-fluorophenyl)ethyl bromide for 4-chlorobenzyl chloride. $^1$H NMR (400 MHz, CDCl$_3$) δ 9.37 (d, J=2.0 Hz, 1H), 8.74 (d, J=2.0 Hz, 1H), 7.81 (d, J=9.0 Hz, 1H), 7.46 (d, J=2.3 Hz, 1H), 7.33-7.26 (m, 2H), 7.09 (d, J=7.4 Hz, 1H), 7.04 (td, J=2.0, 9.8 Hz, 1H), 6.95 (dt, J=2.2, 8.3 Hz, 1H), 4.46 (q, J=7.2 Hz, 2H), 4.37 (t, J=6.7 Hz, 2H), 3.18 (t, J=6.7 Hz, 2H), 1.45 (t, J=7.0 Hz, 3H). [M+H]=340.3.

Example 25

Ethyl 7-(3-chlorophenethoxy)quinoline-3-carboxylate

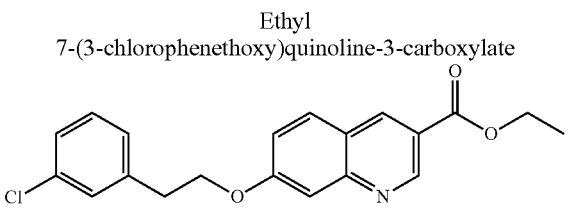

The title compound was prepared in a manner analogous to Example 1, substituting 3-chlorophenyl ethyl bromide for 4-chlorobenzyl chloride. $^1$H NMR (400 MHz, CDCl$_3$) δ 9.37 (d, J=2.0 Hz, 1H), 8.75 (d, J=2.0 Hz, 1H), 7.81 (d, J=9.0 Hz, 1H), 7.46 (d, J=2.3 Hz, 1H), 7.32 (s, 1H), 7.26-7.17 (m, 4H), 4.46 (q, J=7.2 Hz, 2H), 4.37 (t, J=6.7 Hz, 2H), 3.16 (t, J=6.7 Hz, 2H), 1.45 (t, J=7.0 Hz, 3H). [M+H]=356.30.

Example 26

Methyl 7-((3-chlorobenzyl)oxy)quinoline-3-carboxylate

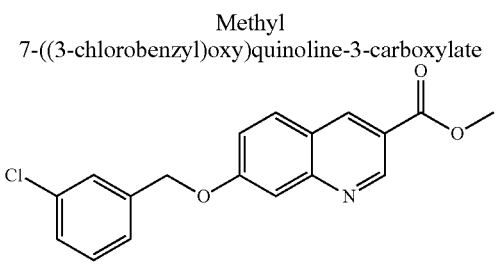

To a solution of ethyl 7-[(3-chlorophenyl)methoxy]quinoline-3-carboxylate (Example 3, 20 mg, 0.06 mmol) in MeOH (1 mL) and THF (1 mL) was added K$_2$CO$_3$. The reaction was stirred overnight at ambient temperature. The crude reaction mixture was concentrated onto silica and purification (FCC, SiO$_2$, 0-40%, EtOAc/hexanes) afforded the title compound as a white solid (12 mg, 63%). $^1$H NMR (400 MHz, CDCl$_3$) δ 9.37 (d, J=2.0 Hz, 1H), 8.76 (d, J=2.3 Hz, 1H), 7.84 (d, J=9.0 Hz, 1H), 7.50 (d, J=2.3 Hz, 2H), 7.38-7.30 (m, 4H), 5.21 (s, 2H), 4.00 (s, 3H). [M+H]=328.2.

Example 27

2-(7-((4-Fluorobenzyl)oxy)quinolin-3-yl)propan-2-ol

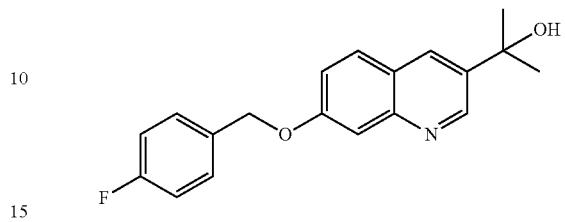

To a cooled solution, 0° C., of ethyl 7-[(4-fluorophenyl)methoxy]quinoline-3-carboxylate (Example 2, 140 mg, 0.43 mmol) in THF (10.0 mL) was added methyl magnesium bromide (3.0 M, 2.5 mL, 7.53 mmol). The reaction was stirred for 15 minutes at 0° C. before being quenched with a sat. NH$_4$Cl (aq.) solution. The aqueous layer was extracted with EtOAc. The organic layers were combined and concentrated onto silica. Purification (FCC, SiO$_2$, 0-5%, MeOH/DCM) afforded the title compound as a yellow solid (84 mg, 63%). $^1$H NMR (400 MHz, CDCl$_3$) δ 8.98 (d, J=2.3 Hz, 1H), 8.17 (d, J=2.3 Hz, 1H), 7.72 (d, J=9.0 Hz, 1H), 7.52-7.44 (m, 3H), 7.29-7.26 (m, 1H), 7.09 (t, J=8.8 Hz, 2H), 5.17 (s, 2H), 1.70 (s, 6H). [M+H]=312.3.

Example 28

2-(7-((3-Chlorobenzyl)oxy)quinolin-3-yl)propan-2-ol

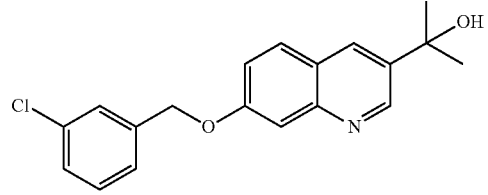 [SMILES: CC(C)(O)c1cnc2cc(OCc3cccc(Cl)c3)ccc2c1]

The title compound was prepared in a manner analogous to Example 27, substituting ethyl 7-[(3-chlorophenyl)methoxy]quinoline-3-carboxylate (Example 3) for ethyl 7-[(4-fluorophenyl)methoxy]quinoline-3-carboxylate (Example 2). $^1$H NMR (400 MHz, CDCl$_3$) δ 8.98 (d, J=2.3 Hz, 1H), 8.17 (d, J=2.3 Hz, 1H), 7.73 (d, J=9.0 Hz, 1H), 7.49 (s, 1H), 7.44 (d, J=2.3 Hz, 1H), 7.33 (s, 4H), 5.18 (s, 2H). [M+H]=328.2.

Example 29

2-(7-((3,5-Difluorobenzyl)oxy)quinolin-3-yl)propan-2-ol

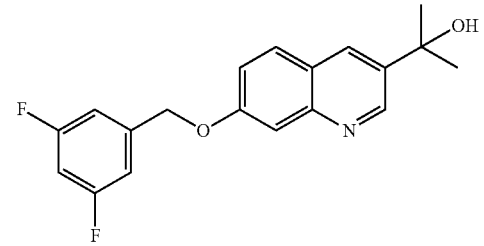 [SMILES: CC(C)(O)c1cnc2cc(OCc3cc(F)cc(F)c3)ccc2c1]

The title compound was prepared in a manner analogous to Example 27, substituting ethyl 7-((3,5-difluorobenzyl)oxy)

quinoline-3-carboxylate (Example 15) for ethyl 7-[(4-fluorophenyl)methoxy]quinoline-3-carboxylate (Example 2). $^1$H NMR (400 MHz, DMSO-d$_6$) δ 9.00 (d, J=2.3 Hz, 1H), 8.29 (d, J=2.3 Hz, 1H), 7.94 (d, J=9.0 Hz, 1H), 7.47 (d, J=2.7 Hz, 1H), 7.37 (dd, J=2.7, 9.0 Hz, 1H), 7.33-7.22 (m, 3H), 5.34 (d, J=3.5 Hz, 3H), 1.57 (s, 6H). [M+H]=330.3.

Example 30

2-(7-((3,4,5-Trifluorobenzyl)oxy)quinolin-3-yl)propan-2-ol

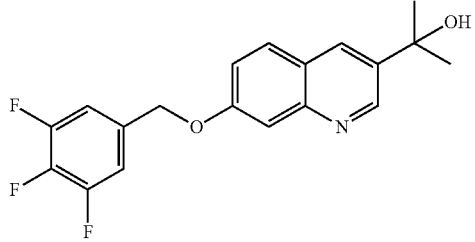 [SMILES: CC(C)(O)c1cnc2cc(OCc3cc(F)c(F)c(F)c3)ccc2c1]

The title compound was prepared in a manner analogous to Example 27, substituting ethyl 7-((3,4,5-trifluorobenzyl)oxy)quinoline-3-carboxylate (Example 16) for ethyl 7-[(4-fluorophenyl)methoxy]quinoline-3-carboxylate (Example 2). $^1$H NMR (400 MHz, DMSO-d$_6$) δ 8.95 (d, J=2.3 Hz, 1H), 8.24 (d, J=2.3 Hz, 1H), 7.89 (d, J=9.0 Hz, 1H), 7.49 (dd, J=8.6, 7.0 Hz, 2H), 7.43 (d, J=2.7 Hz, 1H), 7.31 (dd, J=9.0, 2.3 Hz, 1H), 5.25 (s, 2H), 1.52 (s, 6H). [M+H]=348.3.

Example 31

2-(7-((4-Fluorobenzyl)oxy)-2-methylquinolin-3-yl)propan-2-ol

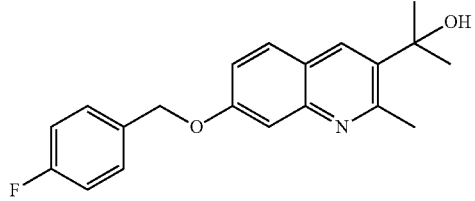 [SMILES: Cc1nc2cc(OCc3ccc(F)cc3)ccc2cc1C(C)(C)O]

To a solution of ethyl 7-((4-fluorobenzyl)oxy)-2-methylquinoline-3-carboxylate (Example 22, 65 mg, 0.19 mmol) in THF was added methyl magnesium bromide (3 M in Et$_2$O, 0.5 mL, 1.5 mmol). The reaction was stirred for 30 minutes before being quenched with a sat. NH$_4$Cl (aq.) solution. The aqueous layer was extracted with EtOAc. The organic layers were combined and concentrated onto silica. Purification (FCC, SiO$_2$, 0-5%, MeOH/DCM) afforded the title compound as a yellow solid (28 mg, 45%). $^1$H NMR (400 MHz, CDCl$_3$) δ 8.10 (s, 1H), 7.65 (d, J=8.6 Hz, 1H), 7.44 (dd, J=5.5, 8.2 Hz, 2H), 7.37 (d, J=2.0 Hz, 1H), 7.18 (dd, J=2.3, 9.0 Hz, 1H), 7.07 (t, J=8.6 Hz, 2H), 5.13 (s, 2H), 2.95 (s, 3H), 1.75 (s, 6H). [M+H]=326.3.

Example 32

2-(7-((3-Chlorobenzyl)oxy)-2-methylquinolin-3-yl)propan-2-ol

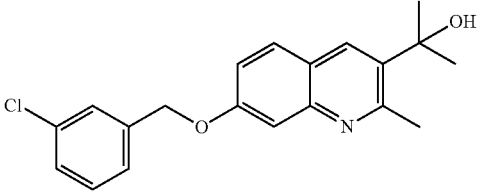 [SMILES: Cc1nc2cc(OCc3cccc(Cl)c3)ccc2cc1C(C)(C)O]

The title compound was prepared in a manner analogous to Example 31, substituting ethyl 7-((3-chlorobenzyl)oxy)-2-methylquinoline-3-carboxylate (Example 20) for ethyl 7-((4-fluorobenzyl)oxy)-2-methylquinoline-3-carboxylate (Example 22). $^1$H NMR (400 MHz, CDCl$_3$) δ 8.10 (s, 1H), 7.65 (d, J=8.6 Hz, 1H), 7.46 (s, 1H), 7.37-7.26 (m, 4H), 7.21-7.16 (m, 1H), 5.14 (s, 2H), 2.94 (s, 3H), 1.74 (s, 6H). [M+H]=342.2.

Example 33

2-(7-((3-Chloro-4-fluorobenzyl)oxy)-2-methylquinolin-3-yl)propan-2-ol

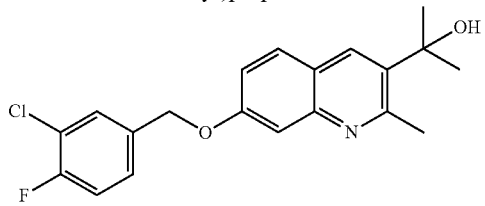

The title compound was prepared in a manner analogous to Example 31, substituting ethyl 7-((3-chloro-4-fluorobenzyl)oxy)-2-methylquinoline-3-carboxylate (Example 23) for ethyl 7-((4-fluorobenzyl)oxy)-2-methylquinoline-3-carboxylate (Example 22). $^1$H NMR (400 MHz, CDCl$_3$) δ 8.11 (s, 1H), 7.69-7.63 (m, 1H), 7.55-7.48 (m, 1H), 7.38-7.29 (m, 2H), 7.21-7.08 (m, 2H), 5.11 (s, 2H), 2.97-2.93 (m, 3H), 1.76-1.73 (m, 6H). [M+H]=360.2.

Example 34

2-(7-((3-Fluorobenzyl)oxy)-2-methylquinolin-3-yl)propan-2-ol

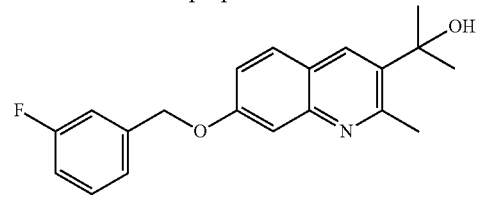

The title compound was prepared in a manner analogous to Example 31, substituting ethyl 7-((3-fluorobenzyl)oxy)-2-methylquinoline-3-carboxylate (Example 21) for ethyl 7-((4-fluorobenzyl)oxy)-2-methylquinoline-3-carboxylate (Example 22). $^1$H NMR (400 MHz, CDCl$_3$) δ 8.12 (s, 1H), 7.68 (d, J=9.0 Hz, 1H), 7.40-7.31 (m, 2H), 7.25-7.18 (m, 3H), 7.05-6.97 (m, 1H), 5.19 (s, 2H), 2.96 (s, 3H), 1.76 (s, 6H). [M+H]=326.2.

Example 35

(7-((3-Chlorobenzyl)oxy)quinolin-3-yl)methanol

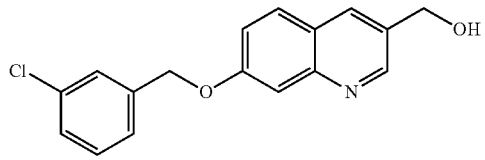 [SMILES: OCc1cnc2cc(OCc3cccc(Cl)c3)ccc2c1]

To a cooled solution, −78° C., under nitrogen, of ethyl 7-[(3-chlorophenyl)methoxy]quinoline-3-carboxylate (Example 3, 172 mg, 0.50 mmol) in THF (8.0 mL) was added LiAlH$_4$ (2.4 M in THF, 2.0 mL, 4.8 mmol). The reaction mixture was stirred for 7 h before being quenched with a 1 N NaOH (aq.) solution. The crude reaction mixture was filtered through CELITE® and the aqueous layer was extracted with EtOAc. The organic layers were combined and concentrated onto silica. Purification (FCC, SiO$_2$, 0-5%, MeOH/DCM) afforded the title compound as a yellow solid (115 mg, 76%). $^1$H NMR (400 MHz, DMSO-d$_6$) δ 8.81 (d, J=2.3 Hz, 1H), 8.20 (d, J=1.2 Hz, 1H), 7.94 (d, J=9.0 Hz, 1H), 7.64 (s, 1H), 7.57-7.43 (m, 4H), 7.37 (dd, J=2.7, 9.0 Hz, 1H), 5.43 (t, J=5.7 Hz, 1H), 5.34 (s, 2H), 4.71 (d, J=5.5 Hz, 2H). [M+H]=300.2.

Example 36

(7-((3,5-Difluorobenzyl)oxy)quinolin-3-yl)methanol

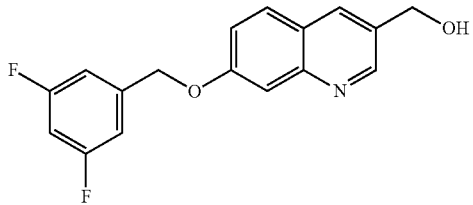 [SMILES: OCc1cnc2cc(OCc3cc(F)cc(F)c3)ccc2c1]

The title compound was prepared in a manner analogous to Example 35, substituting ethyl 7-((3,4,5-trifluorobenzyl)oxy)quinoline-3-carboxylate (Example 15) for ethyl 7-[(3-chlorophenyl)methoxy]quinoline-3-carboxylate (Example 3). $^1$H NMR (400 MHz, DMSO-d$_6$) δ 8.81 (d, J=2.3 Hz, 1H), 8.20 (s, 1H), 7.95 (d, J=9.0 Hz, 1H), 7.49 (d, J=2.7 Hz, 1H), 7.38 (dd, J=2.5, 8.8 Hz, 1H), 7.33-7.23 (m, 3H), 5.43 (t, J=5.5 Hz, 1H), 5.35 (s, 2H), 4.70 (d, J=5.5 Hz, 2H). [M+H]=302.3.

Example 37

(7-((3,4,5-Trifluorobenzyl)oxy)quinolin-3-yl)methanol

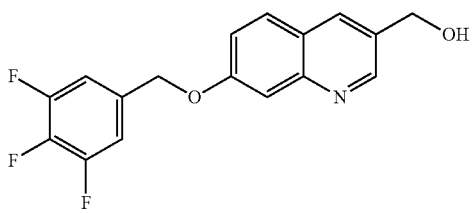 [SMILES: OCc1cnc2cc(OCc3cc(F)c(F)c(F)c3)ccc2c1]

The title compound was prepared in a manner analogous to Example 35, substituting ethyl 7-[(3,4,5-trifluorophenyl)methoxy]quinoline-3-carboxylate (Example 16) for ethyl 7-[(3-chlorophenyl)methoxy]quinoline-3-carboxylate (Example 3). $^1$H NMR (400 MHz, DMSO-d$_6$) δ 8.82 (d, J=2.3 Hz, 1H), 8.20 (s, 1H), 7.94 (d, J=9.0 Hz, 1H), 7.58-7.53 (m, 2H), 7.50 (d, J=2.3 Hz, 1H), 7.37 (dd, J=2.5, 8.8 Hz, 1H), 5.45-5.41 (m, 1H), 5.30 (s, 2H), 4.70 (d, J=5.9 Hz, 2H). [M+H]=320.3.

Example 38

2-(7-(3-Fluorophenethoxy)quinolin-3-yl)propan-2-ol

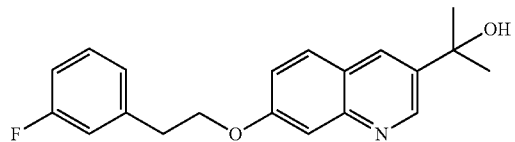 [SMILES: CC(C)(O)c1cnc2cc(OCCc3cccc(F)c3)ccc2c1]

The title compound was prepared in a manner analogous to Example 27, substituting ethyl 7-(3-fluorophenethoxy)quinoline-3-carboxylate (Example 24), for ethyl 7-[(4-fluorophenyl)methoxy]quinoline-3-carboxylate (Example 2). $^1$H NMR (400 MHz, CDCl$_3$) δ 8.98 (d, J=2.3 Hz, 1H), 8.25 (s, 1H), 7.73 (d, J=9.0 Hz, 1H), 7.51 (br. s., 1H), 7.32-7.26 (m, 1H), 7.25-7.20 (m, 1H), 7.09 (d, J=7.4 Hz, 1H), 7.04 (d, J=9.8 Hz, 1H), 6.98-6.91 (m, 1H), 4.36 (t, J=6.7 Hz, 2H), 3.17 (t, J=6.7 Hz, 2H), 1.70 (s, 6H). [M+H]=326.1.

Example 39

2-(7-(3-Chlorophenethoxy)quinolin-3-yl)propan-2-ol

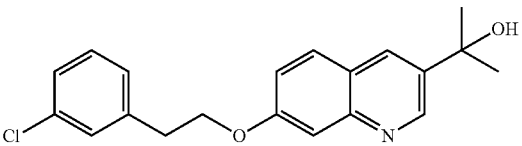 [SMILES: CC(C)(O)c1cnc2cc(OCCc3cccc(Cl)c3)ccc2c1]

The title compound was prepared in a manner analogous to Example 27, substituting ethyl 7-(3-chlorophenethoxy)quinoline-3-carboxylate (Example 25) for ethyl 7-[(4-fluorophenyl)methoxy]quinoline-3-carboxylate (Example 2). $^1$H NMR (400 MHz, CDCl$_3$) δ 8.96 (d, J=2.3 Hz, 1H), 8.16 (d, J=1.6 Hz, 1H), 7.68 (d, J=9.0 Hz, 1H), 7.40 (d, J=2.3 Hz, 1H), 7.33-7.30 (m, 1H), 7.25-7.15 (m, 4H), 4.31 (t, J=6.7 Hz, 2H), 3.14 (t, J=6.7 Hz, 2H), 1.70-1.67 (m, 6H). [M+H]=342.1.

Example 40

7-((3-Chlorobenzyl)oxy)-3-(methoxymethyl)quinoline

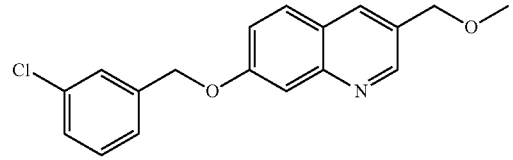 [SMILES: COCc1cnc2cc(OCc3cccc(Cl)c3)ccc2c1]

To a cooled solution of NaH (60% in mineral oil, 12 mg, 0.3 mmol) in DMF (0.5 mL) under an atmosphere of nitrogen, was added a solution of (7-((3-chlorobenzyl)oxy)quinolin-3-yl)methanol (Example 35, 30 mg, 0.10 mmol) in DMF (0.5 mL). The reaction was stirred for 10 minutes. Methyl iodide (0.019 mL, 0.3 mmol) was added and the reaction was stirred for an additional 25 minutes at 0° C. before being quenched with a sat. NH$_4$Cl (aq.) solution. The aqueous layer was extracted with EtOAc. The organic layers were combined and concentrated onto silica. Purification (FCC, SiO$_2$, 0-60%, EtOAc/hexanes) afforded the title compound as a white solid (19 mg, 61%). $^1$H NMR (400 MHz, CDCl$_3$) δ 8.81 (d, J=2.0 Hz, 1H), 8.05 (d, J=1.6 Hz, 1H), 7.73 (d, J=8.6 Hz, 1H), 7.50

(s, 1H), 7.46 (d, J=2.7 Hz, 1H), 7.39-7.27 (m, 4H), 5.19 (s, 2H), 4.62 (s, 2H), 3.45 (s, 3H). [M+H]=314.2.

Example 41

7-((4-Fluorobenzyl)oxy)-3-(2-fluoropropan-2-yl)quinoline

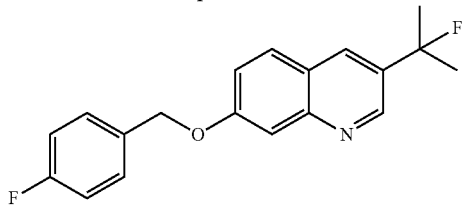

XtalFluor® (66.19 mg, 0.29 mmol) was transferred to a flask and put under nitrogen, then DCM (2 mL) was added via syringe. The reaction was cooled to 0° C. in an ice bath then triethylamine trihydrofluoride (62.76 μl, 0.39 mmol) and triethylamine (26.7 μL, 0.19 mmol) were added via syringe. The reaction was stirred until all solids dissolved completely then was cooled to −78° C. in a dry ice/acetone bath. A solution of 2-(7-((4-fluorobenzyl)oxy)quinolin-3-yl)propan-2-ol (Example 27, 60 mg, 0.19 mmol) in DCM (1 mL) was added via syringe then the reaction was warmed to 0° C. and allowed to stir for 1 hour. Upon completion, a solution of NaHCO$_3$ (sat aq.) and EtOAc was added. The combined organics were separated and washed with a 50% aq. bleach solution. The combined organics were dried over Na$_2$SO$_4$, filtered, and concentrated under reduced pressure. Purification (FCC, SiO$_2$, 0-25%, EtOAc/Hexanes,), and a second purification with preparative HPLC (Shimadzu SCL-10 VP, ACN/H$_2$O, 25-90% (0.1% TFA)) afforded the title compound as a pure solid (18.2 mg, 22%). $^1$H NMR (400 MHz, CDCl$_3$) δ 9.08 (d, J=1.8 Hz, 1H), 8.19 (d, J=2.0 Hz, 1H), 7.77 (d, J=9.0 Hz, 1H), 7.53 (dd, J=5.4, 8.4 Hz, 2H), 7.43 (d, J=9.0 Hz, 1H), 7.29 (s, 1H), 7.12 (t, J=8.7 Hz, 2H), 5.35 (s, 2H), 1.99-1.63 (m, 6H). [M+H]=314.1.

Example 42

1-(7-((4-Fluorobenzyl)oxy)quinolin-3-yl)ethanone

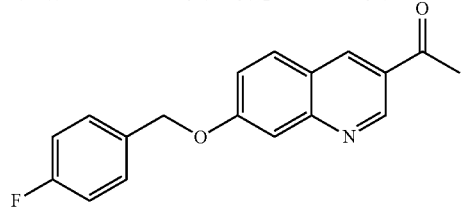 [SMILES: CC(=O)c1cnc2cc(OCc3ccc(F)cc3)ccc2c1]

Step A. Sodium 7-((4-fluorobenzyl)oxy)quinoline-3-carboxylate. To a solution of ethyl 7-[(4-fluorophenyl)methoxy]quinoline-3-carboxylate (Example 2, 430 mg, 1.32 mmol) in MeOH (2 mL) and THF (2 mL) was added NaOH (95 mg, 2.38 mmol) in H$_2$O (2.0 mL). The reaction was stirred for 15 minutes at ambient temperature. The crude reaction mixture was concentrated under reduced pressure to afford the title compound as a white solid. $^1$H NMR (400 MHz, DMSO-d$_6$) δ 9.29 (d, J=2.0 Hz, 1H), 8.60 (d, J=2.0 Hz, 1H), 7.96 (d, J=9.0 Hz, 1H), 7.63 (dd, J=5.5, 8.6 Hz, 2H), 7.50 (d, J=2.7 Hz, 1H), 7.35-7.25 (m, 3H), 5.31 (s, 2H). [M+H]=298.2
Step B. 7-((4-fluorobenzyl)oxy)quinoline-3-carbonyl chloride. To a solution of sodium 7-((4-fluorobenzyl)oxy)quinoline-3-carboxylate (452 mg, 1.41 mmol) in DCM (14 mL) was added oxalyl chloride (0.378 mL, 4.23 mmol), followed by 1 drop of DMF. The reaction was stirred for 30 minutes at ambient temperature. The crude mixture was concentrated to afford a crude solid and dried under high vacuum for 30 minutes and used without further purification in the next step.
Step C. 7-((4-Fluorobenzyl)oxy)-N-methoxy-N-methylquinoline-3-carboxamide. To a solution of 7-((4-fluorobenzyl)oxy)quinoline-3-carbonyl chloride in DCM (14 mL) was added N,O-dimethylhydroxylamine hydrochloride (207 mg, 2.12 mmol) and DIPEA (0.739 mL, 4.23 mmol). The reaction was stirred for 15 minutes at ambient temperature before being concentrated onto silica. Purification (FCC, SiO$_2$, 0-80%, EtOAc/hexanes) afforded the title compound as a white solid (324 mg, 67%). $^1$H NMR (400 MHz, CDCl$_3$) δ 9.18 (d, J=2.0 Hz, 1H), 8.54 (d, J=1.6 Hz, 1H), 7.81 (d, J=9.0 Hz, 1H), 7.52 (d, J=2.0 Hz, 1H), 7.51-7.44 (m, 2H), 7.32 (dd, J=2.3, 9.0 Hz, 1H), 7.11 (t, J=8.8 Hz, 2H), 5.21 (s, 2H), 3.59 (s, 3H), 3.45 (d, J=0.8 Hz, 3H). [M+H]=341.3.
Step D. 1-(7-((4-fluorobenzyl)oxy)quinolin-3-yl)ethanone. To a cooled solution, 0° C., under an atmosphere of nitrogen, of 7-((4-Fluorobenzyl)oxy)-N-methoxy-N-methylquinoline-3-carboxamide (224 mg, 0.667 mmol) in THF was added methyl magnesium bromide (3.0 M in Et$_2$O, 0.466 mL, 1.40 mmol). The reaction was stirred for 1 hour at 0° C. before being quenched with a sat. NH$_4$Cl (aq.) solution. The aqueous layer was extracted with EtOAc. The organic layers were combined, washed with brine and concentrated under reduced pressure onto silica. Purification (FCC, SiO$_2$, 0-50%, EtOAc/hexanes) afforded the title compound as a white solid (145 mg, 75%). $^1$H NMR (400 MHz, CDCl$_3$) δ 9.36 (d, J=2.0 Hz, 1H), 8.64 (s, 1H), 7.85 (d, J=9.0 Hz, 1H), 7.54 (s, 1H), 7.46 (dd, J=5.7, 8.4 Hz, 2H), 7.33 (dd, J=2.3, 9.0 Hz, 1H), 7.10 (t, J=8.6 Hz, 2H), 5.20 (s, 2H), 2.72 (s, 3H). [M+H]=296.3.

Example 43

1-(7-((4-Fluorobenzyl)oxy)quinolin-3-yl)ethanol

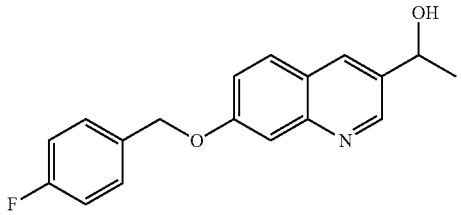 [SMILES: CC(O)c1cnc2cc(OCc3ccc(F)cc3)ccc2c1]

To a cooled solution, 0° C., of 1-(7-((4-fluorobenzyl)oxy)quinolin-3-yl)ethanone (Example 42, 53 mg, 0.18 mmol) in THF was added NaBH$_4$ (8 mg, 0.24 mmol). The reaction mixture was stirred for 1 hour. A further portion of NaBH$_4$ (20 mg, 0.59 mmol) was added and stirred for 30 minutes at 0° C. LiBH$_4$ (50 mg, 2.30 mmol) was added and the reaction was stirred for 15 minutes before being quenched with sat. NH$_4$Cl (aq.) solution. The aqueous layer was extracted with EtOAc. The combined organic layers were washed with brine and concentrated under reduced pressure onto silica. Purification (FCC, SiO$_2$, 0-5%, MeOH/DCM) afforded the title compound as a white solid (20 mg, 38%). $^1$H NMR (400 MHz, CDCl$_3$) δ 8.85 (d, J=1.6 Hz, 1H), 8.10 (s, 1H), 7.73 (d, J=9.0

Hz, 1H), 7.53-7.43 (m, 3H), 7.31-7.26 (m, 1H), 7.09 (t, J=8.6 Hz, 2H), 5.17 (s, 2H), 5.12 (q, J=6.5 Hz, 1H), 1.62 (d, J=6.7 Hz, 3H). [M+H]=298.3.

Example 44

(R)-1-(7-((4-Fluorobenzyl)oxy)quinolin-3-yl)ethanol

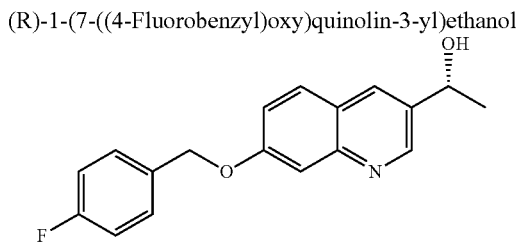

To a cooled solution, −78° C., of 1-(7-((4-fluorobenzyl)oxy)quinolin-3-yl)ethanone (Example 42, 52 mg, 0.176 mmol) in toluene was added (R)-(+)-2-methyl-CBS-oxazaborolidine (97 mg, 0.352 mmol) followed by BH$_3$.DMS (2 M in THF, 0.176 mL, 0.352 mmol). The reaction was warmed to −20° C. and stirred for 3 h followed by treatment with MeOH. The resulting mixture was warmed to ambient temperature and sat. NaHCO$_3$ (aq.) solution was added. The aqueous layer was extracted with EtOAc and the combined organic fractions were washed with brine and concentrated under reduced pressure onto silica. Purification (FCC, SiO$_2$, 0–5%, MeOH/DCM) afforded the title compound as a white solid (29 mg, 56%). $^1$H NMR (400 MHz, DMSO-d$_6$) δ 8.85 (d, J=2.3 Hz, 1H), 8.20 (d, J=2.0 Hz, 1H), 7.93 (d, J=9.0 Hz, 1H), 7.61 (dd, J=5.5, 8.6 Hz, 2H), 7.51 (d, J=2.3 Hz, 1H), 7.33 (dd, J=2.5, 8.8 Hz, 1H), 7.28 (t, J=9.0 Hz, 2H), 5.44 (d, J=4.3 Hz, 1H), 5.29 (s, 2H), 5.01-4.91 (m, 1H), 1.47 (d, J=6.7 Hz, 3H). [M+H]=298.2.

Example 45

(S)-1-(7-((4-Fluorobenzyl)oxy)quinolin-3-yl)ethanol

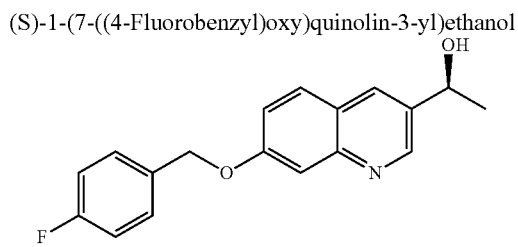

To a cooled solution, −78° C., of 1-(7-((4-fluorobenzyl)oxy)quinolin-3-yl)ethanone (Example 42, 52 mg, 0.176 mmol) in toluene was added (S)-(−)-2-methyl-CBS-oxazaborolidine (97 mg, 0.352 mmol) followed by BH$_3$.DMS (2 M in THF, 0.176 mL, 0.352 mmol). The reaction was warmed to −20° C. and stirred for 3 h before being quenched with MeOH. The reaction was warmed to ambient temperature and sat. NaHCO$_3$ (aq.) solution was added. The aqueous layer was extracted with EtOAc and the combined organic fractions were washed with brine and concentrated under reduced pressure onto silica. Purification (FCC, SiO$_2$, 0-5%, MeOH/DCM) afforded the title compound as a white solid (9 mg, 17%). $^1$H NMR (400 MHz, DMSO-d$_6$) δ 8.85 (d, J=2.3 Hz, 1H), 8.20 (d, J=2.0 Hz, 1H), 7.93 (d, J=9.0 Hz, 1H), 7.61 (dd, J=5.5, 8.6 Hz, 2H), 7.51 (d, J=2.3 Hz, 1H), 7.33 (dd, J=2.5, 8.8 Hz, 1H), 7.28 (t, J=9.0 Hz, 2H), 5.44 (d, J=4.3 Hz, 1H), 5.29 (s, 2H), 5.01-4.91 (m, 1H), 1.47 (d, J=6.7 Hz, 3H). [M+H]=298.2.

Example 46

7-((3-Chlorobenzyl)oxy)-N-methylquinoline-3-carboxamide

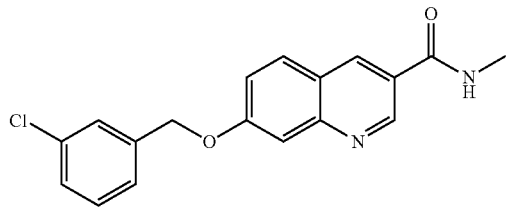 [SMILES: CNC(=O)c1cnc2cc(OCc3cccc(Cl)c3)ccc2c1]

Step A: 7-((3-Chlorobenzyl)oxy)quinoline-3-carboxylic acid. To a solution of ethyl 7-[(3-chlorophenyl)methoxy]quinoline-3-carboxylate (Example 3, 150 mg, 0.44 mmol) in MeOH (0.7 mL) and THF (1.7 mL) was added LiOH (13 mg, 0.54 mmol) in H$_2$O (1.7 mL). The reaction was stirred for 14 h at ambient temperature. The crude reaction mixture was concentrated to dryness under reduced pressure. 10% HCl (aq.) (6.0 mL) was added, and the precipitate was collected and dried under high pressure to afford the title compound as a white solid (106 mg, 77%). $^1$H NMR (400 MHz, DMSO-d$_6$) δ 9.25 (d, J=2.3 Hz, 1H), 8.79 (d, J=2.3 Hz, 1H), 8.25 (s, 1H), 8.03 (d, J=9.4 Hz, 1H), 7.63 (s, 1H), 7.58-7.41 (m, 4H), 5.37 (s, 2H). [M+H]=314.2.

Step B: 7-((3-Chlorobenzyl)oxy)-N-methylquinoline-3-carboxamide. To a solution of 7-((3-chlorobenzyl)oxy)quinoline-3-carboxylic acid (50 mg, 0.16 mmol) in DCM (1.5 mL) was added oxalyl chloride (0.042 mL, 0.48 mmol) followed by 1 drop of DMF. After 30 minutes, methylamine (2M in THF, 1 mL, 2 mmol) was added to the reaction. The reaction was stirred for 14 h. The crude reaction was loaded directly onto a column and purification (FCC, SiO$_2$, 0-10%, MeOH/DCM) afforded the title compound as a white solid (19 mg, 37%). $^1$H NMR (400 MHz, CDCl$_3$) δ 9.17 (d, J=2.3 Hz, 1H), 8.53 (d, J=2.0 Hz, 1H), 7.82 (d, J=9.0 Hz, 1H), 7.49 (d, J=2.7 Hz, 2H), 7.38-7.31 (m, 4H), 6.28-6.22 (m, 1H), 5.21 (s, 2H), 3.10 (d, J=4.7 Hz, 3H). [M+H]=327.2.

Example 47

N-(2-Aminoethyl)-7-((3-chlorobenzyl)oxy)quinoline-3-carboxamide

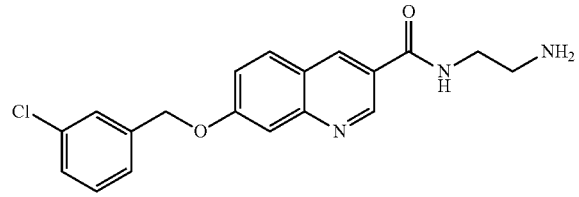 [SMILES: NCCNC(=O)c1cnc2cc(OCc3cccc(Cl)c3)ccc2c1]

Step A: 7-((3-chlorobenzyl)oxy)quinoline-3-carbonyl chloride. To a solution of 7-((3-chlorobenzyl)oxy)quinoline-3-carboxylic acid (Example 46, product from Step A, 50 mg, 0.16 mmol) in DCM (1.5 mL) was added oxalyl chloride (0.1 mL, 1.13 mmol), followed by 1 drop of DMF. After 30 minutes the reaction was concentrated under reduced pressure to afford a yellow foam, and further dried under high vacuum for 15 minutes to afford the title compound, which was used without further purification in the next step.

Step B: tert-Butyl (2-(7-((3-chlorobenzyl)oxy)quinoline-3-carboxamido)ethyl)carbamate. To a solution of 7-((3-chlorobenzyl)oxy)quinoline-3-carbonyl chloride in THF (1.5 mL) was added tert-butyl (2-aminoethyl)carbamate (38 mg, 0.23 mmol) and triethylamine (0.044 mL, 0.32 mmol). The reaction was stirred for 14 h. The crude reaction was loaded directly onto a column and purification (FCC, SiO$_2$, 0-5%, MeOH/DCM) afforded the title compound as a white solid (44 mg, 60%). $^1$H NMR (400 MHz, CDCl$_3$) δ 9.31-9.20 (m, 1H), 8.61-8.51 (m, 1H), 7.80 (d, J=9.0 Hz, 1H), 7.68-7.60 (m, 1H), 7.49 (s, 2H), 7.40-7.29 (m, 4H), 5.20 (s, 2H), 5.09-4.92 (m, 1H), 3.68-3.59 (m, 2H), 3.50-3.43 (m, 2H), 1.44 (s, 9H). [M+H]=456.3

Step C: N-(2-Aminoethyl)-7-((3-chlorobenzyl)oxy)quinoline-3-carboxamide. To a cooled solution, 0° C., of tert-Butyl (2-(7-((3-chlorobenzyl)oxy)quinoline-3-carboxamido)ethyl)carbamate in DCM (1 mL) was added TFA (1 mL). The reaction was stirred for 1 hour, and concentrated under reduced pressure. The reaction mixture was taken up in MeOH and concentrated under reduced pressure to afford the title compound as a white solid, TFA salt (57 mg, 100%) $^1$H NMR (400 MHz, DMSO-d$_6$) δ 9.22 (d, J=2.0 Hz, 1H), 8.88 (t, J=5.5 Hz, 1H), 8.76 (s, 1H), 8.03 (d, J=9.0 Hz, 1H), 7.60 (s, 1H), 7.54 (d, J=2.3 Hz, 1H), 7.51-7.39 (m, 4H), 5.34 (s, 2H), 3.55 (q, J=6.3 Hz, 2H), 3.10-2.95 (m, 2H). [M+H]=356.3

Example 48

7-((3-Chlorobenzyl)oxy)-N-(2-(methylamino)ethyl)quinoline-3-carboxamide

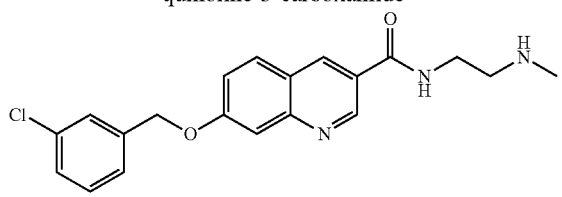

The title compound was prepared in a manner analogous to Example 47, substituting tert-butyl (2-aminoethyl)(methyl)carbamate for tert-butyl (2-aminoethyl)carbamate in Step B. $^1$H NMR (400 MHz, DMSO-d$_6$) δ 9.23 (d, J=2.3 Hz, 1H), 8.96 (t, J=5.7 Hz, 1H), 8.78 (d, J=2.0 Hz, 1H), 8.04 (d, J=9.0 Hz, 1H), 7.60 (s, 1H), 7.55 (d, J=2.3 Hz, 1H), 7.51-7.38 (m, 4H), 5.34 (s, 2H), 3.60 (q, J=5.7 Hz, 2H), 3.21-3.04 (m, 2H), 2.61 (t, J=5.3 Hz, 3H). [M+H]=370.3.

Example 49

7-((3-Chlorobenzyl)oxy)-N-(2-(dimethylamino)ethyl)quinoline-3-carboxamide

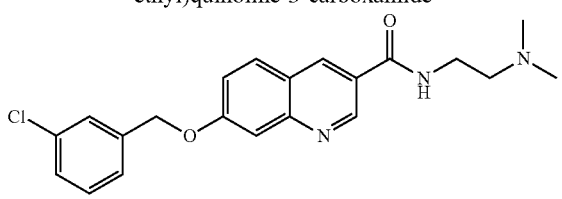

The title compound was prepared in a manner analogous to Example 47, steps A-B, substituting N1,N1-dimethylethane-1,2-diamine for tert-butyl (2-aminoethyl)carbamate in Step B. $^1$H NMR (400 MHz, DMSO-d$_6$) δ 9.33-9.25 (m, 1H), 9.05-8.96 (m, 1H), 8.86-8.79 (m, 1H), 8.10-8.04 (m, 1H), 7.67-7.64 (m, 1H), 7.60-7.58 (m, 1H), 7.57-7.45 (m, 4H), 5.39 (s, 2H), 3.73-3.58 (m, 2H), 3.22-2.98 (m, 2H), 2.83-2.62 (m, 6H). [M+H]=384.3.

Example 50

(7-((3-Chlorobenzyl)oxy)quinolin-3-yl)methanamine

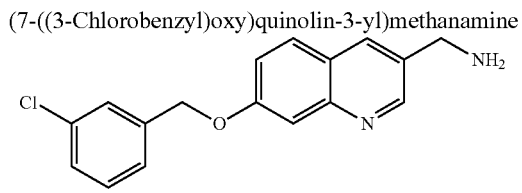

Step A. (7-((3-Chlorobenzyl)oxy)quinolin-3-yl)methyl methanesulfonate. To a solution of (7-((3-chlorobenzyl)oxy)quinolin-3-yl)methanol (Example 35, 55 mg, 0.18 mmol) in THF (1.8 mL) was added DIPEA (0.064 mL, 0.37 mmol), followed by methanesulfonyl chloride (0.014 mL, 0.18 mmol). The reaction was stirred at ambient temperature overnight. The crude reaction was loaded directly onto a column, purification (FCC, SiO$_2$, 0-40%, EtOAc/hexanes) afforded the title compound as a white solid (44 mg, 76%). $^1$H NMR (400 MHz, CDCl$_3$) δ 8.85 (d, J=2.3 Hz, 1H), 8.10 (s, 1H), 7.74 (d, J=9.0 Hz, 1H), 7.48 (d, J=9.4 Hz, 2H), 7.41-7.28 (m, 4H), 5.20 (s, 2H), 4.76 (s, 2H). [M+H]=318.2

Step B. (7-((3-Chlorobenzyl)oxy)quinolin-3-yl)methanamine. A solution of 7-((3-chlorobenzyl)oxy)quinolin-3-yl) methyl methanesulfonate (44 mg, 0.14 mmol) in a 7 N solution of ammonia in MeOH was heated in the microwave at 100° C. for one hour. The crude reaction mixture was concentrated under reduced pressure. DCM was added and the precipitate was collected to afford the title compound as a pale yellow solid (24 mg, 59%). $^1$H NMR (400 MHz, DMSO-d$_6$) δ 8.95 (d, J=2.3 Hz, 1H), 8.41 (d, J=2.0 Hz, 1H), 7.97 (d, J=9.0 Hz, 1H), 7.64 (s, 1H), 7.57-7.42 (m, 5H), 5.36 (s, 2H), 4.25 (s, 2H). [M+H]=299.2.

Example 51

2-(7-((3-Chlorobenzyl)oxy)quinolin-3-yl)acetamide

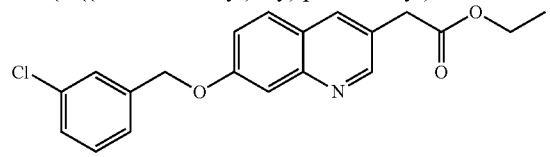

Procedure 1. The title compound was prepared in a manner analogous to Example 1, substituting 3-chlorobenzyl chloride for 4-chlorobenzyl chloride and ethyl 2-(7-hydroxyquinolin-3-yl)acetate (Intermediate 2) for ethyl 7-hydroxyquinoline-3-carboxylate (Intermediate 1). $^1$H NMR (400 MHz, CDCl$_3$) δ 8.76 (d, J=2.3 Hz, 1H), 8.02 (s, 1H), 7.71 (d, J=9.0 Hz, 1H), 7.52-7.43 (m, 2H), 7.32 (dd, J=12.7, 6.5 Hz, 4H), 5.19 (s, 2H), 4.18 (q, J=7.0 Hz, 2H), 3.77 (s, 2H), 1.26 (t, J=7.0 Hz, 3H). [M+H]=356.2.

Procedure 2. Step A: 7-((3-Chlorobenzyl)oxy)-3,4-dihydroquinolin-2(1H)-one. To a slurry of 7-hydroxy-3,4-dihydroquinolin-2(1H)-one (32.4 g, 0.20 mol), and K$_2$CO$_3$ (54.92 g, 0.40 mol) in ACN (162 mL) was added 3-chlorobenzyl bromide (26.1 mL, 0.20 mol). The reaction was heated to 60° C.

for 18 h. The reaction mixture was cooled and quenched into 650 mL of ice water and stirred for 20 min. The solid was filtered and dried to furnish a white solid (55.4 g, 97%), which was carried on without further purification to the next step. $^1$H NMR (400 MHz, CDCl$_3$) δ 8.78 (br s, 1H), 7.43 (s, 1H), 7.31 (s, 3H), 7.06 (d, J=8.3 Hz, 1H), 6.58 (dd, J=8.3, 2.3 Hz, 1H), 6.46 (d, J=2.3 Hz, 1H), 5.02 (s, 2H), 2.96-2.84 (m, 2H), 2.63 (t, J=7.5 Hz, 2H). [M+H]=288.1.

Step B: tert-Butyl 7-((3-chlorobenzyl)oxy)-2-oxo-3,4-dihydroquinoline-1(2H)-carboxylate. To a slurry of 7-((3-chlorobenzyl)oxy)-3,4-dihydroquinolin-2(1H)-one (30 g, 0.09 mol) in DCM (153 mL) was added BOC anhydride (22.40 mL, 0.10 mol), triethylamine (12.35 mL, 0.09 mol) and 4-dimethylaminopyridine (0.11 g, 0.90 mmol) at ambient temperature. The resulting slurry was stirred at ambient temperature for 4 h. The reaction was quenched into water (150 mL). The organic layer was separated and washed with 1N aq. HCl (100 mL) and sat. (aq.) ammonium chloride (100 mL) and dried over Na$_2$SO$_4$ and concentrated under reduced pressure to a yellow oil that solidified upon standing. The solid was triturated in hexanes (200 mL) to yield the desired product (28.0 g, 81%), which was carried on without further purification to the next step. $^1$H NMR (400 MHz, CDCl$_3$) δ 7.41 (s, 1H), 7.36-7.28 (m, 3H), 7.08 (d, J=8.3 Hz, 1H), 6.65 (dd, J=8.3, 2.3 Hz, 1H), 6.59 (d, J=2.3 Hz, 1H), 5.02 (s, 2H), 2.95-2.81 (m, 2H), 2.65 (dd, J=8.4, 6.1 Hz, 2H), 1.60 (s, 9H). [M+H]=388.0.

Step C: tert-Butyl 7-((3-chlorobenzyl)oxy)-3-(2-ethoxy-2-oxoethyl)-2-oxo-3,4-dihydroquinoline-1(2H)-carboxylate. To a solution of tert-butyl 7-((3-chlorobenzyl)oxy)-2-oxo-3,4-dihydroquinoline-1(2H)-carboxylate (34 g, 0.09 mol) in THF (50.09 mL) was added a solution of lithium bis(trimethylsilyl)amide (1.06 M in THF, 99.24 mL, 0.11 mol) at −78° C. The reaction was stirred at that temperature for 30 minutes after which ethyl bromoacetate (9.70 mL, 0.09 mol) was added. The reaction was allowed to warm to ambient temperature, stirred overnight and quenched into water (250 mL). The aqueous layer was extracted with EtOAc (2×50 mL) and the combined organic layers were washed with brine and dried over MgSO$_4$. The organics were concentrated under reduced pressure to afford a yellow-brown oil and carried on crude to the next step. $^1$H NMR (400 MHz, CDCl$_3$) δ 7.35 (s, 1H), 7.27-7.22 (m, 3H), 7.02 (d, J=8.4 Hz, 1H), 6.59 (dd, J=8.3, 2.5 Hz, 1H), 6.49 (d, J=2.4 Hz, 1H), 4.95 (s, 2H), 4.12 (q, J=7.2 Hz, 2H), 3.06-2.91 (m, 1H), 2.87-2.70 (m, 2H), 2.60 (d, J=7.5 Hz, 1H), 2.37 (d, J=8.9 Hz, 1H), 1.54-1.44 (m, 9H), 1.26-1.19 (m, 3H). [M+H]=374.2.

Step D: Ethyl 2-(7-((3-chlorobenzyl)oxy)-2-oxo-1,2,3,4-tetrahydroquinolin-3-yl)acetate. To crude tert-butyl 7-((3-chlorobenzyl)oxy)-3-(2-ethoxy-2-oxoethyl)-2-oxo-3,4-dihydroquinoline-1(2H)-carboxylate (115.7 g, 244.1 mmol) was added a 4.0 M 1,4-dioxane hydrochloride solution (200 mL, 0.8 mol) in an ice bath. After addition, the ice bath was removed and the reaction was warmed to ambient temperature. The reaction was concentrated to a yellow oil and azeotroped with toluene (2×250 mL) to furnish a brown oil. The oil was diluted in toluene (400 mL) followed by 2-propanol (400 mL). The resulting white ppt that was formed was filtered and washed with 2-propanol to furnish the desired product as a white solid. The mother liquor was concentrated to a brown solid that was triturated with 2-propanol (400 mL), filtered and washed with 2-propanol to furnish a second crop of product (38.3 g). The two crops were combined to give (50.3 g, 55%) of the title compound. $^1$H NMR (400 MHz, CDCl$_3$) δ 7.88 (s, 1H), 7.43 (s, 1H), 7.35-7.29 (m, 3H), 7.06 (d, J=8.3 Hz, 1H), 6.59 (dd, J=8.3, 2.4 Hz, 1H), 6.39 (d, J=2.4 Hz, 1H), 5.02 (s, 2H), 4.23-4.15 (m, 2H), 3.12-2.92 (m, 3H), 2.92-2.77 (m, 1H), 2.48 (dd, J=16.2, 7.5 Hz, 1H), 1.29 (t, J=7.1 Hz, 3H). [M+H]=374.2.

Step E: Ethyl 2-(7-((3-chlorobenzyl)oxy)-2-oxo-1,2-dihydroquinolin-3-yl)acetate. To a solution of ethyl 2-(7-((3-chlorobenzyl)oxy)-2-oxo-1,2,3,4-tetrahydroquinolin-3-yl)acetate (50.3 g, 134.5 mmol) in chloroform (905.2 mL) was added 4,5-dichloro-3,6-dioxocyclohexa-1,4-diene-1,2-dicarbonitrile (36.65 g, 161.4 mmol). The reaction was poured into 500 mL sat (aq) NaHCO$_3$ and stirred for 15 min. To the resulting slurry was added diatomaceous earth (CELITE®) and the mixture was filtered over CELITE®. The phases were separated and the subsequent CELITE® washes, chloroform (2×400 mL), were used to extract the aqueous layer. The combined organic layers were dried over Na$_2$SO$_4$ and concentrated under reduced pressure to afford a brown/red solid. The solid was triturated in 2-propanol (700 mL) and filtered to furnish the title compound (31.4 g, 55%). $^1$H NMR (400 MHz, DMSO-d$_6$) δ 11.73 (s, 1H), 11.91-11.57 (m, 1H), 7.77 (s, 1H), 7.55 (s, 2H), 7.43 (t, J=4.8 Hz, 3H), 6.87 (s, 2H), 5.17 (s, 2H), 4.06 (d, J=7.0 Hz, 2H), 3.48 (s, 2H), 1.17 (t, J=7.2 Hz, 3H). [M+H]=372.1.

Step F: Ethyl 2-(2-chloro-7-((3-chlorobenzyl)oxy)quinolin-3-yl)acetate. To a slurry of ethyl 2-(7-((3-chlorobenzyl)oxy)-2-oxo-1,2-dihydroquinolin-3-yl)acetate (31.4 g, 0.08 mol) in chloroform (314 mL) at ambient temperature was added oxalyl dichloride (21.7 mL, 0.25 mol) and DMF (0.66 mL, 0.01 mol). The resulting slurry was heated to reflux for 1 h. The reaction was quenched with sat. aqueous NaHCO$_3$ (400 mL). The aqueous layer was extracted with DCM (2×200 mL) and the combined organic layers were washed with brine and dried over Na$_2$SO$_4$. The organic layer was concentrated under reduced pressure to furnish a black solid that was triturated in 1:1 EtOAc:hexanes (400 mL) and filtered. The solid was recrystallized from MeOH to furnish (17.0 g, 52%). Two additional crops of product were acquired from the mother liquor to furnish a total of 27.8 g (84.3%) of the title compound. $^1$H NMR (400 MHz, DMSO-d$_6$) δ 8.34 (s, 1H), 7.93 (d, J=9.0 Hz, 1H), 7.59 (s, 1H), 7.51-7.37 (m, 5H), 5.31 (s, 2H), 4.13 (q, J=7.1 Hz, 2H), 3.94 (s, 2H), 1.19 (t, J=7.1 Hz, 3H). [M+H]=390.2

Step G: Ethyl 2-(7-((3-chlorobenzyl)oxy)quinolin-3-yl)acetate. A solution of ethyl 2-(2-chloro-7-((3-chlorobenzyl)oxy)quinolin-3-yl)acetate (5 g, 12.8 mmol) in THF (50 mL) was degassed with nitrogen for 5 minutes and [1,1'-bis(diphenylphosphino)ferrocene]dichloropalladium(II), complex with dichloromethane (1.36 g, 1.67 mmol) was added, followed by N1,N1,N2,N2-tetramethylethane-1,2-diamine (3.84 mL, 25.6 mmol) and sodium tetrahydroborate (969 mg, 25.6 mmol). The resulting solution was stirred at ambient temperature. After 4 h an additional portion of 1,1'-bis(diphenylphosphino)ferrocene]dichloropalladium(II), complex with dichloromethane (50 mg, 0.06 mmol) and sodium tetrahydroborate (969 mg, 25.6 mmol) were added and stirred overnight. The reaction was quenched into sat. aqueous NH$_4$Cl and extracted with EtOAc (3×30 mL). The combined organic layers were dried over MgSO$_4$ and concentrated under reduced pressure to afford a brown oil. Purification (FCC, SiO$_2$, 0-60%, EtOAc/hexanes) afforded the title compound as a colorless oil (2.5 g, 55%) that crystallized upon standing. $^1$H NMR (400 MHz, CDCl$_3$) 8.76 (d, J=2.3 Hz, 1H), 8.02 (s, 1H), 7.71 (d, J=9.0 Hz, 1H), 7.52-7.43 (m, 2H), 7.32 (dd, J=6.5, 12.7 Hz, 4H), 5.19 (s, 2H), 4.18 (q, J=7.0 Hz, 2H), 3.77 (s, 2H), 1.26 (t, J=7.0 Hz, 3H). [M+H]=356.2.

Example 52

Ethyl 2-(7-((3-fluorobenzyl)oxy)quinolin-3-yl)acetate

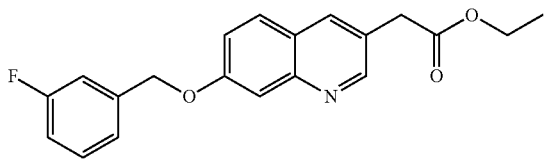 [SMILES: CCOC(=O)Cc1cnc2cc(OCc3cccc(F)c3)ccc2c1]

The title compound was prepared in a manner analogous to Example 1, substituting 3-fluorobenzyl chloride for 4-chlorobenzyl chloride and ethyl 2-(7-hydroxyquinolin-3-yl)acetate (Intermediate 2) for ethyl 7-hydroxyquinoline-3-carboxylate (Intermediate 1). $^1$H NMR (400 MHz, CDCl$_3$) δ 8.76 (d, J=2.3 Hz, 1H), 8.01 (s, 1H), 7.71 (d, J=9.0 Hz, 1H), 7.44 (d, J=2.3 Hz, 1H), 7.40-7.32 (m, 1H), 7.31-7.27 (m, 1H), 7.25-7.18 (m, 2H), 7.07-6.98 (m, 1H), 5.21 (s, 2H), 4.18 (q, J=7.0 Hz, 2H), 3.77 (s, 2H), 1.26 (t, J=7.0 Hz, 3H). [M+H]=340.3.

Example 53

Ethyl 2-(7-((4-fluorobenzyl)oxy)quinolin-3-yl)acetate

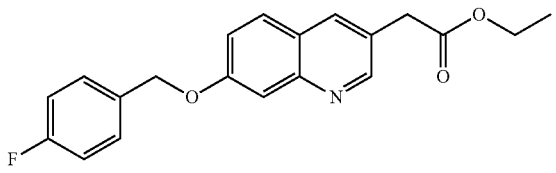 [SMILES: CCOC(=O)Cc1cnc2cc(OCc3ccc(F)cc3)ccc2c1]

The title compound was prepared in a manner analogous to Example 1, substituting 4-fluorobenzyl chloride for 4-chlorobenzyl chloride and ethyl 2-(7-hydroxyquinolin-3-yl)acetate (Intermediate 2) for ethyl 7-hydroxyquinoline-3-carboxylate (Intermediate 1). $^1$H NMR (400 MHz, CDCl$_3$) δ 8.76 (d, J=2.0 Hz, 1H), 8.02 (s, 1H), 7.70 (d, J=9.0 Hz, 1H), 7.51-7.41 (m, 3H), 7.28 (d, J=1.6 Hz, 1H), 7.09 (t, J=8.6 Hz, 2H), 5.17 (s, 2H), 4.23-4.14 (m, 2H), 3.77 (s, 2H), 1.26 (dt, J=1.0, 7.1 Hz, 3H). [M+H]=340.3.

Example 54

Methyl 2-(7-((3-chlorobenzyl)oxy)quinolin-3-yl)acetate

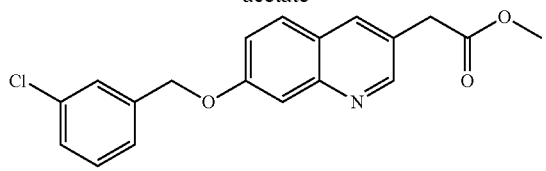

To a solution of ethyl 2-(7-((3-chlorobenzyl)oxy)quinolin-3-yl)acetate (Example 51, 50 mg, 0.14 mmol) in MeOH (3.0 mL) was added K$_2$CO$_3$ (50 mg, 0.36 mmol). The reaction was stirred at ambient temperature for 30 minutes. The reaction was loaded directly onto the column and purification (FCC, SiO$_2$, 0-50%, EtOAc/hexanes) afforded the title compound as a white solid (33 mg, 69%). $^1$H NMR (400 MHz, CDCl$_3$) δ 8.75 (d, J=2.0 Hz, 1H), 8.01 (s, 1H), 7.71 (d, J=9.0 Hz, 1H), 7.49 (s, 1H), 7.45 (d, J=2.7 Hz, 1H), 7.38-7.27 (m, 4H), 5.19 (s, 2H), 3.79 (s, 2H), 3.73 (s, 3H). [M+H]=342.2.

Example 55

2-(7-((3-Chlorobenzyl)oxy)quinolin-3-yl)acetamide

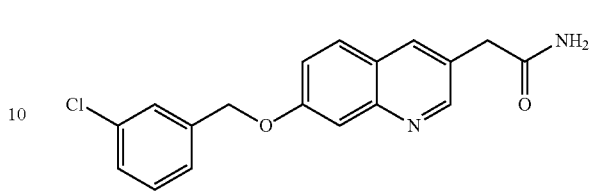

Ethyl 2-(7-((3-chlorobenzyl)oxy)quinolin-3-yl)acetate (Example 51, 100 mg, 0.28 mmol) was dissolved in a 7N solution of ammonia in MeOH (40 mL) and stirred at ambient temperature overnight. The reaction mixture was concentrated under reduced pressure to afford a yellow solid. Et$_2$O was added and the yellow precipitate was collected by filtration. DCM was added and the off white precipitate was isolated by filtration, this was repeated to yield the title compound as an off white solid (59 mg, 64%). $^1$H NMR (400 MHz, DMSO-d$_6$) δ 8.74 (d, J=2.0 Hz, 1H), 8.14 (d, J=2.0 Hz, 1H), 7.92 (d, J=9.0 Hz, 1H), 7.64 (d, J=1.6 Hz, 2H), 7.57-7.44 (m, 4H), 7.37 (dd, J=2.7, 9.0 Hz, 1H), 7.08-7.02 (m, 1H), 5.34 (s, 2H), 3.60 (s, 2H). [M+H]=327.2.

Example 56

2-(7-((3-Chlorobenzyl)oxy)quinolin-3-yl)ethanol

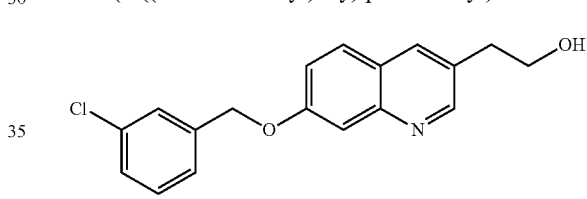

To a cooled, −78° C., solution of ethyl 2-(7-((3-chlorobenzyl)oxy)quinolin-3-yl)acetate (Example 51, 50 mg, 0.14 mmol) in THF (1.5 mL), under an atmosphere of nitrogen, was added LiAlH$_4$ (2.4 M in THF, 0.1 mL, 0.24 mmol). The reaction was stirred for 7 h before being quenched with 1N NaOH (aq.). The crude reaction mixture was filtered through CELITE® and the aqueous layer was extracted with EtOAc. The combined organic fractions were concentrated onto silica and purification (FCC, SiO$_2$, 0-5%, MeOH/DCM) afforded the title compound as a yellow solid (29 mg, 66%). $^1$H NMR (400 MHz, CDCl$_3$) δ 8.71 (d, J=2.0 Hz, 1H), 7.92 (s, 1H), 7.67 (d, J=9.0 Hz, 1H), 7.50 (s, 1H), 7.42 (d, J=2.3 Hz, 1H), 7.38-7.27 (m, 4H), 5.18 (s, 2H), 4.02-3.90 (m, 2H), 3.02 (t, J=6.3 Hz, 2H). [M+H]=314.3.

Example 57

2-(7-((3-Fluorobenzyl)oxy)quinolin-3-yl)acetamide

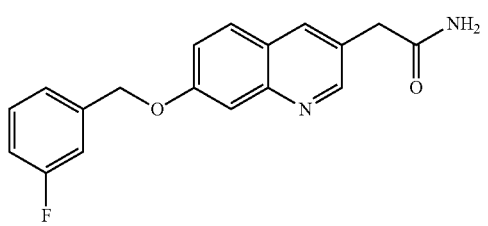 [SMILES: NC(=O)Cc1cnc2cc(OCc3cccc(F)c3)ccc2c1]

The title compound was prepared in a manner analogous to Example 55, substituting ethyl 2-(7-((3-fluorobenzyl)oxy)quinolin-3-yl)acetate (Example 52) for ethyl 2-(7-((3-chlorobenzyl)oxy)quinolin-3-yl)acetate (Example 51). ¹H NMR (400 MHz, DMSO-d₆) δ 8.69 (d, J=2.3 Hz, 1H), 8.08 (d, J=2.0 Hz, 1H), 7.86 (d, J=9.0 Hz, 1H), 7.65-7.54 (m, 1H), 7.50-7.39 (m, 2H), 7.38-7.27 (m, 3H), 7.21-7.13 (m, 1H), 7.03-6.95 (m, 1H), 5.29 (s, 2H), 3.55 (s, 2H). [M+H]=311.3.

Example 58

2-(7-((4-fluorobenzyl)oxy)quinolin-3-yl)acetamide

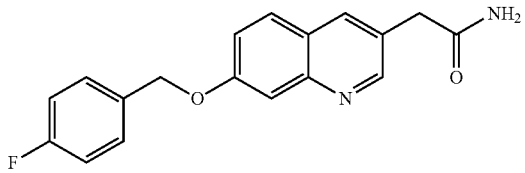 [SMILES: NC(=O)Cc1cnc2cc(OCc3ccc(F)cc3)ccc2c1]

The title compound was prepared in a manner analogous to Example 55, substituting ethyl 2-(7-((4-fluorobenzyl)oxy)quinolin-3-yl)acetate (Example 53) for ethyl 2-(7-((3-chlorobenzyl)oxy)quinolin-3-yl)acetate (Example 51). ¹H NMR (400 MHz, DMSO-d₆) δ 8.74 (d, J=2.3 Hz, 1H), 8.13 (s, 1H), 7.90 (d, J=8.6 Hz, 1H), 7.71-7.58 (m, 3H), 7.50 (d, J=2.3 Hz, 1H), 7.37-7.23 (m, 3H), 7.11-6.97 (m, 1H), 5.29 (s, 2H), 3.60 (s, 2H). [M+H]=311.3.

Example 59

Ethyl 2-(7-((3-chlorobenzyl)oxy)quinolin-3-yl)-2-methylpropanoate

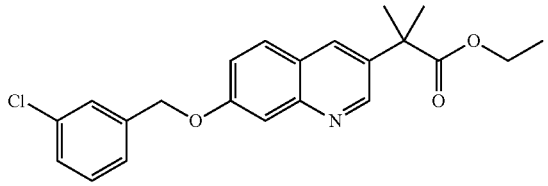 [SMILES: CCOC(=O)C(C)(C)c1cnc2cc(OCc3cccc(Cl)c3)ccc2c1]

To a cooled solution, 0° C., under an atmosphere of nitrogen, of ethyl 2-(7-((3-chlorobenzyl)oxy)quinolin-3-yl)acetate (Example 51, procedure 1, 390 mg, 1.1 mmol) in THF (11 mL) was added KHMDS (5.48 mL, 0.5 M soln. in toluene, 2.74 mmol). The reaction mixture was stirred at 0° C. for one hour. Methyl iodide (283 μL, 4.54 mmol) was added and the reaction was warmed to ambient temperature. After 3 h the reaction was quenched by the addition of saturated ammonium chloride solution and the organics were extracted with EtOAc. The combined organic extracts were washed with brine and concentrated onto silica. Purification (FCC, SiO₂, 0-40%, EtOAc/hexanes) afforded the title compound as a clear oil (300 mg, 71%). ¹H NMR (400 MHz, CDCl₃) δ 8.84 (d, J=2.7 Hz, 1H), 8.00 (d, J=2.3 Hz, 1H), 7.71 (d, J=8.6 Hz, 1H), 7.49 (s, 1H), 7.43 (d, J=2.3 Hz, 1H), 7.32 (d, J=5.9 Hz, 4H), 5.19 (s, 2H), 4.14 (q, J=7.0 Hz, 2H), 1.69 (s, 6H), 1.18 (t, J=7.0 Hz, 3H). [M+H]=384.3.

Example 60

2-(7-((3-Chlorobenzyl)oxy)quinolin-3-yl)-2-methylpropan-1-ol

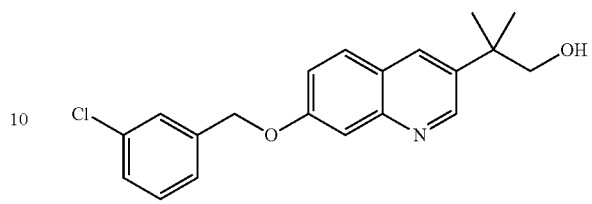

The title compound was prepared in a manner analogous to Example 56, substituting ethyl 2-(7-((3-chlorobenzyl)oxy)quinolin-3-yl)-2-methylpropanoate (Example 59) for ethyl 2-(7-((3-chlorobenzyl)oxy)quinolin-3-yl)acetate (Example 51). ¹H NMR (400 MHz, CDCl₃) δ 8.89 (d, J=2.0 Hz, 1H), 8.00 (d, J=2.3 Hz, 1H), 7.67 (d, J=9.0 Hz, 1H), 7.50 (s, 1H), 7.40-7.29 (m, 4H), 7.24 (d, J=2.7 Hz, 1H), 5.18 (s, 2H), 3.75 (s, 2H), 1.45 (s, 6H). [M+H]=342.3.

Example 61

2-(7-((3-Chlorobenzyl)oxy)quinolin-3-yl)-2-methylpropanamide

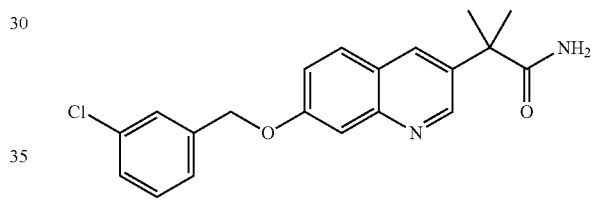

Step A: 2-(7-((3-Chlorobenzyl)oxy)quinolin-3-yl)-2-methylpropanoic acid. To a solution of ethyl 2-(7-((3-chlorobenzyl)oxy)quinolin-3-yl)-2-methylpropanoate (Example 59, 300 mg, 0.78 mmol) in THF (2.6 mL) and MeOH (2.6 mL) was added LiOH (54 mg, 2.25 mmol) in H₂O (2.6 mL). The reaction was stirred at ambient temperature overnight. The solvents were removed under reduced pressure, 10% HCl (aq.) (5 mL) was added and the precipitate was collected and dried under vacuum, the crude product was used without further purification in the next step.

Step B: 2-(7-((3-Chlorobenzyl)oxy)quinolin-3-yl)-2-methylpropanoyl chloride. To a solution of 2-(7-((3-chlorobenzyl)oxy)quinolin-3-yl)-2-methylpropanoic acid in DCM (8 mL) was added oxalyl chloride (208 μL, 2.34 mmol) followed by 3 drops of DMF. After 30 minutes, additional oxalyl chloride (2 mL, 22.5 mmol) was added. After 30 minutes stirring at ambient temperature the reaction was concentrated under reduced pressure and dried under high vacuum to afford the title compound as an oil. The crude product was used without further purification in the next step.

Step C: 2-(7-((3-Chlorobenzyl)oxy)quinolin-3-yl)-2-methylpropanamide. To a solution of 2-(7-((3-chlorobenzyl)oxy)quinolin-3-yl)-2-methylpropanoyl chloride in THF (3 mL) was added ammonium hydroxide (10 mL). The reaction was stirred overnight at ambient temperature. The reaction mixture was concentrated onto silica and purification (FCC, SiO₂, 0-10%, MeOH/DCM) afforded the title compound as a white solid (28 mg, 10%). ¹H NMR (400 MHz, CDCl₃) δ 8.88 (d, J=2.7 Hz, 1H), 8.07 (d, J=2.3 Hz, 1H), 7.73 (d, J=9.0 Hz, 1H), 7.49 (s, 1H), 7.45 (d, J=2.3 Hz, 1H), 7.39-7.27 (m, 4H), 5.34-5.22 (m, 2H), 5.19 (s, 2H), 1.71 (s, 6H). [M+H]=355.3.

Example 62

2-(7-((2-(Trifluoromethyl)pyridin-4-yl)methoxy)quinolin-3-yl)acetamide

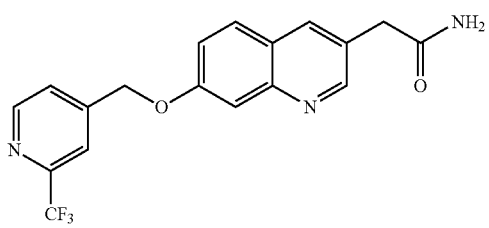 [SMILES: NC(=O)Cc1cnc2cc(OCc3ccnc(C(F)(F)F)c3)ccc2c1]

Step A: Ethyl 2-(7-((2-(trifluoromethyl)pyridin-4-yl)methoxy)quinolin-3-yl)acetate. To a solution of 4-(chloromethyl)-2-(trifluoromethyl)pyridine (162.06 mg, 0.83 mmol) in DMF (5 mL) was added ethyl 2-(7-hydroxyquinolin-3-yl)acetate (Intermediate 2, 150 mg, 0.55 mmol) and $Cs_2CO_3$ (356 mg, 1.10 mmol). The reaction was stirred at ambient temperature for 16 h. A mixture of mono benzylated and bisbenzylated products were observed. Cesium carbonate was filtered off and DMF was removed under reduced pressure. Purification (FCC, $SiO_2$, 0-50%, EtOAc/hexanes) afforded a mixture of methyl and ethyl esters along with 25% of bis-benzylated product. The mixture was advanced into the next reaction.

Step B: 2-(7-((2-(Trifluoromethyl)pyridin-4-yl)methoxy)quinolin-3-yl)acetamide. Ethyl 2-(7-((6-(trifluoromethyl)pyridin-3-yl)methoxy)quinolin-3-yl)acetate (0.15 g, 0.30 mmol) and ammonia in MeOH (7 N, 0.13 g, 7.40 mmol) were combined and stirred at ambient temperature for 3 days. MeOH was removed under reduced pressure. Purification by FCC ($SiO_2$, 0-20%, MeOH/DCM) afforded the title compound as a white solid (0.95 g, 88% yield over 2 steps). $^1$H NMR (400 MHz, DMSO-$d_6$) δ 8.82 (d, J=4.8 Hz, 1H), 8.73 (d, J=2.0 Hz, 1H), 8.13 (s, 1H), 8.04 (s, 1H), 7.93 (d, J=8.8 Hz, 1H), 7.86 (d, J=4.8 Hz, 1H), 7.60 (br. s., 1H), 7.48 (d, J=2.3 Hz, 1H), 7.42 (dd, J=2.4, 8.9 Hz, 1H), 7.00 (br. s., 1H), 5.51 (s, 2H), 3.59 (s, 2H). [M+H]=363.2

Example 63

1-(7-((3-Chlorobenzyl)oxy)quinolin-3-yl)-2-methylpropan-2-ol

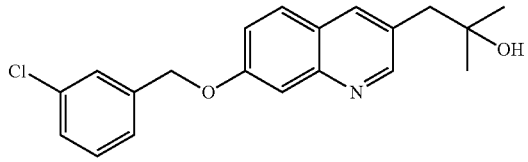 [SMILES: CC(C)(O)Cc1cnc2cc(OCc3cccc(Cl)c3)ccc2c1]

The title compound was prepared in a manner analogous to Example 27, substituting ethyl 2-(7-((3-chlorobenzyl)oxy)quinolin-3-yl)acetate (Example 51) for ethyl 7-[(4-fluorophenyl)methoxy]quinoline-3-carboxylate (Example 2). $^1$H NMR (400 MHz, CDCl$_3$) δ 8.72 (d, J=2.0 Hz, 1H), 7.94 (d, J=2.0 Hz, 1H), 7.70 (d, J=9.0 Hz, 1H), 7.49 (s, 1H), 7.43 (d, J=2.3 Hz, 1H), 7.38-7.26 (m, 4H), 5.18 (s, 2H), 2.91 (s, 2H), 1.28 (s, 6H). [M+H]=342.2.

Example 64

7-((3-Chlorobenzyl)oxy)quinoline-3-carboxamide

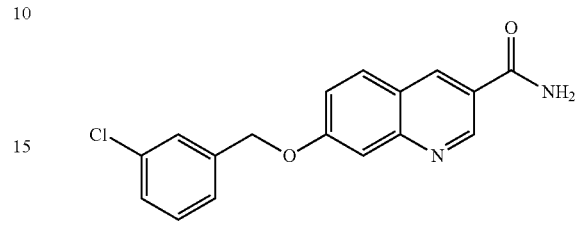

The title compound was prepared in a manner analogous to Example 55, substituting ethyl 7-[(3-chlorophenyl)methoxy]quinoline-3-carboxylate (Example 3) for ethyl 2-(7-((3-chlorobenzyl)oxy)quinolin-3-yl)acetate (Example 51). $^1$H NMR (400 MHz, DMSO-$d_6$) δ 9.33 (s, 1H), 9.13-8.96 (m, 1H), 8.31-8.16 (m, 1H), 7.64 (br. s., 2H), 7.48 (d, J=7.0 Hz, 4H), 6.50-5.65 (m, 2H), 5.40 (s, 2H). [M+H]=313.2.

Example 65

2-{1-[(4-Fluorophenyl)methoxy]-1,5-naphthyridin-3-yl}propan-2-ol

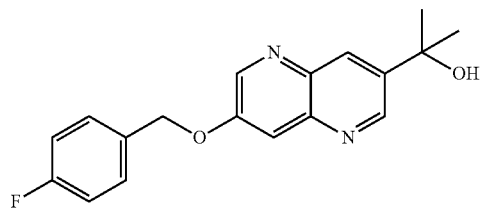 [SMILES: CC(C)(O)c1cnc2cc(OCc3ccc(F)cc3)cnc2c1]

Step A. Ethyl 7-((4-fluorobenzyl)oxy)-1,5-naphthyridine-3-carboxylate. To a solution of ethyl 7-hydroxy-1,5-naphthyridine-3-carboxylate (Intermediate 4, 3.0 g, 13.75 mmol) in DMF (70 mL) was added $Cs_2CO_3$ (8.96 g, 0.03 mol), followed by 4-fluorobenzyl chloride (2.42 mL, 0.02 mol). The reaction was stirred at ambient temperature for 72 h. The crude reaction mixture was poured into EtOAc and water. The aqueous layer was extracted with EtOAc and the combined organic fractions were washed with brine and concentrated under reduced pressure onto silica. Purification (FCC, $SiO_2$, 0-60%, EtOAc/hexanes) afforded the title compound as a white solid (3.0 g, 67%) $^1$H NMR (400 MHz, CDCl$_3$) δ 9.45 (d, J=1.6 Hz, 1H), 8.97 (s, 1H), 8.85 (d, J=2.3 Hz, 1H), 7.72 (d, J=2.0 Hz, 1H), 7.48 (dd, J=5.5, 7.8 Hz, 2H), 7.12 (t, J=8.6 Hz, 2H), 5.22 (s, 2H), 4.48 (q, J=7.3 Hz, 2H), 1.46 (t, J=7.0 Hz, 3H). [M+H]=327.2

Step B: The title compound was prepared in a manner analogous to Example 27, substituting ethyl 7-((4-fluorobenzyl)oxy)-1,5-naphthyridine-3-carboxylate for 7-[(4-fluorophenyl)methoxy]quinoline-3-carboxylate (Example 2). $^1$H NMR (400 MHz, CDCl$_3$) δ 9.07 (d, J=2.0 Hz, 1H), 8.76 (d, J=2.7 Hz, 1H), 8.36 (d, J=2.3 Hz, 1H), 7.66 (d, J=2.7 Hz, 1H), 7.45 (dd, J=5.3, 8.4 Hz, 2H), 7.08 (t, J=8.6 Hz, 2H), 5.16 (s, 2H), 1.70 (s, 6H). [M+H]=313.2.

Example 66

7-[(4-Fluorophenyl)methoxy]-3-(2-hydroxypropan-2-yl)quinolin-1-ium-1-olate

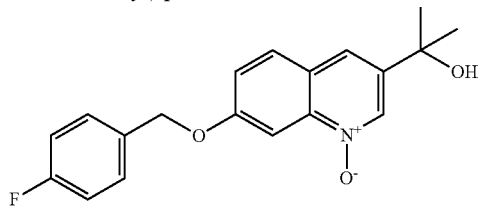

To a cooled, 0° C., solution of 2-(7-((4-fluorobenzyl)oxy)quinolin-3-yl)propan-2-ol (Example 27, 0.063 mg, 0.2 mmol) in DCM (2 mL) was added 3-chloroperoxybenzoic acid (0.068 mg, 0.4 mmol). The reaction was slowly warmed to ambient temperature and stirred for 2 h before being quenched with aq. sat. NaHCO₃. The aqueous layer was extracted with DCM. The combined organic layers were concentrated under reduced pressure onto silica. Purification (FCC, SiO₂, 0-10%, MeOH/DCM) afforded the title compound as a light yellow oil (51 mg, 82%). ¹H NMR (400 MHz, CDCl₃) δ 8.61 (d, J=1.5 Hz, 1H), 7.94 (d, J=2.5 Hz, 1H), 7.60-7.37 (m, 3H), 7.36-7.23 (m, 1H), 7.22-7.04 (m, 3H), 5.22 (s, 2H), 1.62 (s, 6H). [M+H]=328.2.

Example 67

7-[(3-Fluorophenyl)methoxy]-1,5-naphthyridine-3-carboxamide

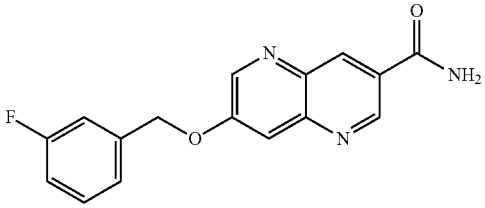 [SMILES: NC(=O)c1cnc2cc(OCc3cccc(F)c3)cnc2c1]

Step A. Ethyl 7-((3-fluorobenzyl)oxy)-1,5-naphthyridine-3-carboxylate. To a solution of ethyl 7-hydroxy-1,5-naphthyridine-3-carboxylate (Intermediate 4, 1.0 g, 4.59 mmol) in DMF (20 mL) was added Cs₂CO₃ (2.2 g, 6.75 mmol), followed by 3-fluorobenzyl chloride (0.6 mL, 5.02 mmol). The reaction was stirred at ambient temperature for 72 h. The crude reaction mixture was poured into EtOAc and water. The aqueous later was extracted with EtOAc and the combined organic fractions were washed with brine and concentrated under reduced pressure onto silica. Purification (FCC, SiO₂, 0-60%, EtOAc/hexanes) afforded the title compound as a white solid (1.0 g, 69%). ¹H NMR (400 MHz, CDCl₃) δ 9.44 (t, J=2.0 Hz, 1H), 9.00-8.94 (m, 1H), 8.88 (t, J=2.3 Hz, 1H), 7.74-7.65 (m, 1H), 7.47-7.33 (m, 1H), 7.28-7.26 (m, 1H), 7.21 (d, J=9.4 Hz, 1H), 7.07 (t, J=8.6 Hz, 1H), 5.25 (s, 2H), 4.59-4.38 (m, 2H), 1.52-1.41 (m, 3H). [M+H]=327.2.

Step B. 7-[(3-Fluorophenyl)methoxy]-1,5-naphthyridine-3-carboxamide. Ethyl 7-((3-fluorobenzyl)oxy)-1,5-naphthyridine-3-carboxylate (100 mg, 0.31 mmol) was suspended in 7N ammonia in MeOH (4.0 mL) and was stirred overnight at ambient temperature. Concentration onto silica and purification (FCC, SiO₂, 0-10%, MeOH/DCM) afforded the title compound as a white solid (11 mg, 12%). ¹H NMR (400 MHz, DMSO-d₆) δ 9.31 (d, J=2.3 Hz, 1H), 8.91 (d, J=2.7 Hz, 1H), 8.82 (d, J=2.0 Hz, 1H), 8.36 (br. s., 1H), 7.92 (d, J=2.7 Hz, 1H), 7.71 (br. s., 1H), 7.51-7.43 (m, 1H), 7.42-7.36 (m, 2H), 7.20 (dt, J=2.3, 8.6 Hz, 1H), 3.30 (d, J=1.2 Hz, 2H). [M+H]=298.2.

Example 68

7-((4-Fluorobenzyl)oxy)-1,5-naphthyridine-3-carboxamide

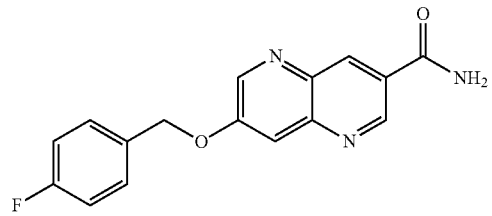 [SMILES: NC(=O)c1cnc2cc(OCc3ccc(F)cc3)cnc2c1]

The title compound was prepared in a manner analogous to Example 67, substituting 4-fluorobenzyl chloride for 3-fluorobenzyl chloride in Step A. ¹H NMR (400 MHz, DMSO-d₆) δ 9.31 (d, J=2.0 Hz, 1H), 8.87 (d, J=2.7 Hz, 1H), 8.82 (d, J=2.0 Hz, 1H), 8.43-8.28 (m, 1H), 7.93 (d, J=2.7 Hz, 1H), 7.74-7.66 (m, 1H), 7.60 (dd, J=5.9, 8.2 Hz, 2H), 7.26 (t, J=8.6 Hz, 2H), 5.35 (s, 2H). [M+H]=298.2.

Example 69

7-((3-Chlorobenzyl)oxy)-1,5-naphthyridine-3-carboxamide

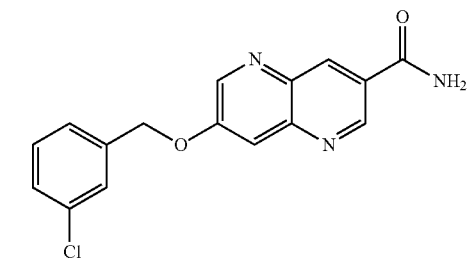 [SMILES: NC(=O)c1cnc2cc(OCc3cccc(Cl)c3)cnc2c1]

The title compound was prepared in a manner analogous to Example 67, substituting 3-chlorobenzyl chloride for 3-fluorobenzyl chloride in Step A. ¹H NMR (400 MHz, DMSO-d₆) δ 9.31 (d, J=2.0 Hz, 1H), 8.90 (d, J=2.7 Hz, 1H), 8.82 (dd, J=0.8, 2.0 Hz, 1H), 8.40-8.28 (m, 1H), 7.93-7.88 (m, 1H), 7.74-7.66 (m, 1H), 7.63 (s, 1H), 7.53-7.39 (m, 3H), 5.40-5.37 (m, 2H). [M+H]=314.1

Example 70

7-((3,4-Difluorobenzyl)oxy)-1,5-naphthyridine-3-carboxamide

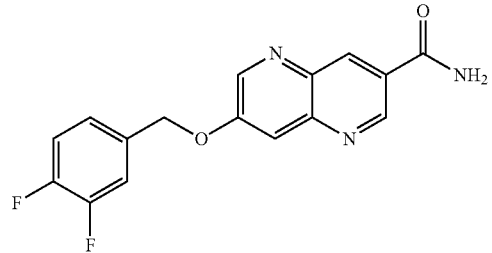 [SMILES: NC(=O)c1cnc2cc(OCc3ccc(F)c(F)c3)cnc2c1]

The title compound was prepared in a manner analogous to Example 67, substituting 3,4-difluorobenzyl chloride for 3-fluorobenzyl chloride in Step A. ¹H NMR (400 MHz, DMSO-d₆) δ 9.32 (d, J=2.3 Hz, 1H), 8.89 (d, J=2.7 Hz, 1H), 8.82 (d, J=2.0 Hz, 1H), 8.36 (br s, 1H), 7.93 (d, J=2.7 Hz, 1H), 7.71 (br s, 1H), 7.68-7.60 (m, 1H), 7.50 (td, J=8.4, 10.7 Hz, 1H), 7.44-7.34 (m, 1H), 5.36 (s, 2H). [M+H]=316.2.

Example 71

7-[(3-Chloro-4-fluorophenyl)methoxy]-1,5-naphthyridine-3-carboxamide

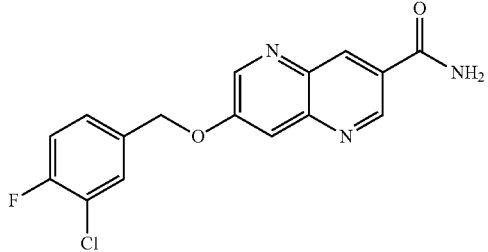 [SMILES: NC(=O)c1cnc2cc(OCc3ccc(F)c(Cl)c3)cnc2c1]

The title compound was prepared in a manner analogous to Example 67, substituting 3-chloro-4-fluorobenzyl chloride for 3-fluorobenzyl chloride in Step A. ¹H NMR (400 MHz, DMSO-d₆) δ 9.32 (d, J=2.3 Hz, 1H), 8.90 (d, J=2.7 Hz, 1H), 8.82 (d, J=1.6 Hz, 1H), 8.39-8.33 (m, 1H), 7.93 (d, J=2.3 Hz, 1H), 7.81 (dd, J=2.2, 7.2 Hz, 1H), 7.74-7.67 (m, 1H), 7.60-7.55 (m, 1H), 7.51-7.43 (m, 1H), 5.36 (s, 2H). [M+H]=332.2.

Example 72

7-[(3-Chlorophenyl)methoxy]-N-methyl-1,5-naphthyridine-3-carboxamide

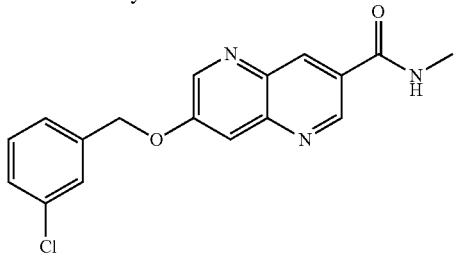

The title compound was prepared in a manner analogous to Example 67, substituting 3-chlorobenzyl chloride for 3-fluorobenzyl chloride in Step A and substituting a 2.0 M solution of methylamine in MeOH for the ammonia solution in Step B. ¹H NMR (400 MHz, DMSO-d₆) δ 9.31 (d, J=2.0 Hz, 1H), 8.98-8.69 (m, 3H), 7.94 (d, J=2.5 Hz, 1H), 7.65 (s, 1H), 7.57-7.35 (m, 3H), 5.41 (s, 2H), 2.87 (d, J=4.5 Hz, 3H). [M+H]=328.6.

Example 73

(7-((3,4-Difluorobenzyl)oxy)-1,5-naphthyridin-3-yl)methanol

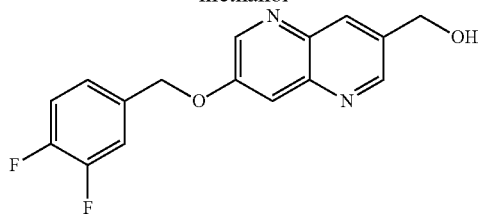

Step A. Ethyl 7-((3,4-difluorobenzyl)oxy)-1,5-naphthyridine-3-carboxylate. To a solution of ethyl 7-hydroxy-1,5-naphthyridine-3-carboxylate (Intermediate 4, 1.0 g, 4.5 mmol) in DMF (20 mL) was added Cs₂CO₃ (2.2 g, 6.75 mmol), followed by 3,4-difluorobenzyl bromide (0.682 mL, 5.02 mmol). The reaction was stirred at ambient temperature for 72 h. The crude reaction mixture was poured into EtOAc and water. The aqueous layer was extracted with EtOAc and the combined organic fractions were washed with brine and concentrated under reduced pressure onto silica. Purification (FCC, SiO₂, 0-60%, EtOAc/hexanes) afforded the title compound as a white solid (1.05 g, 64%) ¹H NMR (400 MHz, CDCl₃) δ 9.48-9.41 (m, 1H), 8.97 (s, 1H), 8.89-8.82 (m, 1H), 7.69 (s, 1H), 7.37-7.29 (m, 1H), 7.25-7.19 (m, 2H), 5.20 (s, 2H), 4.54-4.40 (m, 2H), 1.51-1.41 (m, 3H). [M+H]=345.2.

Step B. (7-((3,4-Difluorobenzyl)oxy)-1,5-naphthyridin-3-yl)methanol. To a solution of ethyl 7-((3,4-difluorobenzyl)oxy)-1,5-naphthyridine-3-carboxylate (0.3 g, 0.87 mmol) in THF (6 mL) at 0° C. and under nitrogen atmosphere was added lithium aluminum hydride (0.4 mL, 0.8 mmol, 2 M in THF). The mixture was allowed to warm to ambient temperature and stirred at ambient temperature for an additional 15 h. The reaction was quenched with water slowly and pH adjusted to ~3 with 1 M HCl. The resulting mixture was extracted with EtOAc and the organic layer separated, washed with brine, dried and concentrated under reduced pressure. The pH of the aqueous layer was adjusted to ~8 with saturated NaHCO₃ solution and the resulting suspension filtered. The filtered solid combined with the previous product were purified (FCC, SiO₂, 0-100%, EtOAc/hexanes) to afford the title compound as a yellow solid (90 mg, 27%). ¹H NMR (400 MHz, DMSO-d₆) δ 8.88 (d, J=1.6 Hz, 1H), 8.80 (d, J=2.3 Hz, 1H), 8.23 (s, 1H), 7.86 (d, J=2.7 Hz, 1H), 7.69-7.58 (m, 1H), 7.53-7.44 (m, 1H), 7.40 (br. s., 1H), 5.32 (s, 2H), 4.73 (s, 2H). [M+H]=303.3.

Example 74

2-{7-[(3,4-Difluorophenyl)methoxy]-1,5-naphthyridin-3-yl}acetonitrile

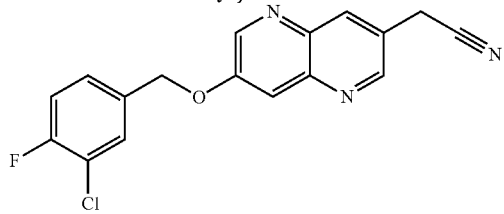

Step A. (7-((3,4-difluorobenzyl)oxy)-1,5-naphthyridin-3-yl)methyl methanesulfonate. To a solution of (7-((3,4-difluorobenzyl)oxy)-1,5-naphthyridin-3-yl)methanol (Example 73, 90 mg, 0.3 mmol) in DCM (4 mL) was added methanesulfonyl chloride (0.05 mL, 0.61 mmol) followed by TEA (0.06 mL, 0.43 mmol). The reaction mixture was stirred at RT for 1 h and quenched with saturated NaHCO₃ solution. The mixture was extracted with DCM (2×) and the combined organic layers were dried, filtered and concentrated under reduced pressure. Purification (FCC, SiO₂, 0-80%, EtOAc/hexanes) afforded the title compound as a white solid (73 mg, 64%). [M+H]=381.1.

Step B. 2-{7-[(3,4-Difluorophenyl)methoxy]-1,5-naphthyridin-3-yl}acetonitrile. A solution of (7-((3,4-difluorobenzyl)oxy)-1,5-naphthyridin-3-yl)methyl methanesulfonate (73 mg, 0.19 mmol) and sodium cyanide (12 mg, 0.25 mmol) in DMSO (2 mL) was heated at 60° C. for 15 min. The reaction was cooled to RT and then diluted with water. The resulting light brown solid was filtered to afford the desired product (45 mg, 75%). ¹H NMR (400 MHz, DMSO-d$_6$) δ 8.89 (s, 1H), 8.84 (d, J=2.3 Hz, 1H), 8.32 (s, 1H), 7.90 (d, J=2.3 Hz, 1H), 7.69-7.59 (m, 1H), 7.53-7.44 (m, 1H), 7.43-7.36 (m, 1H), 5.33 (s, 2H), 4.30 (s, 2H). [M+H]=312.15

Example 75

3-[(4-Fluorophenyl)methoxy]-7-(2-fluoropropan-2-yl)-1,5-naphthyridine

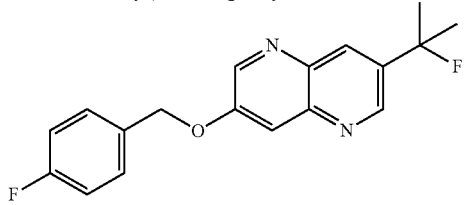 [SMILES: CC(C)(F)c1cnc2cc(OCc3ccc(F)cc3)cnc2c1]

The title compound was prepared in a manner analogous to Example 41, substituting 2-(7-((4-fluorobenzyl)oxy)-1,5-naphthyridin-3-yl)propan-2-ol (Example 65) for 2-(7-((4-fluorobenzyl)oxy)quinolin-3-yl)propan-2-ol (Example 27). $^1$H NMR (400 MHz, CDCl$_3$) δ 9.02 (d, J=2.0 Hz, 1H), 8.84 (d, J=2.8 Hz, 1H), 8.33 (s, 1H), 7.73 (d, J=2.8 Hz, 1H), 7.51 (dd, J=5.5, 8.3 Hz, 2H), 7.15 (t, J=8.7 Hz, 2H), 5.24 (s, 2H), 2.01-1.78 (m, 6H). [M+H]=315.2.

Example 76

2-{7-[(3-Fluorophenyl)methoxy]-1,5-naphthyridin-3-yl}propan-2-ol

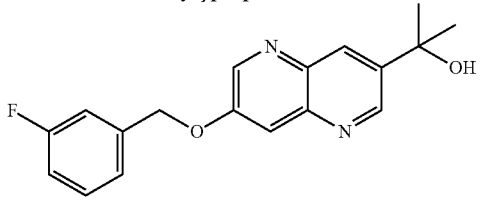

The title compound was prepared in a manner analogous to Example 27, substituting ethyl 7-((3-fluorobenzyl)oxy)-1,5-naphthyridine-3-carboxylate for ethyl 7-[(4-fluorophenyl)methoxy]quinoline-3-carboxylate (Example 2). $^1$H NMR (400 MHz, CDCl$_3$) δ 9.09 (d, J=2.3 Hz, 1H), 8.80 (d, J=2.7 Hz, 1H), 8.40-8.36 (m, 1H), 7.66 (d, J=2.7 Hz, 1H), 7.42-7.33 (m, 1H), 7.28-7.25 (m, 1H), 7.23-7.16 (m, 1H), 7.09-6.99 (m, 1H), 5.22 (s, 2H), 1.71 (s, 6H). [M+H]=313.2.

Example 77

2-{7-[(3,4-Difluorophenyl)methoxy]-1,5-naphthyridin-3-yl}propan-2-ol

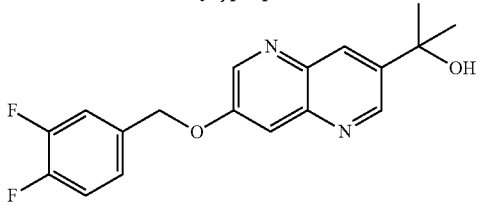

The title compound was prepared in a manner analogous to Example 27, substituting ethyl 7-((3,4-difluorobenzyl)oxy)-1,5-naphthyridine-3-carboxylate (Example 73, product from Step A) for ethyl 7-[(4-fluorophenyl)methoxy]quinoline-3-carboxylate (Example 2). $^1$H NMR (400 MHz, CDCl$_3$) δ 9.09 (d, J=2.3 Hz, 1H), 8.78 (d, J=2.7 Hz, 1H), 8.38 (d, J=2.3 Hz, 1H), 7.65 (d, J=2.7 Hz, 1H), 7.39-7.27 (m, 1H), 7.22-7.15 (m, 2H), 5.16 (s, 2H), 1.71 (d, J=0.8 Hz, 6H). [M+H]=331.2.

Example 78

2-{7-[(3-Chloro-4-fluorophenyl)methoxy]-1,5-naphthyridin-3-yl}propan-2-ol

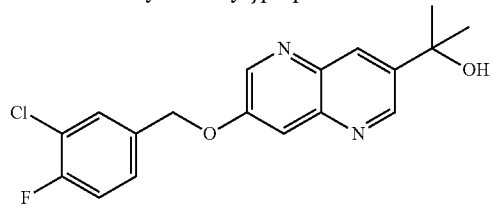

The title compound was prepared in a manner analogous to Example 27, substituting ethyl 7-((3-chloro-4-fluorobenzyl)oxy)-1,5-naphthyridine-3-carboxylate for ethyl 7-[(4-fluorophenyl)methoxy]quinoline-3-carboxylate (Example 2). $^1$H NMR (400 MHz, CDCl$_3$) δ 9.12 (d, J=2.3 Hz, 1H), 8.85-8.72 (m, 1H), 8.46-8.36 (m, 1H), 7.70-7.64 (m, 1H), 7.61-7.53 (m, 1H), 7.42-7.34 (m, 1H), 7.24-7.17 (m, 1H), 5.18 (s, 2H). [M+H]=347.1

Example 79

2-{7-[(3-Chlorophenyl)methoxy]-1,5-naphthyridin-3-yl}propan-2-ol

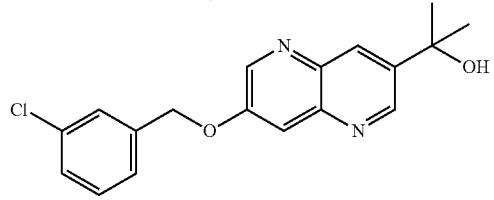 [SMILES: CC(C)(O)c1cnc2cc(OCc3cccc(Cl)c3)cnc2c1]

The title compound was prepared in a manner analogous to Example 27, substituting ethyl 7-((3-chlorobenzyl)oxy)-1,5-naphthyridine-3-carboxylate for ethyl 7-[(4-fluorophenyl)methoxy]quinoline-3-carboxylate (Example 2). $^1$H NMR (400 MHz, CDCl$_3$) δ 9.09 (t, J=2.0 Hz, 1H), 8.80 (t, J=2.3 Hz, 1H), 8.44-8.35 (m, 1H), 7.66 (s, 1H), 7.49 (s, 1H), 7.41-7.31 (m, 3H), 5.20 (s, 2H), 1.79-1.68 (m, 6H). [M+H]=329.2.

Example 80

2-(7-((3,4-Difluorobenzyl)oxy)-1,5-naphthyridin-3-yl)acetamide

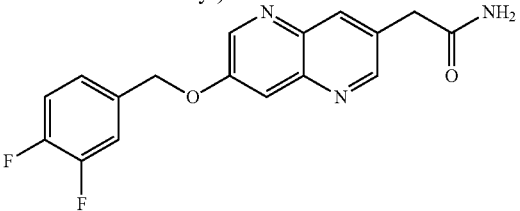

Step A. 3-Bromo-7-((3,4-difluorobenzyl)oxy)-1,5-naphthyridine. To a mixture of (3,4-difluorophenyl)methanol (119 μL, 1.04 mmol) and 3,7-dibromo-1,5-naphthyridine (Intermediate 3, 200 mg, 0.69 mmol) in NMP (1 mL) at 100° C. under a nitrogen atmosphere was added a slurry of sodium hydride (69.45 mg, 1.74 mmol) in NMP (1 mL) dropwise. The solution was allowed to stir at 100° C. for 3 h. Upon completion the reaction was cooled and water was added to afford a solid precipitate. The solid was collected by filtration to give the title compound (130 mg, 53.3%) as a crude brown solid, which used without further purification. ¹H NMR (400 MHz, CDCl₃) δ 8.93 (s, 1H), 8.82 (d, J=2.5 Hz, 1H), 8.54 (s, 1H), 7.66 (d, J=2.0 Hz, 1H), 7.41-7.31 (m, 1H), 7.27-7.16 (m, 2H), 5.19 (s, 2H). [M+H]=351.1.

Step B. Ethyl 2-(7-((3,4-difluorobenzyl)oxy)-1,5-naphthyridin-3-yl)acetate. 3-Bromo-7-((3,4-difluorobenzyl)oxy)-1,5-naphthyridine (3.20 g, 9.11 mmol), Pd₂(dba)₃ (41.72 mg, 0.05 mmol), tri-tert-butylphosphonium tetrafluoroborate (290.84 mg, 1 mmol), potassium phosphate (5.42 g, 25.52 mmol), 1,4,7,10,13,16-hexaoxacyclooctadecane (1.2 g, 4.56 mmol), and diethyl malonate (9.17 mL, 60.15 mmol) were added to a microwave vial, which was capped and purged with nitrogen for several minutes then heated to 115° C. for 19 h. The reaction was cooled to ambient temperature then water and EtOAc were added. The layers were separated and the aqueous solution was extracted with EtOAc and DCM. The combined organic layers were washed with brine then dried (Na₂SO₄). The solvent was removed under reduced pressure. Purification (FCC, SiO₂, 0-70%, EtOAc/hexanes) afforded the title compound as a pure beige solid (1.76 g, 53.8%). ¹H NMR (400 MHz, CDCl₃) δ 8.84 (dd, J=18.1, 2.5 Hz, 2H), 8.27 (d, J=1.4 Hz, 1H), 7.68 (d, J=2.6 Hz, 1H), 7.47-7.30 (m, 1H), 7.26-7.17 (m, 2H), 5.20 (s, 2H), 4.22 (q, J=7.2 Hz, 2H), 3.86 (s, 2H), 1.30 (t, J=7.2 Hz, 3H). [M+H]=359.2.

Step C: 2-(7-((3,4-difluorobenzyl)oxy)-1,5-naphthyridin-3-yl)acetamide. Ethyl 2-(7-((3,4-difluorobenzyl)oxy)-1,5-naphthyridin-3-yl)acetate (1.95 g, 5.44 mmol) was treated with a solution of ammonia in MeOH (7 M, 30 mL, 245 mmol). The slurry was stirred at ambient temperature for 30 h. The resulting precipitate was filtered and washed with MeOH to give the title compound as a cream colored solid. The crude product was azeotrope dried with toluene to remove traces of ammonia then dried on high vacuum for 48 h to give the title compound (1.79 g, 82%) as a pure white solid. ¹H NMR (400 MHz, DMSO-d₆) δ 8.81 (t, J=2.0 Hz, 2H), 8.21 (d, J=1.4 Hz, 1H), 7.88 (d, J=2.6 Hz, 1H), 7.75-7.58 (m, 2H), 7.50 (td, J=8.4, 10.7 Hz, 1H), 7.45-7.36 (m, 1H), 7.05 (br s, 1H), 5.34 (s, 2H), 3.66 (s, 2H). [M+H]=330.2.

Example 81

2-(7-((6-(Trifluoromethyl)pyridin-2-yl)methoxy)-1,5-naphthyridin-3-yl)acetamide

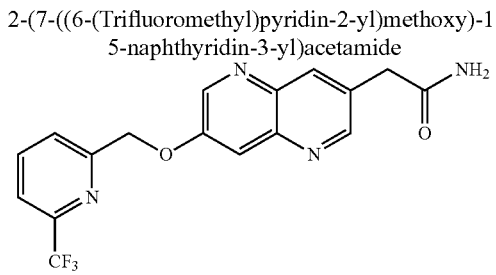

The title compound was prepared in a manner analogous to Example 80, substituting (6-(trifluoromethyl)pyridin-2-yl)methanol for (3,4-difluorophenyl)methanol in Step A. ¹H NMR (400 MHz, DMSO-d₆) δ 8.88 (d, J=2.9 Hz, 1H), 8.82 (d, J=1.9 Hz, 1H), 8.27-8.14 (m, 2H), 7.98 (d, J=7.9 Hz, 1H), 7.95-7.88 (m, 2H), 7.64 (br s, 1H), 7.05 (br. s., 1H), 5.53 (s, 2H), 3.66 (s, 2H). [M+H]=363.2.

Example 82

2-(7-((3-Chlorobenzyl)oxy)-2-oxo-1,2,3,4-tetrahydroquinolin-3-yl)acetamide

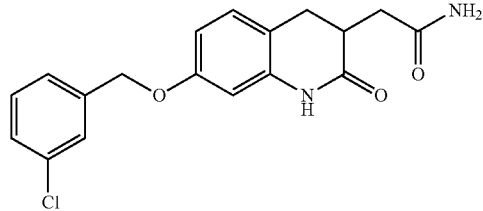 [SMILES: NC(=O)CC1Cc2ccc(OCc3cccc(Cl)c3)cc2NC1=O]

Ethyl 2-(7-((3-chlorobenzyl)oxy)-2-oxo-1,2,3,4-tetrahydroquinolin-3-yl)acetate (Example 51, product from Step D, 200 mg, 0.54 mmol) was dissolved in a 7 N solution of ammonia in methanol (10 mL) and stirred at room temperature for 2 weeks. The resulting precipitate was collected by filtration, washed with methanol (3 mL) and was dried under vacuum to give the title compound as a white solid (111 mg, 60%). ¹H NMR (400 MHz, DMSO-d₆) δ 10.08 (s, 1H), 7.53-7.33 (m, 5H), 7.06 (d, J=8.3 Hz, 1H), 6.85 (br s, 1H), 6.57 (dd, J=2.4, 8.3 Hz, 1H), 6.51 (d, J=2.4 Hz, 1H), 5.05 (s, 2H), 2.93-2.70 (m, 2H), 2.71-2.54 (m, 2H), 2.11 (dd, J=8.5, 15.2 Hz, 1H). [M+H]=345.1.

Example 83

2-(7-((3-Chlorobenzyl)oxy)-2-oxo-1,2-dihydroquinolin-3-yl)acetamide

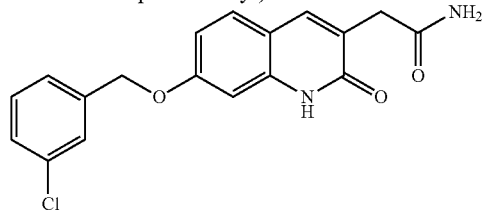

Ethyl 2-(7-((3-chlorobenzyl)oxy)-2-oxo-1,2-dihydroquinolin-3-yl)acetate (Example 51, product from Step E, 200 mg, 0.54 mmol) was dissolved in a 7 N solution of ammonia in methanol (10 mL) and stirred at room temperature for 2 weeks. The resulting precipitate was collected by filtration, washed with methanol (3 mL) and was dried under vacuum to give the title compound as a white solid (136 mg, 74%). ¹H NMR (400 MHz, DMSO-d₆) δ 11.68 (s, 1H), 7.70 (s, 1H), 7.54 (s, 2H), 7.43 (s, 3H), 7.35 (br s, 1H), 6.86 (s, 2H), 6.85 (br s, 1H), 5.16 (s, 2H), 3.27 (s, 2H). [M+H]=343.1.

Pharmacological Examples

The present disclosure will be further illustrated by the following pharmacological examples. These examples are understood to be exemplary only and are not intended to limit the scope of the invention disclosed herein.

Enzymatic Assay

The MAO enzymatic assay was performed according to the fluorometric method described by Matsumoto and colleagues (Matsumoto et al., *Clin. Biochem.* 1985, 18, 126-129) with the following modifications. Human recombinant MAO-A and MAO-B expressed in insect cells were used. For both assays, test compound and/or vehicle were preincubated with purified enzyme in phosphate buffer pH 7.4 for 15 minutes at 37° C. The reaction was initiated by addition of 50 μm kynuramine. Following a 60 minute incubation period, the reaction was terminated by the addition of 6 N NaOH. The amount of 4-hydroxyquinoline that formed was determined by spectrofluorimetrically at 325 nm/465 nm.

Results were converted to percent inhibition, and the EC50 (M) for each reaction was determined using the XLfit program from IDBS (ID Business Solutions Ltd., 2 Occam Court, Surrey Research Park, Guildford, Surrey, GU2 7QB UK). The EC50 represents the concentration of a compound where 50% of its maximal effect is observed. The $pEC_{50}$ is defined as the negative logarithm of the $EC_{50}$; a higher pEC50 value therefore corresponds to higher potency in the assay.

Pharmacological Example 1

MAO-B Inhibition

Representative compounds of the invention were evaluated in the MAO-B enzymatic assay. Typically, the compounds of the invention show MAO-B inhibitory properties at a concentration of 0.1 to 10 μM, typically at 5-100%.

As depicted in the following Table, these inhibitory properties were mirrored by $pEC_{50}$ values ranging from 5 (meaning $10^{-5}$ M or 10 μM) to greater than 7 (meaning less than $10^{-7}$ M or 0.1 μM).

| MAO-B ($pEC_{50}$) | Example Number |
|---|---|
| >7 | 1, 2, 3, 4, 5, 7, 9, 12, 13, 14, 15, 16, 17, 18, 19, 20, 21, 22, 23, 24, 26, 27, 28, 29, 30, 31, 32, 33, 34, 35, 36, 37, 40, 41, 42, 43, 44, 45, 46, 47, 50, 54, 55, 56, 57, 58, 60, 61, 62, 64, 65, 67, 68, 69, 70, 71, 72, 73, 74, 75, 76, 77, 78, 79, 80, 82, 83 |
| 6-7 | 6, 8, 10, 11, 25, 38, 39, 48, 51, 53, 59, 66, 81 |
| 5-6 | 49, 52, 63 |

In specific embodiments, a compound of the present invention shows MAO-B inhibitory properties at a concentration of less than about 50 μM, 40 μM, 35 μM, 25 μM, 20 μM, 15 μM, 10 μM, 5 μM, 1 μM, 500 nM, 400 nM, 300 nM, 200 nM, 100 nM, 75 nM, 50 nM, 25 nM, 10 nM, 5 nM, or 1 nM.

Pharmacological Example 2

MAO-B Selectivity

Exemplary compounds of the present invention showed greater selectivity for MAO-B over MAO-A, as indicated in the following Table.

| MAO-A/MAO-B | Example Number |
|---|---|
| >200 | 12, 14, 15, 16, 27 |
| >100-200 | 2, 5, 7, 9, 13, 17 |
| >10-100 | 1, 3, 6, 8, 10, 18, 24, 25 |
| 1-10 | 4, 11 |

In specific embodiments, a compound of the present invention shows greater than 2-fold, 5-fold, 10-fold, 50-fold, 100-fold, or 200-fold, 500-fold, or 1000-fold selectivity for MAO-B over MAO-A.

Biological Examples

The present disclosure will be further illustrated by the following biological examples. These examples are understood to be exemplary only and are not intended to limit the scope of the invention disclosed herein.

Behavioral Assays

Numerous behavioral assays are available to assess the ability of a candidate compound to enhance memory formation, including contextual conditioning (e.g., fear conditioning), temporal conditioning (e.g., trace conditioning), and object recognition. Other non-limiting examples of appropriate assays to assess memory include those that incorporate or relate to multiple training sessions, spaced training sessions, contextual fear training with single or multiple trials, trace fear conditioning with single or multiple trials, contextual memory generally, temporal memory, spatial memory, episodic memory, passive avoidance memory, active avoidance memory, food preference memory, conditioned taste avoidance, and social recognition memory.

The behavioral assays can also be used in accordance with the present invention, as will be understood by those of ordinary skill in the art. These assays can be directed towards the evaluation of, without limitation, hippocampus-, cortex-, and/or amygdala-dependent memory formation or cognitive performance.

Biological Example 1

Effect of MAO-B Inhibitors on Contextual Memory

Rationale

Contextual fear conditioning is a form of associative learning in which animals learn to recognize a training environment (conditioned stimulus, CS) that has been previously paired with an aversive stimulus such as foot shock (unconditioned stimulus, US). When exposed to the same context at a later time, conditioned animals show a variety of conditional fear responses, including freezing behavior. The percent of time during the test that the animal exhibits such freezing provides a quantitative measure of the contextual associative memory (e.g., Fanselow, *Behav. Neurosci.* 1984, 98, 269-277; Fanselow, *Behav. Neurosci.* 1984, 98, 79-95; and Phillips and LeDoux, *Behav. Neurosci.* 1992, 106, 274-285).

Contextual conditioning has been extensively used to investigate the neural substrates mediating fear-motivated learning (e.g., Phillips and LeDoux, *Behav. Neurosci.* 1992, 106, 274-285; Kim et al., *Behav. Neurosci.* 1993, 107, 1093-1098; and Bourtchouladze et al., *Learn. Mem.* 1998, 5, 365-374). Studies in mice and rats provided evidence for functional interaction between hippocampal and nonhippocampal systems during contextual conditioning training (e.g., Maren et al., *Behav. Brain Res.* 1997, 88, 261-274; Maren et al., *Neurobiol. Learn. Mem.* 1997, 67, 142-149; and Frankland et al., *Behav. Neurosci.* 1998, 112, 863-874). Specifically, post-training lesions of the hippocampus (but not pre-training lesions) greatly reduced contextual fear, implying that: 1) the hippocampus is essential for contextual memory but not for contextual learning per se and 2) in the absence of the hippocampus during training, non-hippocampal systems can support contextual conditioning.

Contextual conditioning has been extensively used to study the impact of various mutations on hippocampus-dependent learning, as well as strain and genetic background differences in mice (e.g., Bourtchouladze et al., *Cell* 1994, 79, 59-68; Bourtchouladze et al., *Learn Mem.* 1998, 5, 365-374; Kogan et al., *Current Biology* 1997, 7, 1-11; Silva et al., *Current Biology* 1996, 6, 1509-1518; Abel et al., *Cell* 1997, 88, 615-626; Giese et al., *Science* 1998, 279, 870-873; Logue et al., *Neuroscience* 1997, 80, 1075-1086; Chen et al., *Behav. Neurosci.* 1996, 110, 1177-1180; and Nguyen et al., *Learn Mem.* 2000, 7, 170-179).

Because robust learning can be triggered with a few minutes training session, contextual conditioning has been especially useful to study the biology of temporally distinct processes of short- and long-term memory (e.g., Kim et al., *Behav. Neurosci.* 1993, 107, 1093-1098; Bourtchouladze et al., *Cell* 1994, 79, 59-68; Abel et al., *Cell* 1997, 88, 615-626; Logue et al., *Behav. Neurosci.* 1997, 111, 104-113; Bourtchouladze et al., *Learn. Mem.* 1998, 5, 365-374 and Nguyen et al., *Learn. Mem.* 2000, 7, 170-179). As such, contextual conditioning provides an excellent model to evaluate the effects of novel drug compounds on hippocampal-dependent memory formation.

Procedures

Previous investigations have established that training with 1× or 2×CS—US pairings induces sub-maximal (weak) memory in wild-type mice (e.g., U.S. 2009/0053140; Tully et al., *Nat. Rev. Drug Discov.* 2003, 2, 267-77; and Bourtchouladze et al. *Learn. Mem.* 1998, 5, 365-374). Accordingly, contextual conditioning in this study was performed as described by Bourtchouladze et al., *Cell* 1994, 79, 59-68.

Young-adult (10-12 weeks old) C57BL/6 male mice and Sprague Dawley male rats were used. Mice and rats were group-housed in standard laboratory and maintained on a 12:12 light-dark cycle. The experiments were always conducted during the light phase of the cycle. With the exception of testing times, the mice had ad libidum access to food and water. To assess contextual memory, a modified contextual fear conditioning task originally developed for evaluation of memory in CREB knock-out mice was used (Bourtchouladze et al., 1994). Training sessions were comprised of a baseline period in the conditioning chamber (Med Associates, Inc.) followed by presentation of unconditioned stimuli (1-5 foot-shocks each at 0.2-1.0 mA for 2-sec) spaced at 60-sec intervals. Thirty seconds following the last shock, the animal is returned to the home cage. One to 7 days later, the animals are returned to the chamber and freezing behavior is scored. Freezing (complete immobility except respiration) is scored by Video Freeze software (Med Associates, Inc.) over an 8 minute test period. Treatment with cognition enhancers are expected to significantly increase freezing when compared with controls.

All experiments were designed and performed in a counterbalanced fashion. In each experiment, the experimenter was unaware (blind) to the treatment of the subjects during training and testing. Training and test sessions were recorded as digital video files. Data were analyzed by one-way ANOVA with appropriate post-hoc tests using GraphPad Prism software package.

Results

Exemplary compounds were found to enhance contextual memory in the fear conditioning assay. Significant enhancing effects were seen at several concentrations, including 0.01 mg/kg, 0.03 mg/kg, and 1.0 mg/kg.

Biological Example 2

Effect of MAO-B Inhibitors on Novel Object Recognition

Rationale

Novel Object Recognition (NOR) is an assay of recognition learning and memory retrieval, and it takes advantage of the spontaneous preference of rodents to investigate a novel object compared with a familiar one. It is an ethologically relevant task, which in contrast to fear conditioning, does not result from negative reinforcement (foot shock)(e.g., Ennaceur and Delacour, *Behav. Brain Res.* 1988, 31, 47-59).

The NOR test has been employed extensively to assess the potential cognitive-enhancing properties of novel compounds derived from high-throughput screening. Object recognition the task relies on the natural curiosity of rodents to explore novel objects in their environments more than familiar ones. Obviously, for an object to be "familiar," the animal must have attended to it before and remembered that experience. Hence, animals with better memory will attend and explore a new object more than an object familiar to them. During testing, the animal is presented with the training object and a second, novel one. Memory of the training object renders it familiar to the animal, and it then spends more time exploring the new novel object rather than the familiar one (Bourtchouladze et. al., *Proc. Natl. Acad. Sci. USA* 2003, 100, 10518-10522).

Neuroimaging, pharmacological, and lesion studies have demonstrated that the hippocampus and adjacent perirhinal cortex are critical for object recognition memory in rodents, monkeys, and humans (e.g., Mitchell, *Behav. Brain Res.* 1998, 97, 107-113; Teng et al., *J. Neurosci.* 2000, 20, 3853-3863; Mumby, *Brain Res.* 2001, 127, 159-181; Eichenbaum et al., *Annu. Rev. Neurosci.* 2007, 30, 127-152; Squire et al., *Nat. Rev. Neurosci.* 2007, 8, 872-883; and Vann and Alabasser, *Curr. Opin. Neurobiol.* 2011, 21, 440-445). Hence, object recognition provides an excellent behavioral model to evaluate drug-compound effects on cognitive tasks associated with function of the hippocampus and cortex.

Procedures

Object recognition was tested in young adult mice and rats using the following protocol. Animals are briefly handled by the experimenter 2-5 days prior to training. Each compound was administered between 15 minutes and 24-hours prior to, or following, training. Habituation sessions (duration 1-20 min, over 1-3 days) were conducted to familiarize the animal to the arena. During training trials (duration of 1-20 min) the animals were allowed to explore two identical objects. A test trial (duration of 1-20 min) was then performed 1-96 hrs later.

For novel object recognition, one object is replaced with one that is novel. All combinations and locations of objects are used in a balanced manner to reduce potential biases attributable to preference for particular locations or objects. Training and test trials are recorded and scored by video-tracking software (e.g. Noldus Ethovision). An animal is scored as exploring an object when its head was oriented toward the object within a distance of 1 cm (rat)/2 cm (mouse) or when the nose is touching the object. Turning around, climbing, or sitting on an object was not considered as exploration. If the animal generates a long-term memory for the familiar object, it will spend significantly more time exploring the novel object compared to the familiar object during the retention test (Cognitive enhancers are therefore expected to facilitate this discrimination between the familiar and novel object).

A discrimination index was calculated as previously described (Bourtchouladze et al., *Proc. Natl. Acad. Sci. USA* 2003, 100, 10518-10522). In each experiment, the experimenter was unaware (blind) to the treatment of the subjects during training and testing. Data were analyzed by one-way ANOVA with appropriate post-hoc tests using GraphPad Prism software package.

Results

Exemplary compounds of Formula (I) were found to significantly enhance 24 hour memory. Significant effects were seen at several concentrations, including 1.0 mg/kg and 3 mg/kg. Control experiments showed that compound administration did not significantly affect the cumulative distance traveled or amount of time spent exploring the left and right halves of the box.

Taken together, these results show that MAO-B is a negative regulator of memory formation in the hippocampus, a temporal lobe structure that is critical to memory formation in rodents as well as in humans. Importantly, MAO-B siRNA has been previously shown to induce a 'gain of function' (that is, enhancement of contextual and temporal memory formation). Hence these results confirm that MAO-B is a valid target for enhancing cognition, and memory specifically.

The specification, including the examples, is intended to be exemplary only, and it will be apparent to those skilled in the art that various modifications and variations can be made in the present invention without departing from the scope or spirit of the invention as defined by the appended claims.

Furthermore, while certain details in the present disclosure are provided to convey a thorough understanding of the invention as defined by the appended claims, it will be apparent to those skilled in the art that certain embodiments may be practiced without these details. Moreover, in certain instances, well-known methods, procedures, or other specific details have not been described to avoid unnecessarily obscuring aspects of the invention defined by the appended claims.

What is claimed is:

1. A compound selected from the groups consisting of:

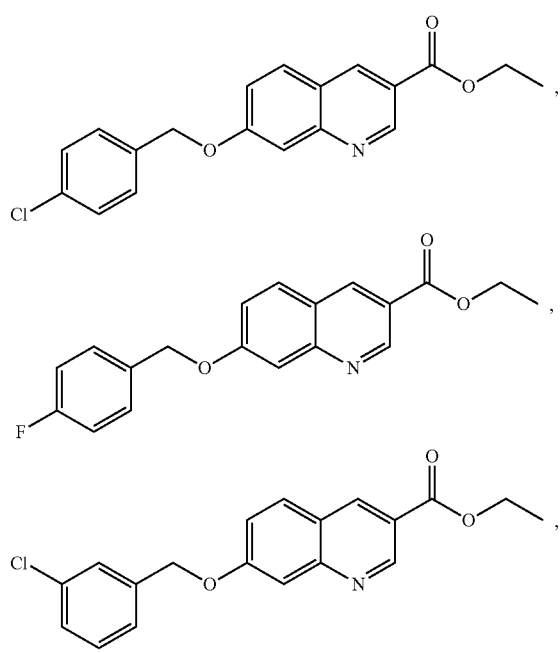

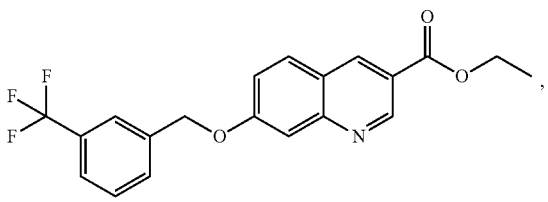

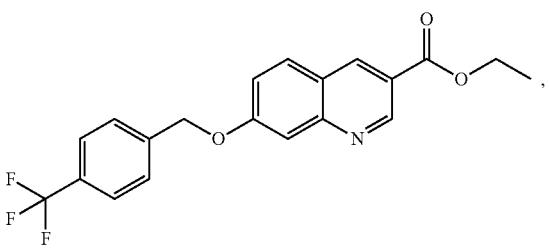

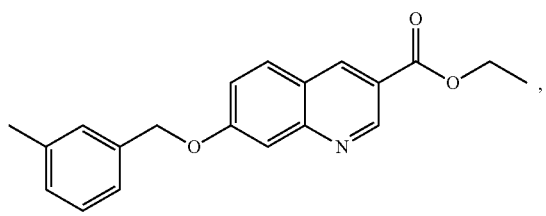

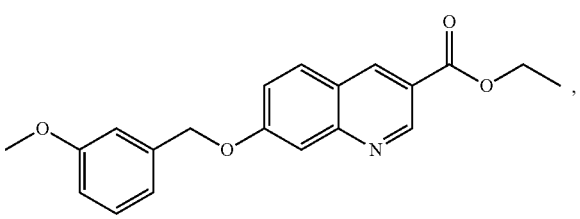

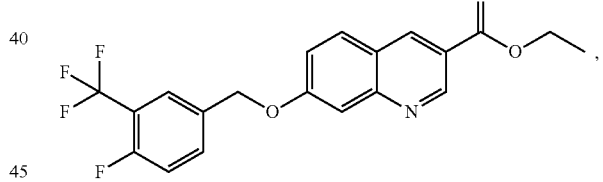

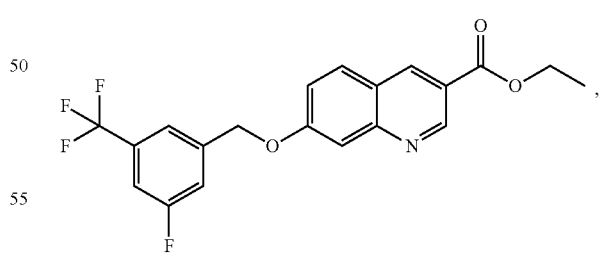

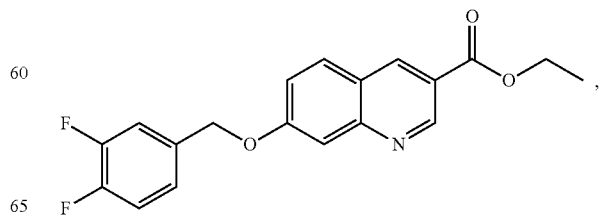

105
-continued
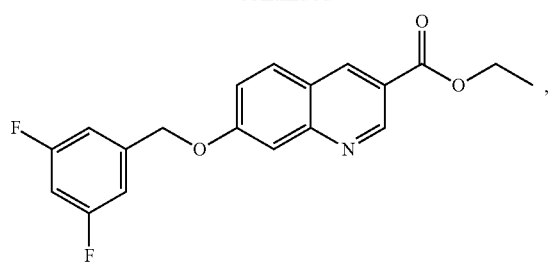
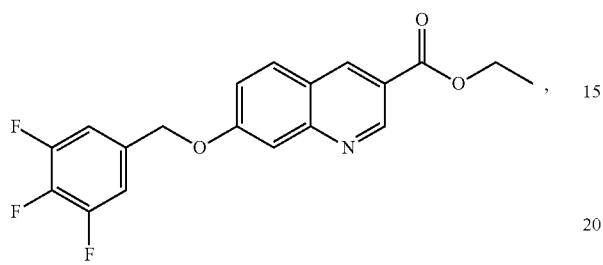
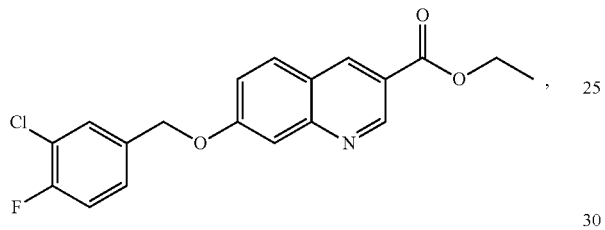
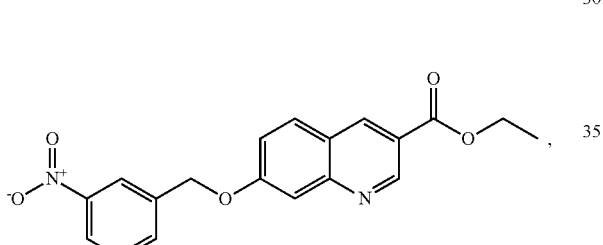
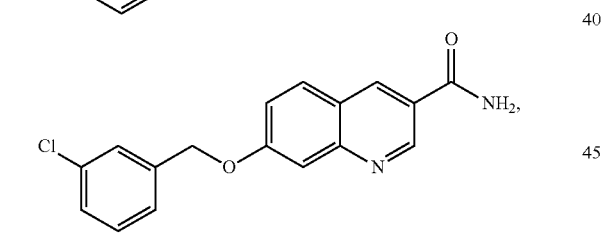
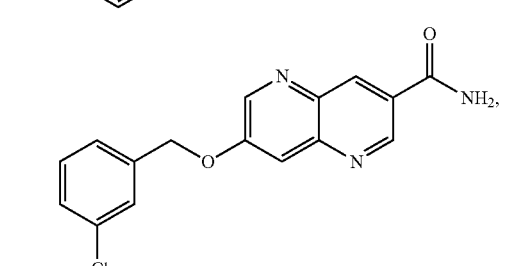
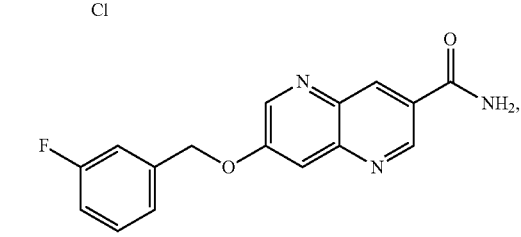
106
-continued
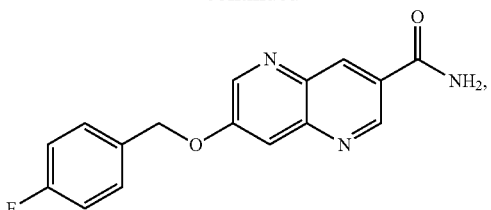
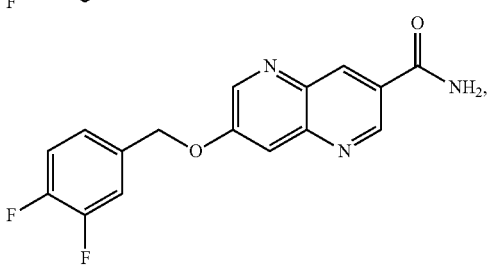
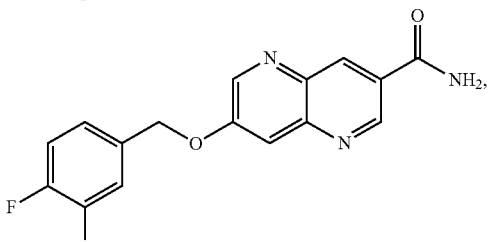
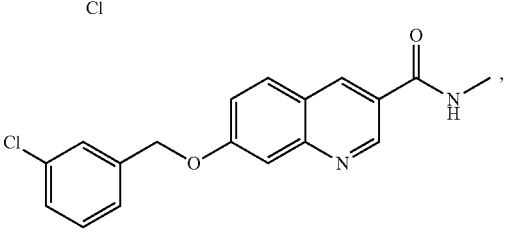
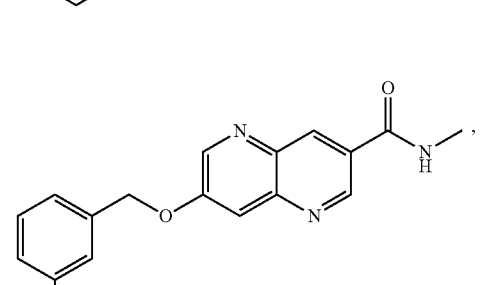
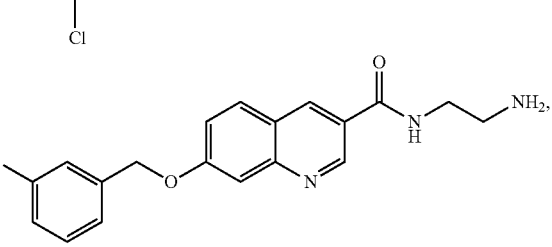
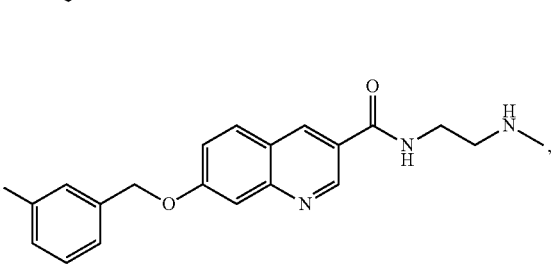

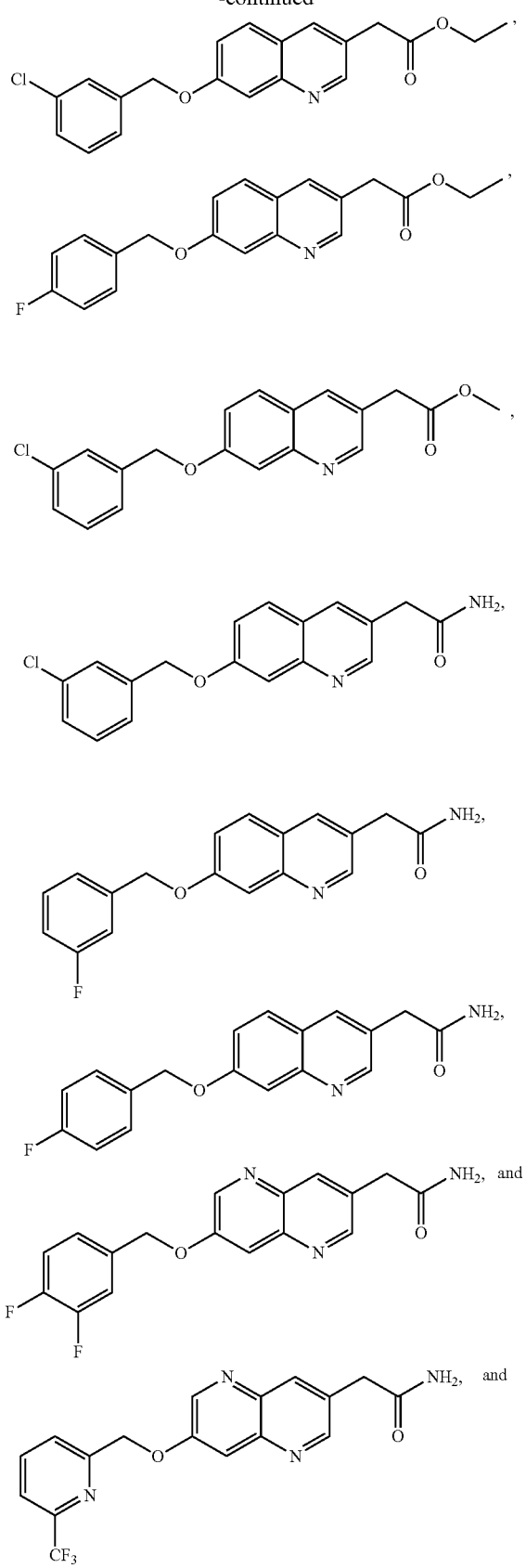
pharmaceutically acceptable salts thereof.
2. The compound of compound of claim 1 selected from the groups consisting of:
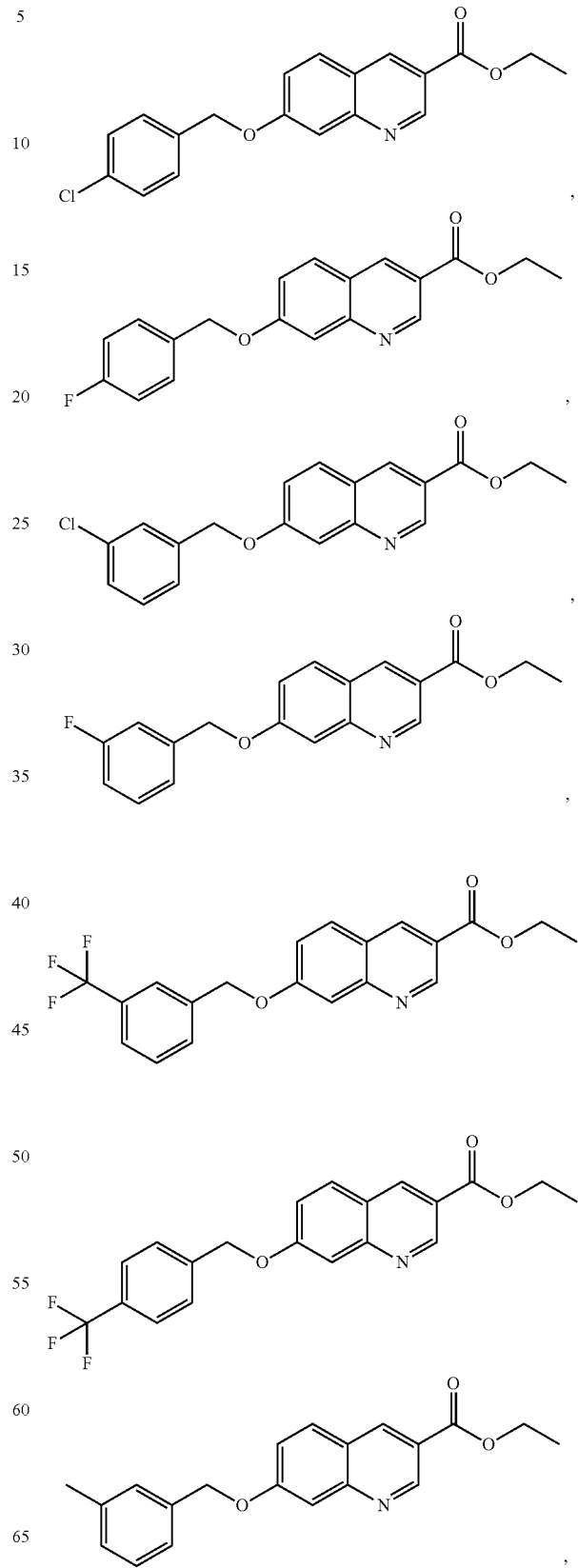

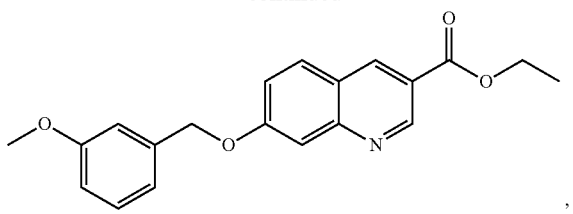
,
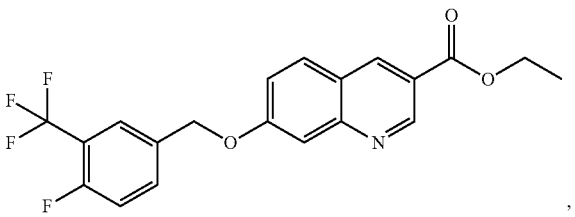
,
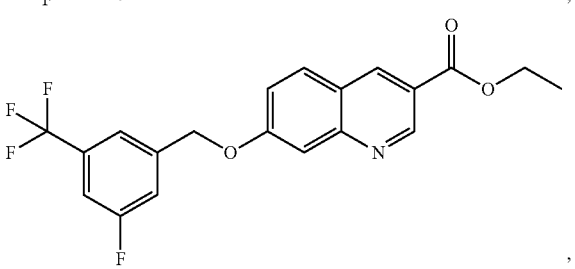
,
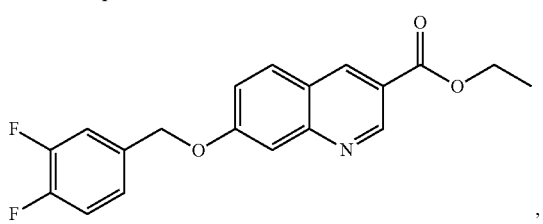
,
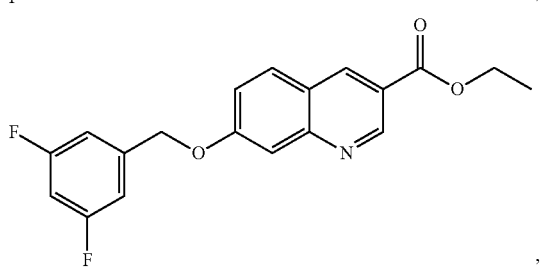
,
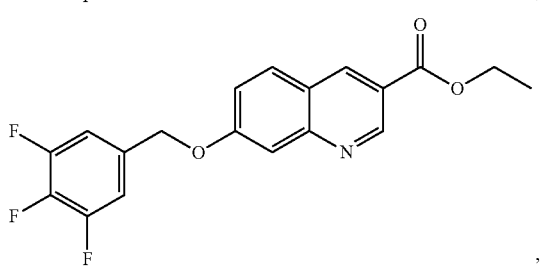
,
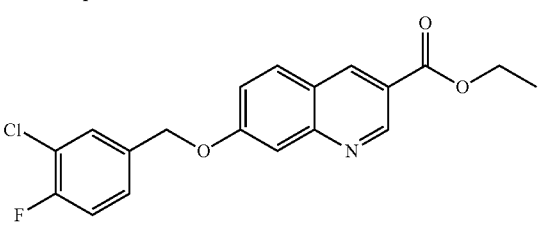
,
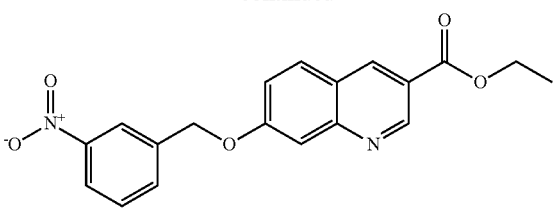
,
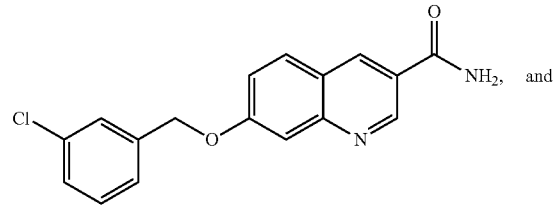
, and
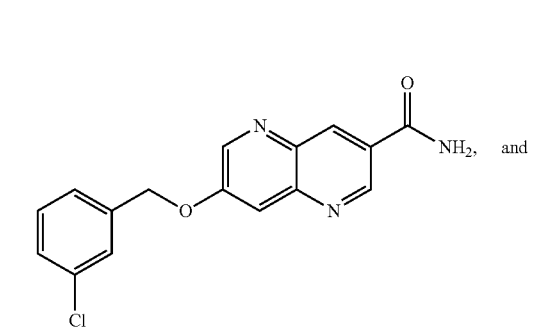
, and
pharmaceutically acceptable salts thereof.
3. The compound of compound of claim 1 selected from the groups consisting of:

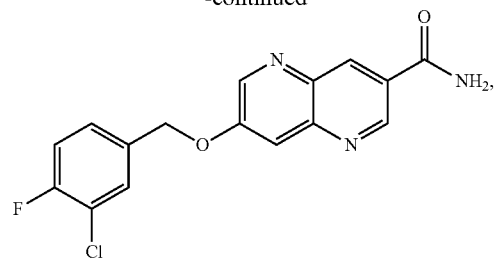
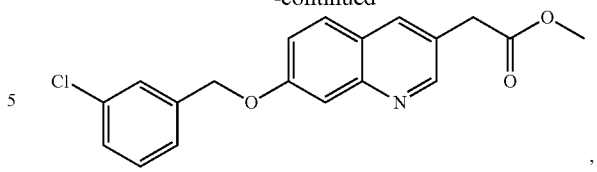
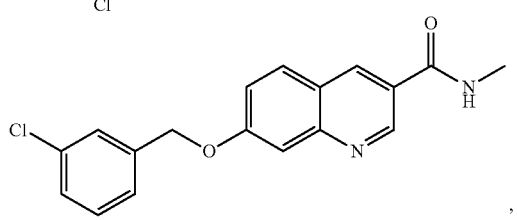
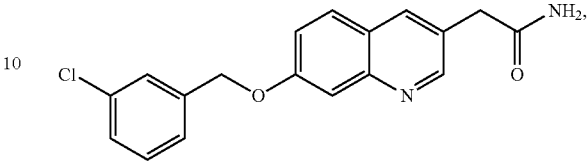
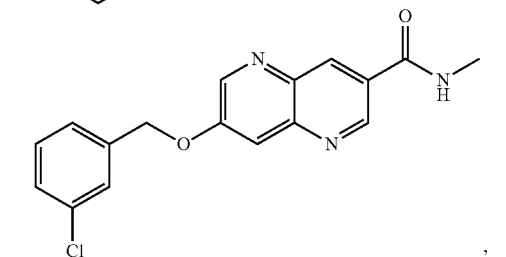
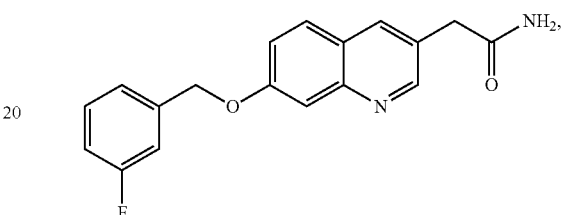
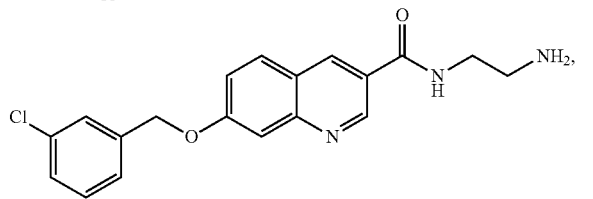
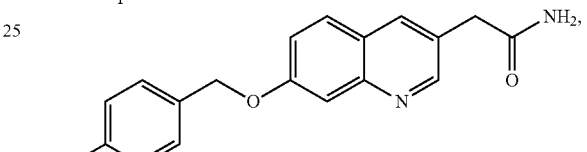
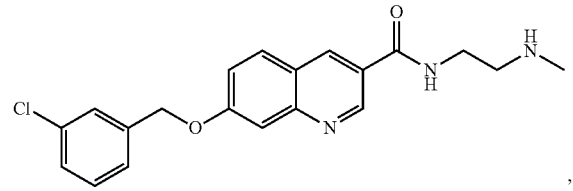
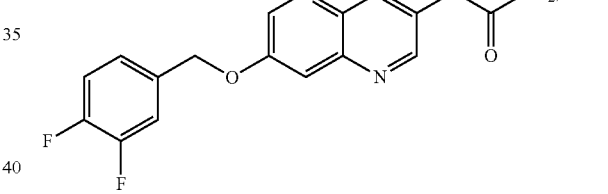
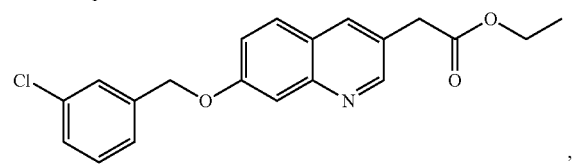
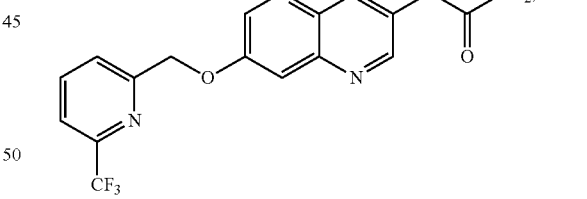
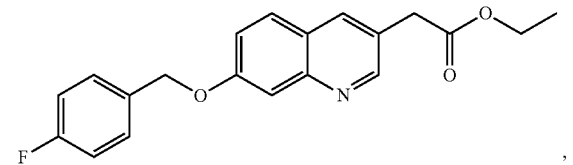
pharmaceutically acceptable salts thereof.
* * * * *